(12) United States Patent
D'Halluin et al.

(10) Patent No.: US 9,670,496 B2
(45) Date of Patent: Jun. 6, 2017

(54) METHODS AND MEANS TO MODIFY A PLANT GENOME

(71) Applicants: Bayer CropScience NV, Diegem (BE); Bayer CropScience AG, Monheim am Rhein (DE); Bayer CropScience LP, Research Triangle Park, NC (US)

(72) Inventors: Kathleen D'Halluin, Mariakerke (BE); Jan Dittgen, Frankfurt am Main (DE); Stefan Jansens, Ghent (BE); Frank Meulewaeter, Merelbeke (BE); Koen Weterings, Leichlingen (DE); Hal Moser, Bakersfield, CA (US); Thomas Wilde, Weilrod-Hasselbach (DE); Ruediger Hain, Frankfurt (DE); Udo Bickers, Cologne (DE); Linda Trolinder, Shallowater, TX (US); Gary Henniger, Lubbock, TX (US)

(73) Assignees: Bayer CropScience N.V., Diegem (BE); Bayer CropScience AG, Monheim am Rhein (DE); Bayer CropScience LP, Research Triangle Park, NC (US)

( * ) Notice: Subject to any disclaimer, the term of this patent is extended or adjusted under 35 U.S.C. 154(b) by 377 days.

(21) Appl. No.: 14/201,577

(22) Filed: Mar. 7, 2014

(65) Prior Publication Data
US 2014/0196169 A1   Jul. 10, 2014

Related U.S. Application Data

(62) Division of application No. 14/240,500, filed as application No. PCT/EP2012/065867 on Aug. 14, 2012.

(60) Provisional application No. 61/525,892, filed on Aug. 22, 2011, provisional application No. 61/569,518, filed on Dec. 12, 2011.

(30) Foreign Application Priority Data

Aug. 25, 2011 (EP) ..................................... 11075198
Dec. 12, 2011 (EP) ..................................... 11193103

(51) Int. Cl.
*C12N 15/82* (2006.01)
*A01N 29/00* (2006.01)
*C12N 15/09* (2006.01)
*C12N 15/63* (2006.01)
*C12N 9/02* (2006.01)
*C12N 15/01* (2006.01)

(52) U.S. Cl.
CPC ....... *C12N 15/8201* (2013.01); *C12N 9/0069* (2013.01); *C12N 15/01* (2013.01); *C12N 15/8213* (2013.01); *C12N 15/8245* (2013.01); *C12N 15/8247* (2013.01); *C12N 15/8271* (2013.01); *C12N 15/8274* (2013.01); *C12N 15/8279* (2013.01); *C12N 15/8282* (2013.01); *C12N 15/8286* (2013.01); *C12Y 113/11027* (2013.01)

(58) Field of Classification Search
CPC .................................. C12N 9/02; C12N 15/82
See application file for complete search history.

(56) References Cited

U.S. PATENT DOCUMENTS

| | | | |
|---|---|---|---|
| 4,761,373 A | 8/1988 | Anderson et al. |
| 4,945,050 A | 7/1990 | Sanford et al. |
| 4,962,028 A | 10/1990 | Bedbrook et al. |
| 5,004,863 A | 4/1991 | Umbeck |
| 5,013,659 A | 5/1991 | Bedbrook et al. |
| 5,015,580 A | 5/1991 | Christou et al. |
| 5,141,870 A | 8/1992 | Bedbrook et al. |
| 5,164,316 A | 11/1992 | McPherson et al. |
| 5,196,525 A | 3/1993 | McPherson et al. |
| 5,273,894 A | 12/1993 | Strauch et al. |
| 5,276,268 A | 1/1994 | Strauch et al. |
| 5,304,732 A | 4/1994 | Anderson et al. |
| 5,322,938 A | 6/1994 | McPherson et al. |
| 5,331,107 A | 7/1994 | Anderson et al. |
| 5,352,605 A | 10/1994 | Fraley et al. |
| 5,359,142 A | 10/1994 | McPherson et al. |
| 5,378,824 A | 1/1995 | Bedbrook et al. |
| 5,384,253 A | 1/1995 | Krzyzek et al. |
| 5,424,200 A | 6/1995 | McPherson et al. |

(Continued)

FOREIGN PATENT DOCUMENTS

| | | |
|---|---|---|
| AU | 689311 B2 | 3/1996 |
| DE | 0571427 B1 | 10/2003 |

(Continued)

OTHER PUBLICATIONS

Lingenfelter, D. D., et al. . "Isoxaflutole vs. mesotrione: the battle of the bleachers." Proceedings of the Annual Meeting-Northeastern Weed Science Society. vol. 56. [np]; 1999, 2002.*

(Continued)

*Primary Examiner* — Lee A Visone
*Assistant Examiner* — Fan Fan
(74) *Attorney, Agent, or Firm* — Arent Fox LLP

(57) ABSTRACT

Methods and means are provided to modify in a targeted manner the genome of a plant in close proximity to an existing elite event using a double stranded DNA break inducing enzyme. Also provided are plants, in particular cotton plants showing tolerance to a field dose of at least 1× of at least one HPPD inhibitor, and methods for making such plants.

28 Claims, 4 Drawing Sheets

(56) References Cited

U.S. PATENT DOCUMENTS

| | | | |
|---|---|---|---|
| 5,463,175 A | 10/1995 | Barry et al. |
| 5,464,765 A | 11/1995 | Coffee et al. |
| 5,504,200 A | 4/1996 | Hall et al. |
| 5,508,184 A | 4/1996 | Negrutiu et al. |
| 5,510,471 A | 4/1996 | Lebrun et al. |
| 5,510,474 A | 4/1996 | Quail et al. |
| 5,538,880 A | 7/1996 | Lundquist et al. |
| 5,550,318 A | 8/1996 | Adams et al. |
| 5,561,236 A | 10/1996 | Leemans et al. |
| 5,591,616 A | 1/1997 | Hiei et al. |
| 5,593,874 A | 1/1997 | Brown et al. |
| 5,605,011 A | 2/1997 | Bedbrook et al. |
| 5,608,152 A | 3/1997 | Kridl et al. |
| 5,633,448 A | 5/1997 | Lebrun et al. |
| 5,635,055 A | 6/1997 | Sweet et al. |
| 5,637,489 A | 6/1997 | Strauch et al. |
| 5,641,876 A | 6/1997 | McElroy et al. |
| 5,646,024 A | 7/1997 | Leemans et al. |
| 5,648,477 A | 7/1997 | Leemans et al. |
| 5,659,122 A | 8/1997 | Austin |
| 5,670,349 A | 9/1997 | Cramer et al. |
| 5,712,107 A | 1/1998 | Nichols |
| 5,731,180 A | 3/1998 | Dietrich |
| 5,739,082 A | 4/1998 | Donn |
| 5,767,361 A | 6/1998 | Dietrich |
| 5,776,760 A | 7/1998 | Barry et al. |
| 5,824,790 A | 10/1998 | Keeling et al. |
| 5,824,877 A | 10/1998 | Hinchee et al. |
| 5,908,810 A | 6/1999 | Donn |
| 5,908,975 A | 6/1999 | Caimi et al. |
| 5,928,937 A | 7/1999 | Kakefuda et al. |
| 5,981,840 A | 11/1999 | Zhao et al. |
| 6,013,861 A | 1/2000 | Bird et al. |
| 6,160,208 A | 12/2000 | Lundquist et al. |
| 6,245,968 B1* | 6/2001 | Boudec ............... C12N 9/0069 435/320.1 |
| 6,284,479 B1 | 9/2001 | Nichols |
| 6,372,960 B1* | 4/2002 | Michiels ............ C12N 15/8289 435/199 |
| 6,384,301 B1 | 5/2002 | Martinell et al. |
| 6,399,861 B1 | 6/2002 | Anderson et al. |
| 6,403,865 B1 | 6/2002 | Koziel et al. |
| 6,468,747 B1 | 10/2002 | De Beuckeleer et al. |
| 6,483,013 B1 | 11/2002 | Reynaerts et al. |
| 6,566,587 B1 | 5/2003 | Lebrun et al. |
| 6,734,341 B2 | 5/2004 | Sinletary et al. |
| 6,762,344 B1* | 7/2004 | Spencer ................. A01H 1/04 800/266 |
| 6,768,044 B1 | 7/2004 | Boudec et al. |
| 7,053,205 B1 | 5/2006 | Verdaguer et al. |
| 7,112,665 B1 | 9/2006 | Leemans et al. |
| 7,304,209 B2* | 12/2007 | Zink ................. C12N 9/0008 435/320.1 |
| 7,399,621 B2 | 7/2008 | Hammer et al. |
| 7,504,561 B2 | 3/2009 | Hammer et al. |
| 7,659,376 B2 | 2/2010 | Hammer et al. |
| 8,309,332 B2 | 11/2012 | Peters et al. |
| 2001/0026941 A1 | 10/2001 | Held et al. |
| 2001/0029014 A1 | 10/2001 | Beuckeleer |
| 2002/0015066 A1 | 2/2002 | Siwinski et al. |
| 2002/0031826 A1 | 3/2002 | Nichols |
| 2002/0102582 A1 | 8/2002 | Levine |
| 2002/0120964 A1 | 8/2002 | Rangwala et al. |
| 2003/0097687 A1 | 5/2003 | Trolinder et al. |
| 2003/0126634 A1 | 7/2003 | Spencer et al. |
| 2003/0188347 A1 | 10/2003 | Both et al. |
| 2004/0139493 A1 | 7/2004 | Behr et al. |
| 2004/0172669 A1 | 9/2004 | Kraus et al. |
| 2004/0177399 A1 | 9/2004 | Hammer et al. |
| 2004/0250317 A1 | 12/2004 | Huber et al. |
| 2005/0039226 A1 | 2/2005 | Barbour et al. |
| 2005/0086719 A1 | 4/2005 | Spencer et al. |
| 2005/0188434 A1 | 8/2005 | Spencer et al. |
| 2005/0216969 A1 | 9/2005 | Song et al. |
| 2006/0021093 A1 | 1/2006 | Hammer et al. |
| 2006/0021094 A1 | 1/2006 | Hammer et al. |
| 2006/0059581 A1 | 3/2006 | Spencer et al. |
| 2006/0059590 A1 | 3/2006 | Cerny et al. |
| 2006/0070139 A1 | 3/2006 | Bing et al. |
| 2006/0095986 A1 | 5/2006 | Cavato et al. |
| 2006/0130175 A1 | 6/2006 | Ellis et al. |
| 2006/0150269 A1 | 7/2006 | Hammer et al. |
| 2006/0150270 A1 | 7/2006 | Hammer et al. |
| 2006/0162007 A1 | 7/2006 | Guo et al. |
| 2006/0230473 A1 | 10/2006 | Johnson et al. |
| 2006/0253921 A1 | 11/2006 | Carozzi et al. |
| 2006/0282915 A1 | 12/2006 | Malven et al. |
| 2007/0028322 A1 | 2/2007 | Dizigan et al. |
| 2007/0067868 A1 | 3/2007 | Negrotto et al. |
| 2007/0107078 A1 | 5/2007 | Hammer et al. |
| 2007/0136840 A1 | 6/2007 | Peters et al. |
| 2007/0143876 A1 | 6/2007 | Song et al. |
| 2007/0289031 A1 | 12/2007 | Koziel et al. |
| 2007/0289035 A1 | 12/2007 | Vande Berg et al. |
| 2007/0292854 A1 | 12/2007 | Behr et al. |
| 2007/0295151 A1 | 12/2007 | Kentor |
| 2007/0300325 A1 | 12/2007 | Peters et al. |
| 2007/0300326 A1 | 12/2007 | Peters et al. |
| 2008/0028482 A1 | 1/2008 | Beazley et al. |
| 2008/0064032 A1 | 3/2008 | Townshend et al. |
| 2008/0070260 A1 | 3/2008 | Krieb et al. |
| 2008/0127372 A1 | 5/2008 | Schouten et al. |
| 2008/0167456 A1 | 7/2008 | Steiner et al. |
| 2008/0196127 A1 | 8/2008 | De Beuckeleer |
| 2008/0260932 A1 | 10/2008 | Anderson et al. |
| 2008/0289060 A1 | 11/2008 | De Beuckeleer et al. |
| 2008/0312082 A1 | 12/2008 | Kinney et al. |
| 2008/0313769 A9 | 12/2008 | Carr et al. |
| 2008/0320616 A1 | 12/2008 | De Beuckeleer |
| 2009/0018016 A1 | 1/2009 | Duck et al. |
| 2009/0119797 A1 | 5/2009 | Hammer et al. |
| 2009/0126044 A1 | 5/2009 | Carozzi et al. |
| 2009/0130071 A1 | 5/2009 | Gao et al. |
| 2009/0137395 A1 | 5/2009 | Chicoine et al. |
| 2009/0151018 A1 | 6/2009 | Hammer et al. |
| 2009/0203075 A1 | 8/2009 | Hammer et al. |
| 2009/0205076 A1 | 8/2009 | Heinrichs et al. |
| 2009/0210970 A1 | 8/2009 | Hondred et al. |
| 2009/0217423 A1 | 8/2009 | Cayley et al. |
| 2009/0241219 A1 | 9/2009 | Hammer et al. |
| 2009/0265817 A1 | 10/2009 | Weyens et al. |
| 2009/0300784 A1 | 12/2009 | Long et al. |
| 2009/0313717 A1 | 12/2009 | Hernandez et al. |
| 2010/0024077 A1 | 1/2010 | Cayley et al. |
| 2010/0050282 A1 | 2/2010 | Trolinder et al. |
| 2010/0077501 A1 | 3/2010 | Trolinder et al. |
| 2010/0080887 A1 | 4/2010 | Wagner et al. |
| 2010/0184079 A1 | 7/2010 | Cressman, Jr. et al. |
| 2010/0197503 A1 | 8/2010 | Hawkes et al. |
| 2011/0067141 A1 | 3/2011 | Froman et al. |
| 2011/0138504 A1 | 6/2011 | Beazley et al. |

FOREIGN PATENT DOCUMENTS

| | | | |
|---|---|---|---|
| DE | 0633317 B1 | 3/2005 | |
| DE | 0663956 B1 | 6/2005 | |
| DE | 0507698 B1 | 9/2008 | |
| EP | 0719338 B1 | 6/2003 | |
| EP | 04077624.7 | 11/2005 | |
| EP | 04077984.5 | 12/2005 | |
| EP | 0837944 B1 | 3/2006 | |
| EP | 06009836.5 | 7/2007 | |
| EP | 06090134.5 | 9/2007 | |
| EP | 06090227.7 | 2/2008 | |
| EP | 06090228.5 | 2/2008 | |
| EP | 07090009.7 | 3/2008 | |
| EP | 08010791.5 | 5/2008 | |
| EP | 0728213 B1 | 12/2008 | |
| EP | 1689870 B1 | 12/2008 | |
| EP | 08075514.3 | 6/2009 | |
| EP | WO 2009/144079 | * 12/2009 | ............ C12N 15/53 |
| EP | WO2009/144079 | * 12/2009 | ............ C12N 15/53 |
| EP | WO2010142424 | * 12/2010 | ............ A01H 5/10 |
| EP | 1999141 B1 | 6/2011 | |

(56) References Cited

FOREIGN PATENT DOCUMENTS

| | | |
|---|---|---|
| EP | 10005926.0 | 7/2011 |
| EP | 11004570.5 | 6/2012 |
| EP | 1999263 B1 | 4/2013 |
| EP | 2611785 B1 | 6/2014 |
| ES | 2275365 | 4/2008 |
| JP | 2006304779 | 11/2006 |
| WO | WO 84/02913 | 8/1984 |
| WO | WO 87/07644 | 12/1987 |
| WO | WO 89/10396 | 11/1989 |
| WO | WO 90/12107 | 10/1990 |
| WO | WO 91/00915 | 1/1991 |
| WO | WO 91/13980 | 9/1991 |
| WO | WO 92/13956 | 8/1992 |
| WO | WO 92/15675 | 9/1992 |
| WO | WO 94/04693 | 3/1994 |
| WO | WO 94/09144 | 4/1994 |
| WO | WO 94/11520 | 5/1994 |
| WO | WO 94/18313 | 8/1994 |
| WO | WO 94/21795 | 9/1994 |
| WO | WO 95/04826 | 2/1995 |
| WO | WO 95/06742 | 3/1995 |
| WO | WO 95/09233 | 4/1995 |
| WO | WO 95/26407 | 10/1995 |
| WO | WO 95/31553 | 11/1995 |
| WO | WO 95/35026 | 12/1995 |
| WO | WO 96/01904 | 1/1996 |
| WO | WO 96/06932 | 3/1996 |
| WO | WO 96/14408 | 5/1996 |
| WO | WO 96/15248 | 5/1996 |
| WO | WO 96/19581 | 6/1996 |
| WO | WO 96/21023 | 7/1996 |
| WO | WO 96/27674 | 9/1996 |
| WO | WO 96/33270 | 10/1996 |
| WO | WO 96/34968 | 11/1996 |
| WO | WO 96/38567 | 12/1996 |
| WO | WO 97/11188 | 3/1997 |
| WO | WO 97/13865 | 4/1997 |
| WO | WO 97/20936 | 6/1997 |
| WO | WO 97/26362 | 7/1997 |
| WO | WO 97/32985 | 9/1997 |
| WO | WO 97/42328 | 11/1997 |
| WO | WO 97/44472 | 11/1997 |
| WO | WO 97/47806 | 12/1997 |
| WO | WO 97/47807 | 12/1997 |
| WO | WO 97/47808 | 12/1997 |
| WO | WO 97/48819 | 12/1997 |
| WO | WO 98/00549 | 1/1998 |
| WO | WO 98/20145 | 5/1998 |
| WO | WO 98/22604 | 5/1998 |
| WO | WO 98/27212 | 6/1998 |
| WO | WO 98/32326 | 7/1998 |
| WO | WO 98/39460 | 9/1998 |
| WO | WO 98/40503 | 9/1998 |
| WO | WO 98/44140 | 10/1998 |
| WO | WO 98/45445 | 10/1998 |
| WO | WO 98/45461 | 10/1998 |
| WO | WO 99/12950 | 3/1999 |
| WO | WO 99/24585 | 5/1999 |
| WO | WO 99/24586 | 5/1999 |
| WO | WO 99/24593 | 5/1999 |
| WO | WO 99/25842 | 5/1999 |
| WO | WO 99/34008 | 7/1999 |
| WO | WO 99/53072 | 10/1999 |
| WO | WO 99/58654 | 11/1999 |
| WO | WO 99/58688 | 11/1999 |
| WO | WO 99/58690 | 11/1999 |
| WO | WO 99/66050 | 12/1999 |
| WO | WO 00/04173 | 1/2000 |
| WO | WO 00/08175 | 2/2000 |
| WO | WO 00/08184 | 2/2000 |
| WO | WO 00/08185 | 2/2000 |
| WO | WO 00/11192 | 3/2000 |
| WO | WO 00/14249 | 3/2000 |
| WO | WO 00/22140 | 4/2000 |
| WO | WO 00/26345 | 5/2000 |
| WO | WO 00/26356 | 5/2000 |
| WO | WO 00/28052 | 5/2000 |
| WO | WO 00/46386 | 8/2000 |
| WO | WO 00/47727 | 8/2000 |
| WO | WO 00/66746 | 11/2000 |
| WO | WO 00/66747 | 11/2000 |
| WO | WO 00/71733 | 11/2000 |
| WO | WO 00/73422 | 12/2000 |
| WO | WO 00/77229 | 12/2000 |
| WO | WO 01/12782 | 2/2001 |
| WO | WO 01/12826 | 2/2001 |
| WO | WO 01/14569 | 3/2001 |
| WO | WO 01/17333 | 3/2001 |
| WO | WO 01/19975 | 3/2001 |
| WO | WO 01/24615 | 4/2001 |
| WO | WO 01/31042 | 5/2001 |
| WO | WO 01/38514 | 5/2001 |
| WO | WO 01/41558 | 6/2001 |
| WO | WO 01/51654 | 7/2001 |
| WO | WO 01/66704 | 9/2001 |
| WO | WO 01/98509 | 12/2001 |
| WO | WO 02/26995 | 4/2002 |
| WO | WO 02/34923 | 5/2002 |
| WO | WO 02/34946 | 5/2002 |
| WO | WO 02/36782 | 5/2002 |
| WO | WO 02/36787 | 5/2002 |
| WO | WO 02/36831 | 5/2002 |
| WO | WO 02/44407 | 6/2002 |
| WO | WO 02/45485 | 6/2002 |
| WO | WO 02/46387 | 6/2002 |
| WO | WO 02/079410 | 10/2002 |
| WO | WO 02/100163 | 12/2002 |
| WO | WO 02/101059 | 12/2002 |
| WO | WO 03/004659 | 1/2003 |
| WO | WO 03/013224 | 2/2003 |
| WO | WO 03/013226 | 2/2003 |
| WO | WO 03/033540 | 4/2003 |
| WO | WO 03/052073 | 6/2003 |
| WO | WO 03/052108 | 6/2003 |
| WO | WO 03/071860 | 9/2003 |
| WO | WO 03/080809 | 10/2003 |
| WO | WO 03/092360 | 11/2003 |
| WO | WO 2004/011601 | 2/2004 |
| WO | WO 2004/024928 | 3/2004 |
| WO | WO 2004/039986 | 5/2004 |
| WO | WO 2004/040012 | 5/2004 |
| WO | WO 2004/053062 | 6/2004 |
| WO | WO 2004/053135 | 6/2004 |
| WO | WO 2004/053219 | 6/2004 |
| WO | WO 2004/056999 | 7/2004 |
| WO | WO 2004/067736 | 8/2004 |
| WO | WO 2004/072235 | 8/2004 |
| WO | WO 2004/074443 | 9/2004 |
| WO | WO 2004/074492 | 9/2004 |
| WO | WO 2004/078983 | 9/2004 |
| WO | WO 2004/090140 | 10/2004 |
| WO | WO 2004/099447 | 11/2004 |
| WO | WO 2004/106529 | 12/2004 |
| WO | WO 2005/002359 | 1/2005 |
| WO | WO 2005/012515 | 2/2005 |
| WO | WO 2005/012529 | 2/2005 |
| WO | WO 2005/017157 | 2/2005 |
| WO | WO 2005/020673 | 3/2005 |
| WO | WO 2005/030941 | 4/2005 |
| WO | WO 2005/030942 | 4/2005 |
| WO | WO 2005/049842 | 6/2005 |
| WO | WO 2005/054479 | 6/2005 |
| WO | WO 2005/054480 | 6/2005 |
| WO | WO 2005/059103 | 6/2005 |
| WO | WO 2005/061720 | 7/2005 |
| WO | WO 2005/093093 | 10/2005 |
| WO | WO 2005/095617 | 10/2005 |
| WO | WO 2005/095618 | 10/2005 |
| WO | WO 2005/095619 | 10/2005 |
| WO | WO 2005/095632 | 10/2005 |
| WO | WO 2005/098004 | 10/2005 |
| WO | WO 2005/103266 | 11/2005 |
| WO | WO 2005/103301 | 11/2005 |
| WO | WO 2005/123927 | 12/2005 |

(56) References Cited

FOREIGN PATENT DOCUMENTS

| | | |
|---|---|---|
| WO | WO 2006/007373 | 1/2006 |
| WO | WO 2006/015376 | 2/2006 |
| WO | WO 2006/018319 | 2/2006 |
| WO | WO 2006/024351 | 3/2006 |
| WO | WO 2006/032426 | 3/2006 |
| WO | WO 2006/032538 | 3/2006 |
| WO | WO 2006/045633 | 5/2006 |
| WO | WO 2006/060634 | 6/2006 |
| WO | WO 2006/063862 | 6/2006 |
| WO | WO 2006/072603 | 7/2006 |
| WO | WO 2006/098952 | 9/2006 |
| WO | WO 2006/103107 | 10/2006 |
| WO | WO 2006/105946 | 10/2006 |
| WO | WO 2006/108674 | 10/2006 |
| WO | WO 2006/108675 | 10/2006 |
| WO | WO 2006/108702 | 10/2006 |
| WO | WO 2006/128568 | 12/2006 |
| WO | WO 2006/128569 | 12/2006 |
| WO | WO 2006/128570 | 12/2006 |
| WO | WO 2006/128571 | 12/2006 |
| WO | WO 2006/128572 | 12/2006 |
| WO | WO 2006/128573 | 12/2006 |
| WO | WO 2006/129204 | 12/2006 |
| WO | WO 2006/130436 | 12/2006 |
| WO | WO 2006/132270 | 12/2006 |
| WO | WO 2006/136351 | 12/2006 |
| WO | WO 2007/009823 | 1/2007 |
| WO | WO 2007/017186 | 2/2007 |
| WO | WO 2007/024782 | 3/2007 |
| WO | WO 2007/027777 | 3/2007 |
| WO | WO 2007/035650 | 3/2007 |
| WO | WO 2007/039314 | 4/2007 |
| WO | WO 2007/039315 | 4/2007 |
| WO | WO 2007/039316 | 4/2007 |
| WO | WO 2007/047859 | 4/2007 |
| WO | WO 2007/049095 | 5/2007 |
| WO | WO 2007/049156 | 5/2007 |
| WO | WO 2007/074405 | 7/2007 |
| WO | WO 2007/080126 | 7/2007 |
| WO | WO 2007/080127 | 7/2007 |
| WO | WO 2007/091277 | 8/2007 |
| WO | WO 2007/093836 | 8/2007 |
| WO | WO 2007/098042 | 8/2007 |
| WO | WO 2007/103567 | 9/2007 |
| WO | WO 2007/107302 | 9/2007 |
| WO | WO 2007/107326 | 9/2007 |
| WO | WO 2007/140256 | 12/2007 |
| WO | WO 2007/142840 | 12/2007 |
| WO | WO 2008/002872 | 1/2008 |
| WO | WO 2008/037436 | 4/2008 |
| WO | WO 2008/054747 | 5/2008 |
| WO | WO 2008/112019 | 9/2008 |
| WO | WO 2008/114282 | 9/2008 |
| WO | WO 2008/122406 | 10/2008 |
| WO | WO 2008/124495 | 10/2008 |
| WO | WO 2008/148559 | 12/2008 |
| WO | WO 2008/150473 | 12/2008 |
| WO | WO 2008/151780 | 12/2008 |
| WO | WO 2009/006297 | 1/2009 |
| WO | WO 2009/064652 | 5/2009 |
| WO | WO 2009/100188 | 8/2009 |
| WO | WO 2009/102873 | 8/2009 |
| WO | WO 2009/103049 | 8/2009 |
| WO | WO 2009/111263 | 9/2009 |
| WO | WO 2009/144079 | 12/2009 |
| WO | WO 2010/024976 | 3/2010 |
| WO | WO 2010/037016 | 4/2010 |
| WO | WO 2010/076212 | 7/2010 |
| WO | WO 2010/077816 | 7/2010 |
| WO | WO 2010/079430 | 7/2010 |
| WO | WO 2010/080829 | 7/2010 |
| WO | WO 2010/117735 | 10/2010 |
| WO | WO 2010/117737 | 10/2010 |
| WO | WO 2011/022469 | 2/2011 |
| WO | WO 2011/034704 | 3/2011 |
| WO | WO 2011/035874 | 3/2011 |
| WO | WO 2011/062904 | 5/2011 |
| WO | WO 2011/064736 | 6/2011 |
| WO | WO 2011/064750 | 6/2011 |
| WO | WO 2011/064751 | 6/2011 |
| WO | WO 2011/066360 | 6/2011 |
| WO | WO 2011/066384 | 6/2011 |
| WO | WO 2011/072246 | 6/2011 |
| WO | WO 2011/075593 | 6/2011 |
| WO | WO 2011/075595 | 6/2011 |
| WO | WO 2011/084621 | 7/2011 |
| WO | WO 2011/084632 | 7/2011 |
| WO | WO 2011/146121 | 11/2011 |
| WO | WO 2011/154158 | 12/2011 |
| WO | WO 2011/154159 | 12/2011 |

OTHER PUBLICATIONS

An, Y. et al., "Conserved Expression of the Arabidopsis ACT1 and ACT3 Actin Subclass in Organ Primordia and Mature Pollen", The Plant Cell (1996), vol. 8, pp. 15-30.

Bäumlein, H. et al., "A Novel Seed Protein Gene from Vicia faba is Developmentally Regulated in Transgenic Tobacco and Arabidopsis Plants", Mol. Gen. Genet. (1991), vol. 225, pp. 450-467.

Benfey, P. et al., "The CaMV 35S Enhancer Contains at Least Two Domains which can Confer Different Developmental and Tissue-Specific Expression Patterns", The EMBO Journal (1989) vol. 8, No. 8, pp. 2195-2202.

Brisibe, E. et al., "Cytodifferentiation and Transformation of Embryogenic Callus Lines Derived from Anther Culture of Wheat", Journal of Experimental Botany (2000), vol. 51, No. 343, pp. 187-196.

Bustos, M. et al., "Regulation of β-Glucuronidase Expression in Transgenic Tobacco Plants by an A/T-Rich, cis-Acting Sequence Found Upstream of a French Bean β-Phaseolin Gene", The Plant Cell (1989), vol. 1, pp. 839-853.

Callis, J. et al., "Introns Increase Gene Expression in Cultured Maize Cells", Genes & Development (1987), vol. 1, pp. 1183-1200.

Carrington, J. et al., "Cap-Independent Enhancement of Translation by a Plant Potyvirus 5' Nontranslated Region", Journal of Virology (1990), vol. 64, No. 4, pp. 1590-1597.

Chaboute, M. et al., "Genomic Organization and Nucleotide Sequences of Two Histone H3 and Two Histone H4 Gene of Arabidopsis Thaliana", Plant Molecular Biology (1987), vol. 8, pp. 179-191.

Chaubet-Gigot. N. et al., "Tissue-dependent Enhancement of Transgene Expression by Introns of Replacement Histone H3 genes of Aarabidpsis", Plant Molecular Biology (2001), vol. 45, pp. 17-30.

Chilton, M. et al., "Targeted Integration of T-DNA into the Tobacco Genome at Double-Stranded Breaks: New Insights on the Mechanism of T-DNA Integration", Plant Physiology (2003), vol. 133, pp. 956-965.

Christian, M. et al., "Targeting DNA Double-Strand Breaks with TAL Effector Nucleases", Genetics (2010), vol. 186, pp. 757-761.

Civardi, L. et al., "The Relationship Between Genetic and Physical Distances in the Cloned a1-sh2 Interval of the Zea Mays L. Genome", Proc. Natl. Acad. Sci. USA (1994), vol. 91, pp. 8268-8272.

Clancy, M. et al., "Splicing of the Maize Sh1 First Intron is Essential for Enhancement of Gene Expression, and a T-Rich Motif Increases Expression without Affecting Splicing", Plant Physiology (2002), vol. 130, pp. 918-929.

Colleaux, L. et al., "Recognition and Cleavage Site of the Intron-Encoded Omega Transposase", Proc. Natl. Acad. Sci. USA (1988), vol. 85, pp. 6022-6026.

Comai, L., "An Altered aroA Gene Product Confers Resistance to the Herbicide Glyphosate", (1983), Science, vol. 221, pp. 370-371.

Crickmore, N. et al., "Revision of the Nomenclature for the Bacillus Thuringiensis Pesticidal Crystal Proteins", Microbiology and Molecular Biology Reviews (1998), vol. 62, No. 3, pp. 807-813.

Crickmore, N. et al., "The Bacillus Toxin Nomenclature", (2005), available online at: http://www.lifesci.susses.ac.uk/home/Neil_Crickmore/Bt/intro.html.

(56) References Cited

OTHER PUBLICATIONS

Crouch, N. et al., "A Mechanistic Rationalisation for the Substrate Specificity of Recombinant Mammalian 4-Hydroxyphenylpyruvate Dioxygenase (4-HPPD)", Tetrehedron (1997), vol. 53, No. 20, pp. 6993-7010.

Datla, R. et al., "Improved High-Level Constitutive Foreign Gene Expression in Plants Using an AMV RNA4 Untranslated Leader Sequence", Plant Science (1993), vol. 94, pp. 139-149.

Deshayes, A. et al., "Liposome-Mediated Transformation of Tobacco Mesophyll Protoplasts by an *Escherichia Coli* Plasmid", The EMBO Journal (1985), vol. 4, No. 11, pp. 2731-2737.

D'Halluin, K.et al., "Homologous Recombination: A Basis for Targeted Genome Optimization in Crop Species such as Maize", Plant Biotechnology Journal (2008), vol. 6, pp. 93-102.

Dunwell, "Transformation of Maize Using Silicon Carbide Whiskers", Methods in Molecular Biology (1999), vol. 111, pp. 375-382.

Fritze, I. et al., "The Crystal Structures of *Zea mays* and Arabidopsis 4-Hydroxyphenylpyruvate Dioxygenase", Plant Physiology (2004), vol. 134, pp. 1388-1400.

Gao H. et al., "Heritable Targeted Mutagenesis in Maize Using a Designed Endonuclease", The Plant Journal (2010), vol. 61, pp. 176-187.

Gasser et al., "Structure, Expression, and Evolution of the 5-Enolpyruvylshikimate-3-phosphate Synthase Genes of Petunia and Tomato", The Journal of Biological Chemistry (1988), vol. 263, No. 9, pp. 4280-4289.

Gelvin, S. "Viral-Mediated Plant Transformation gets a Boost", Nature Biotechnology (2005), vol. 23, No. 6, pp. 684-685.

Harpster, M. et al., "Relative Strengths of the 35S Califlower Mosaic Virus, 1', 2', and Nopaline Synthase Promoters in Transformed Tobacco Sugarbeet and Oilseed Rape Callus Tissue", Mol. Gen. Genet. (1988), vol. 212, pp. 182-190.

Holst-Jensen, A. et al., "Coherence Between Legal Requirements and Approaches for Detection of Genetically Modified Organisms (GMOs) and Their Derived Products", J. Agric Food Chem. (2006), vol. 54, pp. 2799-2809.

Holtorf, S. et al., "Comparison of Different Constitutive and Inducible Promoters for the Overexpression of Transgenes in Arabidopsis Thaliana", Plant Molecular Biology (1995), vol. 29, pp. 637-646.

Hudspeth et al., "Structure and Expression of the Maize Gene Encoding the Phosphoenolpyruvate Carboxylase Isozyme Involved in $C_4$ Photosynthesis", Plant Molecular Biology (1989), vol. 12, pp. 579-589.

Isalan, M. et al., "A Rapid, Generally Applicable Method to Engineer Zinc Fingers Illustrated by Targeting the HIV-1 Promoter", Nature Biotechnology (2001), vol. 19, pp. 656-660.

Josefsson, L. et al., "Structure of a Gene Encoding the 1.7 S Storage Protein, Napin, from Brassica Napus", The Journal of Biological Chemistry (1987), vol. 262, No. 25, pp. 12196-12201.

Kalderon, D. et al. "A Short Amino Acid Sequence Able to Specify Nuclear Location", Cell (1984), vol. 39, pp. 499-509.

Keil, M. et al., "Both Wound-inducible and Tuber-specific Expression are Mediated by the Promoter of a Single Member of the Potato Proteinase Inhibitor II Gene Family", The EMBO Journal (1989), vol. 8, No. 5, pp. 1323-1330.

Kelemen et al. "Transformation Vector Based on Promoter and Intron Sequences of a Replacement Histone H3 Gene. A Tool for High, Constitutive Gene Expression in Plants", Transgenic Research (2002), vol. 11, pp. 69-72.

Keller, B. et al., "Glycine-rich Cell Wall Proteins in Bean: Gene Structure and Association of the Protein with the Vascular System", The EMBO Journal (1988), vol. 7, No. 12, pp. 3625-3633.

Keller, B. et al., "Specific Expression of a Novel Cell Wall Hydroxyproline-rich Glycoprotein Gene in Lateral Root Initiation", Genes and Development (1989), vol. 3, pp. 1639-1646.

Kumar S. et al., "Controlling Transgene Integration in Plants", Trends in Plant Science (2001), vol. 6, No. 4, pp. 155-159.

Liu, Q. et al., "Design of Polydactyl Zinc-finger Proteins for Unique Addressing within Complex Genomes", Proc. Natl. Aca. Sci. USA (1997), vol. 94, pp. 5525-5530.

"Maize alcohol dehydrogenase promoter (ADH)" online from http://www.patentlens.net/daisy/promoters/242/g2/267.html.

Mascarenhas, D. et al., "Intron-mediated Enhancement of Heterologous Gene Expression in Maize", Plant Molecular Biology (1990), vol. 15, pp. 913-920.

Mézard, C., "Meiotic Recombination Hotspots in Plants", Biochemical Society Transactions (2006), vol. 34, No. 4, pp. 531-534.

Moellenbeck, D. et al., "Insecticidal Proteins from Bacillus Thuringiensis Protect Corn from Corn Rootworms", Nature Biotechnology (2001), vol. 19, pp. 668-672.

Norris, S. et al., "Genetic Dissection of Carotenoid Synthesis in Arabidopsis Defines Plastoquinone as an Essential Component of Phytoene Desaturation", The Plant Cell (1995), vol. 7, pp. 2139-2149.

Odell, J. et al., "Identification of DNA Sequences required for Activity of the Cauliflower Mosaic Virus 35S Promoter", Nature (1985), vol. 313, pp. 810-812.

Outchkourov, N. et al., "The Promoter-terminator of Chrysanthemum rbcS1 Directs very High Expression Levels in Plants", Planta (2003), vol. 216, pp. 1003-1012.

Peleman, J. et al "Structure and Expression Analyses of the 5-adenosylmethionine Synthetase Gene Family in Arabidopsis Thaliana", Gene (1989), vol. 84, pp. 359-369.

Puchta, H. et al., "Two Different but Related Mechanisms are used in Plants for the Repair of Genomic Double-strand Breaks by Homologous Recombination", Proc. Natl. Acad. Sci. USA (1996), vol. 93, pp. 5055-5060.

Raikhel, N., "Nuclear Targeting in Plants", Plant Physiology (1992), vol. 100, pp. 1627-1632.

Rüetschi, U. et al "Characterization of 4-hydroxyphenylpyruvate Dioxygenase", Eur. J. Biochem (1992), vol. 205, pp. 459-466.

Samac, D. et al "A Comparison of Constitutive Promoters for Expression of Transgenes in Alfafa (Medicago sativa)", Transgenic Research (2004), vol. 13, pp. 349-361.

Sanger, M. et al., "Characteristics of a Strong Promoter from Figwort Mosaic Virus: Comparison with the Analogous 35S Promoter from Cauliflower Mosaic Virus and the Regulated Mannopine Synthase Promoter", Plant Molecular Biology (1990), vol. 14, pp. 433-443.

Schnepf, H. et al "Characterization of Cry34/Cry35 Binary Insecticidal Proteins from Diverse Bacillus Thuringiensis Strain Collections", Applied Environm. Microbiol. (2005), vol. 71, No. 4, pp. 1765-1774.

Shah, D. et al., "Engineering Herbicide Tolerance in Transgenic Plants", Science (1986), vol. 233, pp. 478-481.

Shirsat, A. et al., "Sequences Responsible for the Tissue Specific Promoter Activity of a Pea Legumin Gene in Tobacco", Mol. Gen. Genet. (1989), vol. 215, pp. 326-331.

Stalberg, K. et al., "Disruption of an Overlapping E-box/ABRE Motif Abolished High Transcription of the napA Storage-protein Promoter in Transgenic Brassica Napus Seeds", Planta (1996), vol. 199, pp. 515-519.

Thompson, A. et al., "Cleavage and Recognition Pattern of a Double-strand-specific Endonuclease (I-CreI) Encoded by the Chloroplast 23S rRNA Intron of Chlamydomonas Reinhardtii", Gene (1992), vol. 119, pp. 247-251.

Tranel, P. et al., "Resistance of Weeds to ALS-inhibiting Herbicides: What Have we Learned?", Weed Science (2002), vol. 50, pp. 700-712.

GenBank Deposit of Arabidopsis Thaliana 4-hydroxyphenylpyruvate dioxygenase, Accession No. AF047834, deposited May 14, 1999.

GenBank Deposit of Coccidioides immitis T-cell reactive protein (trcP) gene exons, Accession No. L38493, deposited Nov. 30, 1995.

International Search Report for International Application No. PCT/EP2012/065867, mailed Mar. 5, 2013.

Written Opinion for International Application No. PCT/EP2012/065867, mailed Feb. 22, 2014.

\* cited by examiner

```
Met Ala Pro Lys Lys Lys Arg Lys Val His Met Asn Thr Lys Tyr Asn
1               5                   10                  15
Lys Glu Phe Leu Leu Tyr Leu Ala Gly Phe Val Asp Gly Asp Gly Ser
                20                  25                  30
Ile Ile Ala Gln Ile Lys Pro Asn Gln Ser Tyr Lys Phe Lys His Gln
                35                  40                  45
Leu Ser Leu Thr Phe Thr Val Thr Gln Lys Thr Gln Arg Arg Trp Phe
        50                  55                  60
Leu Asp Lys Leu Val Asp Glu Ile Gly Val Gly Tyr Val Tyr Asp Gln
65                  70                  75                  80
Gly Ser Val Ser His Tyr Arg Leu Ser Gln Ile Lys Pro Leu His Asn
                85                  90                  95
Phe Leu Thr Gln Leu Gln Pro Phe Leu Lys Leu Lys Gln Lys Gln Ala
                100                 105                 110
Asn Leu Val Leu Lys Ile Ile Glu Gln Leu Pro Ser Ala Lys Glu Ser
                115                 120                 125
Pro Asp Lys Phe Leu Glu Val Cys Thr Trp Val Asp Gln Ile Ala Ala
            130                 135                 140
Leu Asn Asp Ser Lys Thr Arg Lys Thr Thr Ser Glu Thr Val Arg Ala
                145                 150                 155                 160
Val Leu Asp Ser Leu Pro Gly Ser Val Gly Gly Leu Ser Pro Ser Gln
                165                 170                 175
```

Figure 2

```
Ala Ser Ser Ala Ala Ala Ser Ser Ser Ser Pro Gly Ser Gly Ile
                180                 185                 190
Ser Glu Ala Leu Arg Ala Gly Ala Thr Lys Ser Lys Glu Phe Leu Leu
            195                 200                 205
Tyr Leu Ala Gly Phe Val Asp Gly Asp Gly Ser Ile Lys Ala Ala Ile
        210                 215                 220
Lys Pro Asn Gln Ser Tyr Lys Phe Lys His Gln Leu Ser Leu Thr Phe
225                 230                 235                 240
Gln Val Thr Gln Lys Thr Gln Arg Arg Trp Phe Leu Asp Lys Leu Val
                245                 250                 255
Asp Glu Ile Gly Val Gly Tyr Val Tyr Asp Ser Gly Ser Val Ser Asp
            260                 265                 270
Tyr Gln Leu Ser Gln Ile Lys Pro Leu His Asn Phe Leu Thr Gln Leu
        275                 280                 285
Gln Pro Phe Leu Lys Leu Lys Leu Pro Ser Ala Lys Gln Ala Asn Leu Val Leu Lys
290                 295                 300
Ile Ile Glu Gln Leu Pro Ser Ala Lys Glu Ser Pro Asp Lys Phe Leu
305                 310                 315                 320
Glu Val Cys Thr Trp Val Asp Gln Ile Ala Ala Leu Asn Asp Ser Lys
                325                 330                 335
Thr Arg Lys Thr Thr Ser Glu Thr Val Arg Ala Val Leu Asp Ser Leu
                    340                 345                 350
Ser Glu Lys Lys Lys Ser Ser Pro
            355                 360
```

Figure 2 continued

SEQUENCE LISTING

<160> NUMBER OF SEQ ID NOS: 23

<210> SEQ ID NO 1
<211> LENGTH: 22
<212> TYPE: DNA
<213> ORGANISM: Artificial Sequence
<220> FEATURE:
<223> OTHER INFORMATION: GHB119

<400> SEQUENCE: 1
taaaattatt tacaagtgtt ta                                          22

<210> SEQ ID NO 2
<211> LENGTH: 22
<212> TYPE: DNA
<213> ORGANISM: Artificial Sequence
<220> FEATURE:
<223> OTHER INFORMATION: GHB119

<400> SEQUENCE: 2
taaacacttg taaataattt ta                                          22

<210> SEQ ID NO 3
<211> LENGTH: 3687
<212> TYPE: DNA
<213> ORGANISM: Artificial Sequence
<220> FEATURE:
<223> OTHER INFORMATION: GHB119

<400> SEQUENCE: 3

```
ccagtactaa aatccagatc atgcatggac ctgcaggtcg acggccgagt actgttttat      60
ttttaacagg aatttgagtc acgcaattc taatacttgt tcaaattgat ttgaaaaaaa     120
aaattgaata actcaaataa tgcaattcaa ttaacttgaa attcgaacaa ttttttattt    180
ttatttttta aattgaatca agttttactt acccgtaatt atttgaatgg atcaagttga    240
gttaaattca acctttttt tcttttaag aattggacca taactcaact tagctcgtaa      300
atatgttgta accgttgagc catcagtgta atattaacta ccttgtttgt aactcctaca    360
caagtcgtat agtctattag cggttgcttt gagtaattct atgtttagat gtcatatatc    420
gtattatatt attcgagttt tagtgtgatt aatgaatata aatacttgtc aacgtagata    480
tactaaattt ttttaggatt ttatgtattc gggagtcata tatatatatc atattttcat    540
atttacgaat gagttgaata cgagtttcga atacatattt aaaagaataa ataaaatgtt    600
ggtaacatag ggtggtggg ctttgataat gggctaatgg caatggattt gcacatacac     660
ccctaaccac cttcattttg gttgattttt taaatatttt ttcttgtgtg ctgaataaat    720
aaataaataa ataaaacgaa tcgaatccat gtgtttggac tatctaaaaa atgaaacttt    780
aacttaatgg aattctattt ttttttattt tatgattaat ttaaattttt ataatataga    840
aataagtttt ttatatttaa aataattaaa ataacttaaa attttatat aaaaagtatt     900
tttttcaaaa ataccatttt taaaaagtta ttaatggttt tttatttact ttgaaaaatt    960
attttagaaa aaaatttcaa atttatttt aataatttta ttattataca ttctcattat    1020
atctgttatt tttaacacaa tacttaaaat catctatagt ccctctttaa ctgcgtttca   1080
acgcactcga actcacattc tcctatatta acgataatgc catactaatc aaattaagac   1140
ttagtcgaca aaaatacttt taaactttac cattatgaat gaatccaaaa atatatccat   1200
taaaaaaaat tcaacatgct acatgattgt ttgagatttg acttagtttg tttttggacc   1260
ttaacaatca atcatatcta taactatatc tttatttaga atttaaaggg tttgttttga   1320
tgacacctaa gcatagatat aaaatataat ttaaagtact gaagttgaga atttactttt   1380
aaaggcttt cagaaaaaaa taaaaaaata aaggattgga ttattagaca acaatgcaat    1440
gttattaaat taagtatcgg gacgattgag tcttaattag attagtatta gtgttgttat   1500
cagtgtgaaa tgatgtgggt tcgagtatgc tttagagcat tatcctccta tttaaggatt   1560
aggaaggggt tatgggtagt tttagatatt gtatccaaaa tagcaaatga tattgatgtt   1620
caaaaaaaaa attaaaagtt tgggattaaa tttagaagat tatttgtata aattaaaata   1680
caaaactttt tttttatcat aattaagggg tatatatcaa aattatatat aaattatgat   1740
ttaatattca atttgatata cgaactttga ttttatacaa tttaatacat aaatattaaa   1800
tttagctcaa ttttcacaaa taattaacat cgtactcgat gtagcatcat tttaggaaaa   1860
aaattatata cctaacatga atttttatttg attgatttag ttttaaaat atttacaatt   1920
aaatcaaaat caaaattata tatatataat tgaaacaaaa ttatagtttc tacattaggc   1980
aaatcattta taaatattt tgtgttatat tttcgtgtt taaatgata taaaattata     2040
caaaaacaat attaaatgtt aataaatttgt ttaatatgaa ttttgagagc actattttta   2100
tgccgtgcct aattaaaatt atttacaagt gtttatgttg atattttaat tatgtttcat   2160
ataaatttgt cgtaatagtt taattgttaa atctaaataa aagtatttaa aaatagatat   2220
tatattttt atgatatata taaatatcat gaaactttag aatttatgga caaaaacatc    2280
```

```
actatccact agttaatcat ttctacaaac gacatttatt tatttaaaat ggtcagaaaa    2340
attgtgacct accaggaatg aggatttgat tggagggatg taaaccaagt tgatattttt    2400
ttctcacttg tgaaaaagat agtgtttggc tggaatttta tgtatgataa atttgatagg    2460
gacttgcact tgagattatt ttctgggttc ttcatgcttt tataataact tgactatcaa    2520
attctctctt tggattctac gacgttcata tctatttgta tggtggcttc gagtaggaat    2580
ttttttaaaa gtatttgtgt ttgatattta catatgtttt tatacaatgt ttagaactac    2640
ttatagtcca tttcatccct taagtaggta cgccttccta cattgacaac aatatcgata    2700
ctaatcgaac taaaactcaa tcaacgccca tattcgacac ttcaatttgg ataataagta    2760
gagtatttta tagatatttg atttatatgt aaatgatttt tttaatattt tttgagagta    2820
ttttaaaatt cgtgttttat taattttcat attatttaga ttcttaggat tgaaaaaaaa    2880
tttataaatt tgaaaaactc tctcgtggaa aagaattaca aaataattta accoctaata    2940 aaaatataac aaccattttt ttatgtcaat cactacgtta ttcatcgcat cattacttaa    3000
cgtatcatca aagatttgat gtaaaaatta aattcaaggg ctcaagccat gagagcttca    3060
atgaaaatat tcattgctaa cttttgattg aaattttaat tgaatataat ttttctcttgt    3120 gagcttaacg gatattttaa attaccttac aaaaactgtt taaaacttaa aactgtataa    3180
taataaaact tatattctct aacaacatat aaatctataa tttgtagttt gtcccctaaa    3240
cttgtccaac aatatcaaat taatgtctga atttttttatc gagttggtac gtctattcta    3300
acaccttaat ttatgctgat gcgacactac cagccaatca aatatgacac ataataaccct    3360 tcaatatgag atgtgatcaa ttaagaagtt tagaaatctt tagaaattat gatttatatt    3420
cccatcatcc ccacaaccat atcttacctc ttaaaaatat gctttctaaa aatatgattt    3480
gatttgctgt gtgaaaaaaa aaaggcaaaa gaaaatatct aagaaataaa tcaataattg    3540
agagaggtca aaagacgata ttatcctttt gatttgctgg tctctagaaa gcaaaagatg    3600
ggggattagg gtaggcagaa taaaaaaaaa aatctaggga aagaagatcc cactttaacc    3660
aatgaacgac agcccacctc attagag                                       3687
```

<210> SEQ ID NO 4
<211> LENGTH: 1635
<212> TYPE: DNA
<213> ORGANISM: Artificial Sequence
<220> FEATURE:
<223> OTHER INFORMATION: flanking region

<400> SEQUENCE: 4

```
ttttaaatca aaatccgcca aactgctgtc gtctcattgg atattacgat aatatcatta     60
atttaatttt gaagtatttt ttgttttctt aaatgtaacg agtaacacaa ttaaaatata    120
aatataaata taatacaaat ggactaaaaa tgggtataat ccgaactaac aggattaaaa    180
ctcacatgat aaaatttgga aacctatacg tataattgcc tataataagt ctcgaactaa    240
ccctccaaat attggtatta tccctttggaa tgtattgtaa cctcacacta ccctaaacat    300
atcataaggt tgtattctat ctcttttatt cagaaaataa aaacaaattc ttatatatca    360
acatcaaatg ttggagacac gtaaattttt aataataaaa attaataaaa atttaacag    420 aaataattaa tttactcttt aatttaacat acaaaaatta attttctcga aaatataatc    480
tatttcttaa attgcgtgtt cattcatcaa ttcttttctt caaggtatct cttactcaaa    540
cgtgtaaagg gctaaaagca actaaaatag ctcataagta caaatgaatc ttggatgtac    600
attgtacagt agaccggtct acggcctggt ggcctggcct cgattaaatg ggctcattgt    660
```

```
tctggagtta ggtttagacc caaatttta attaaataaa ttttgttttt taattaattt      720
ataaaataaa taaataatag cgtgaaatta aatttcggtt ttttaaaatt ttataaataa      780
taaaatgagt tatttttagg ggtgagtatt ttatcaaatc gaatgaaaaa tatttgattt      840
agttcagtta atgagtcata ttttatcatc ttaactcgtt ttaaatattt tccaaatcaa      900
gtcgagtcaa ataaatttat tcaagtcaaa ttaaaaaata ataaactgg  tcatattgaa      960 atcttgttga cgatacgact aaaattcaag ttaaaaaaac gcaaatatca tatatatttg     1020 aacactttt  aaaagaaaat aggaaaaaat atatggtaat tagtatgata aacttatctt     1080
aataatttat ttgttcaaga catcatataa tttagcattt ttatatattt taaatatttt     1140
aaaaaataat ttaatttta atatatttta taagaaaatt tgaaaaatat tttataaaac     1200
taacgagtaa aaatgatcca aagagtattt acatcaattt attattctaa ttgaattta     1260 caattcgaat taaactccaa aaaattgaat tgcttattgt aaaattgaac gtcaataatg     1320
acaatgaatc gcaaagcaag agagaaaaat aaaacacaca aaattttacg tggaaaccct     1380
ttcgagaaaa aatcacaggc agagggaaga aaattctcca tgtcaaattc gaatgataca     1440
agataagaga cgattacgtc tatttataag tttaaaaacc ttattctaat caaagtcaaa     1500
tagaagtgat gcagtaagat taaaaacttt gtgcagcctt cgccctaaca gatcccccta     1560
tcttgctaaa tggctccatg gcgatcgctc tagaggatct gcgatctagt aacatagatg     1620
acaccgcgcg cgata                                                      1635

<210> SEQ ID NO 5
<211> LENGTH: 5000
<212> TYPE: DNA
<213> ORGANISM: Artificial Sequence
<220> FEATURE:
<223> OTHER INFORMATION: BAY-5/6 expression vector
<220> FEATURE:
<221> NAME/KEY: CDS
<222> LOCATION: (3090)..(4169)

<400> SEQUENCE: 5
gacgaaaggg cctcgtgata cgcctatttt tataggttaa tgtcatgata ataatggttt       60
cttagacgtc aggtggcact tttcggggaa atgtgcgcgg aaccccctatt tgtttatttt      120 tctaaataca ttcaaatatg tatccgctca tgagacaata accctgataa atgcttcaat      180
aatattgaaa aaggaagagt atgagtattc aacatttccg tgtcgccctt attcccttt       240 ttgcggcatt ttgccttcct gttttgctc  acccagaaac gctggtgaaa gtaaaagatg      300
ctgaagatca gttgggtgca cgagtgggtt acatcgaact ggatctcaac agcggtaaga      360
tccttgagag ttttcgcccc gaagaacgtt ttccaatgat gagcactttt aaagttctgc      420
tatgtggcgc ggtattatcc cgtattgacg ccgggcaaga gcaactcggt cgccgcatac      480
actattctca gaatgacttg gttgagtact caccagtcac agaaaagcat cttacggatg      540
gcatgacagt aagagaatta tgcagtgctg ccataaccat gagtgataac actgcggcca      600
acttacttct gacaacgatc ggaggaccga aggagctaac cgcttttttg cacaacatgg      660
gggatcatgt aactcgcctt gatcgttggg aaccggagct gaatgaagcc ataccaaacg      720
acgagcgtga caccacgatg cctgtagcaa tggcaacaac gttgcgcaaa ctattaactg      780
gcgaactact tactctagct tcccggcaac aattaataga ctggatggag gcggataaag      840
ttgcaggacc acttctgcgc tcggcccttc cggctggctg gttattgct  gataaatctg      900 gagccggtga gcgtgggtct cgcggtatca ttgcagcact ggggccagat ggtaagccct      960
```

```
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc attttttaatt taaaaggatc taggtgaaga   1140 tccttttga taatctcatg accaaaatcc cttaacgtga gttttcgttc cactgagcgt    1200
cagaccccgt agaaaagatc aaaggatctt cttgagatcc ttttttttctg cgcgtaatct  1260 gctgcttgca aacaaaaaaa ccaccgctac cagcggtggt ttgtttgccg gatcaagagc   1320
taccaactct tttccgaag gtaactggct tcagcagagc gcagatacca aatactgttc     1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
gggggcggag cctatggaaa aacgccagca acgcggcctt tttacggttc ctggccttt    1860 gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgccaagctt gagaggcggt ttgcgtattg gctagagcag cttgccaaca   2280
tggtggagca cgacactctc gtctactcca agaatatcaa agatacagtc tcagaagacc   2340
aaagggctat tgagactttt caacaaaggg taatatcggg aaacctcctc ggattccatt   2400
gcccagctat ctgtcacttc atcaaaagga cagtagaaaa ggaaggtggc acctacaaat   2460
gccatcattg cgataaagga aaggctatcg ttcaagatgc ctctgccgac agtggtccca   2520
aagatggacc cccacccacg aggagcatcg tggaaaaaga agacgttcca accacgtctt   2580
caaagcaagt ggattgatgt gaacatggtg gagcacgaca ctctcgtcta ctccaagaat   2640
atcaaagata cagtctcaga agaccaaagg ctattgaga cttttcaaca aagggtaata    2700
tcgggaaacc tcctcggatt ccattgccca gctatctgtc acttcatcaa aggacagta    2760 gaaaaggaag gtggcaccta caaatgccat cattgcgata aaggaaaggc tatcgttcaa   2820
gatgcctctg ccgacagtgg tcccaaagat ggaccccac ccacgaggag catcgtggaa    2880
aaagaagacg ttccaaccac gtcttcaaag caagtggatt gatgtgatat ctccactgac   2940
gtaagggatg acgcacaatc ccactatcct tcgcaagacc cttcctctat ataaggaagt   3000
tcatttcatt tggagaggac acgctgaaat caccagtctc tctctacaaa tctatctctc   3060
tcgagctttc gcagatctgt cgaaccacc atg gca ccg aag aag aag cgc aag    3113
                                  Met Ala Pro Lys Lys Lys Arg Lys
                                   1               5 gtg cat atg aac acc aag tac aac aag gag ttc ctg ctc tac ctg gcg    3161
Val His Met Asn Thr Lys Tyr Asn Lys Glu Phe Leu Leu Tyr Leu Ala
 10              15                  20
```

| | | |
|---|---|---|
| ggc ttc gtg gac ggg gac ggc tcc atc atc gcc cag atc aag ccg aac<br>Gly Phe Val Asp Gly Asp Gly Ser Ile Ile Ala Gln Ile Lys Pro Asn<br>25                              30                              35                             40 | | 3209 |
| cag tcc tac aag ttc aag cat cag ctg tcc ctc acc ttc acc gtc acc<br>Gln Ser Tyr Lys Phe Lys His Gln Leu Ser Leu Thr Phe Thr Val Thr<br>                              45                              50                              55 | | 3257 |
| cag aag aca cag cgc cgt tgg ttc ctc gac aag ctg gtg gac gag atc<br>Gln Lys Thr Gln Arg Arg Trp Phe Leu Asp Lys Leu Val Asp Glu Ile<br>                60                              65                              70 | | 3305 |
| gga gtg ggc tac gtg tac gac cag ggc agc gtc tcc cac tac cgc ctg<br>Gly Val Gly Tyr Val Tyr Asp Gln Gly Ser Val Ser His Tyr Arg Leu<br>            75                              80                              85 | | 3353 |
| tcc cag atc aag cct ctg cac aac ttc ctg acc cag ctc cag ccc ttc<br>Ser Gln Ile Lys Pro Leu His Asn Phe Leu Thr Gln Leu Gln Pro Phe<br>      90                              95                              100 | | 3401 |
| ctg aag ctc aag cag aag cag gcc aac ctc gtg ctg aag atc atc gag<br>Leu Lys Leu Lys Gln Lys Gln Ala Asn Leu Val Leu Lys Ile Ile Glu<br>105                              110                             115                            120 | | 3449 |
| cag ctg ccc tcc gcc aag gaa tcc ccg gac aag ttc ctg gag gtg tgc<br>Gln Leu Pro Ser Ala Lys Glu Ser Pro Asp Lys Phe Leu Glu Val Cys<br>                              125                              130                            135 | | 3497 |
| acg tgg gtg gac cag atc gcg gcc ctc aac gac agc aag acc cgc aag<br>Thr Trp Val Asp Gln Ile Ala Ala Leu Asn Asp Ser Lys Thr Arg Lys<br>            140                              145                              150 | | 3545 |
| acg acc tcg gag acg gtg cgg gcg gtc ctg gac tcc ctc cca gga tcc<br>Thr Thr Ser Glu Thr Val Arg Ala Val Leu Asp Ser Leu Pro Gly Ser<br>                              155                              160                            165 | | 3593 |
| gtg gga ggt cta tcg cca tct cag gca tcc agc gcc gca tcc tcg gct<br>Val Gly Gly Leu Ser Pro Ser Gln Ala Ser Ser Ala Ala Ser Ser Ala<br>170                              175                             180 | | 3641 |
| tcc tca agc ccg ggt tca ggg atc tcc gaa gca ctc aga gct gga gca<br>Ser Ser Ser Pro Gly Ser Gly Ile Ser Glu Ala Leu Arg Ala Gly Ala<br>185                              190                             195                            200 | | 3689 |
| act aag tcc aag gaa ttc ctg ctc tac ctg gcg ggc ttc gtc gac ggg<br>Thr Lys Ser Lys Glu Phe Leu Leu Tyr Leu Ala Gly Phe Val Asp Gly<br>                              205                              210                            215 | | 3737 |
| gac ggc tcc atc aag gcc gcg atc aag ccg aac cag tcc tac aag ttc<br>Asp Gly Ser Ile Lys Ala Ala Ile Lys Pro Asn Gln Ser Tyr Lys Phe<br>            220                              225                              230 | | 3785 |
| aag cat cag ctg tcc ctc acc ttc cag gtc acg cag aag aca cag cgc<br>Lys His Gln Leu Ser Leu Thr Phe Gln Val Thr Gln Lys Thr Gln Arg<br>                235                              240                              245 | | 3833 |
| cgt tgg ttc ctc gac aag ctg gtg gac gag atc ggg gtg ggc tac gtg<br>Arg Trp Phe Leu Asp Lys Leu Val Asp Glu Ile Gly Val Gly Tyr Val<br>250                              255                             260 | | 3881 |
| tac gac tcc ggc agc gtc tcc gac tac cag ctg tcc cag atc aag cct<br>Tyr Asp Ser Gly Ser Val Ser Asp Tyr Gln Leu Ser Gln Ile Lys Pro<br>265                              270                             275                            280 | | 3929 |
| ctg cac aac ttc ctg acc cag ctc cag ccc ttc ctg aag ctc aag cag<br>Leu His Asn Phe Leu Thr Gln Leu Gln Pro Phe Leu Lys Leu Lys Gln<br>                              285                              290                            295 | | 3977 |
| aag cag gcc aac ctc gtg ctg aag atc atc gag cag ctg ccc tcc gcc<br>Lys Gln Ala Asn Leu Val Leu Lys Ile Ile Glu Gln Leu Pro Ser Ala<br>            300                              305                              310 | | 4025 |
| aag gaa tcc ccg gac aag ttc ctg gag gtg tgc acc tgg gtg gac cag<br>Lys Glu Ser Pro Asp Lys Phe Leu Glu Val Cys Thr Trp Val Asp Gln<br>                315                              320                            325 | | 4073 |
| atc gcc gct ctg aac gac tcc aag acc cgc aag acc act tcc gag acc<br>Ile Ala Ala Leu Asn Asp Ser Lys Thr Arg Lys Thr Thr Ser Glu Thr<br>330                              335                             340 | | 4121 |

-continued

```
gtc cgc gcc gtt cta gac agt ctc tcc gag aag aag aag tcg tcc ccc     4169
Val Arg Ala Val Leu Asp Ser Leu Ser Glu Lys Lys Lys Ser Ser Pro
345                 350                 355                 360 tagcatgccg ttcaaacatt tggcaataaa gtttcttaag attgaatcct gttgccggtc    4229
ttgcgatgat tatcatataa tttctgttga attacgttaa gcatgtaata attaacatgt    4289
aatgcatgac gttatttatg agatgggttt ttatgattag agtcccgcaa ttatacattt    4349
aatacgcgat agaaaacaaa atatagcgcg caaactagga taaattatcg cgcgcggtgt    4409
catctatgtt actagatcgg gcccgggaat aaaatatctt tattttcatt acatctgtgt    4469
gttggttttt tgtgtgaatc gatagtacta acatacgctc tccatcaaaa caaaacgaaa    4529
caaaacaaac tagcaaaata ggctgtcccc agtgcaagtg caggtgccag aacatttcgg    4589
taccgagctc gaattcactg gccgtcgttt tacaacgtcg tgactgggaa accctggcg     4649 ttacccaact taatcgcctt gcagcacatc cccctttcgc cagctggcgt aatagcgaag    4709
aggcccgcac cgatcgccct tcccaacagt tgcgcagcct gaatggcgaa tggcgcctga    4769
tgcggtattt tctccttacg catctgtgcg gtatttcaca ccgcatatgg tgcactctca    4829
gtacaatctg ctctgatgcc gcatagttaa gccagccccg acaccgcca acacccgctg     4889 acgcgccctg acgggcttgt ctgctcccgg catccgctta cagacaagct gtgaccgtct    4949 ccggagctg catgtgtcag aggttttcac cgtcatcacc gaaacgcgcg a              5000
```

<210> SEQ ID NO 6
<211> LENGTH: 360
<212> TYPE: PRT
<213> ORGANISM: Artificial Sequence
<220> FEATURE:
<223> OTHER INFORMATION: Synthetic Construct

<400> SEQUENCE: 6

```
Met Ala Pro Lys Lys Arg Lys Val His Met Asn Thr Lys Tyr Asn
1               5                   10                  15

Lys Glu Phe Leu Leu Tyr Leu Ala Gly Phe Val Asp Gly Asp Gly Ser
                20                  25                  30

Ile Ile Ala Gln Ile Lys Pro Asn Gln Ser Tyr Lys Phe Lys His Gln
            35                  40                  45

Leu Ser Leu Thr Phe Thr Val Thr Gln Lys Thr Gln Arg Arg Trp Phe
        50                  55                  60

Leu Asp Lys Leu Val Asp Glu Ile Gly Val Gly Tyr Val Tyr Asp Gln
    65                  70                  75                  80

Gly Ser Val Ser His Tyr Arg Leu Ser Gln Ile Lys Pro Leu His Asn
                    85                  90                  95

Phe Leu Thr Gln Leu Gln Pro Phe Leu Lys Leu Lys Gln Lys Gln Ala
                100                 105                 110

Asn Leu Val Leu Lys Ile Ile Glu Gln Leu Pro Ser Ala Lys Glu Ser
            115                 120                 125

Pro Asp Lys Phe Leu Glu Val Cys Thr Trp Val Asp Gln Ile Ala Ala
        130                 135                 140

Leu Asn Asp Ser Lys Thr Arg Lys Thr Thr Ser Glu Thr Val Arg Ala
145                 150                 155                 160

Val Leu Asp Ser Leu Pro Gly Ser Val Gly Gly Leu Ser Pro Ser Gln
                    165                 170                 175

Ala Ser Ser Ala Ala Ser Ser Ala Ser Ser Ser Pro Gly Ser Gly Ile
                180                 185                 190
```

```
Ser Glu Ala Leu Arg Ala Gly Ala Thr Lys Ser Lys Glu Phe Leu Leu
        195                 200                 205

Tyr Leu Ala Gly Phe Val Asp Gly Asp Gly Ser Ile Lys Ala Ala Ile
    210                 215                 220

Lys Pro Asn Gln Ser Tyr Lys Phe Lys His Gln Leu Ser Leu Thr Phe
225                 230                 235                 240

Gln Val Thr Gln Lys Thr Gln Arg Arg Trp Phe Leu Asp Lys Leu Val
            245                 250                 255

Asp Glu Ile Gly Val Gly Tyr Val Tyr Asp Ser Gly Ser Val Ser Asp
                260                 265                 270

Tyr Gln Leu Ser Gln Ile Lys Pro Leu His Asn Phe Leu Thr Gln Leu
        275                 280                 285

Gln Pro Phe Leu Lys Leu Lys Gln Lys Gln Ala Asn Leu Val Leu Lys
    290                 295                 300

Ile Ile Glu Gln Leu Pro Ser Ala Lys Glu Ser Pro Asp Lys Phe Leu
305                 310                 315                 320

Glu Val Cys Thr Trp Val Asp Gln Ile Ala Ala Leu Asn Asp Ser Lys
            325                 330                 335

Thr Arg Lys Thr Thr Ser Glu Thr Val Arg Ala Val Leu Asp Ser Leu
                340                 345                 350

Ser Glu Lys Lys Lys Ser Ser Pro
        355                 360

<210> SEQ ID NO 7
<211> LENGTH: 13220
<212> TYPE: DNA
<213> ORGANISM: Artificial Sequence
<220> FEATURE:
<223> OTHER INFORMATION: repair DNA vector
<220> FEATURE:
<221> NAME/KEY: CDS
<222> LOCATION: (5214)..(6290)
<220> FEATURE:
<221> NAME/KEY: CDS
<222> LOCATION: (8867)..(10204)

<400> SEQUENCE: 7
gtggcacttt tcggggaaat gtgcgcggaa cccctatttg tttattttc taaatacatt      60 caaatatgta tccgctcatg agacaataac cctgataaat gcttcaataa tattgaaaaa     120
ggaagagtat gagtattcaa catttccgtg tcgcccttat tcccttttt gcggcatttt     180 gccttcctgt ttttgctcac ccagaaacgc tggtgaaagt aaaagatgct gaagatcagt     240
tgggtgcacg agtgggttac atcgaactgg atctcaacag cggtaagatc ttgagagtt     300 ttcgccccga agaacgtttt ccaatgatga gcacttttaa agttctgcta tgtggcgcgg     360
tattatcccg tattgacgcc gggcaagagc aactcggtcg ccgcatacac tattctcaga     420
atgacttggt tgagtactca ccagtcacag aaaagcatct tacggatggc atgacagtaa     480
gagaattatg cagtgctgcc ataaccatga gtgataacac tgcggccaac ttacttctga     540
caacgatcgg aggaccgaag gagctaaccg cttttttgca acatggggg gatcatgtaa     600 ctcgccttga tcgttgggaa ccggagctga atgaagccat accaaacgac gagcgtgaca     660
ccacgatgcc tgtagcaatg gcaacaacgt tgcgcaaact attaactggc gaactactta     720
ctctagcttc ccggcaacaa ttaatagact ggatggaggc ggataaagtt gcaggaccac     780
ttctgcgctc ggcccttccg gctggctggt ttattgctga taaatctgga gccggtgagc     840
gtggatctcg cggtatcatt gcagcactgg ggccagatgg taagccctcc cgtatcgtag     900
```

```
ttatctacac gacggggagt caggcaacta tggatgaacg aaatagacag atcgctgaga      960
taggtgcctc actgattaag cattggtaac tgtcagacca agtttactca tatatacttt     1020
agattgattt aaaacttcat ttttaattta aaaggatcta ggtgaagatc cttttttgata    1080
atctcatgac caaaatccct taacgtgagt tttcgttcca ctgagcgtca gaccccgtag     1140
aaaagatcaa aggatcttct tgagatcctt ttttttctgcg cgtaatctgc tgcttgcaaa    1200
caaaaaaacc accgctacca gcggtggttt gtttgccgga tcaagagcta ccaactcttt    1260
ttccgaaggt aactggcttc agcagagcgc agataccaaa tactgtcctt ctagtgtagc     1320
cgtagttagg ccaccacttc aagaactctg tagcaccgcc tacatacctc gctctgctaa    1380
tcctgttacc agtggctgct gccagtggcg ataagtcgtg tcttaccggg ttggactcaa    1440
gacgatagtt accggataag gcgcagcggt cgggctgaac ggggggttcg tgcacacagc    1500
ccagcttgga gcgaacgacc tacaccgaac tgagatacct acagcgtgag ctatgagaaa    1560
gcgccacgct tcccgaaggg agaaaggcgg acaggtatcc ggtaagcggc agggtcggaa    1620
caggagagcg cacgagggag cttccagggg gaaacgcctg gtatctttat agtcctgtcg    1680
ggtttcgcca cctctgactt gagcgtcgat ttttgtgatg ctcgtcaggg gggcggagcc    1740
tatgaaaaaa cgccagcaac gcggcctttt tacggttcct ggccttttgc tggccttttg    1800
ctcacatgtt ctttcctgcg ttatcccctg attctgtgga taaccgtatt accgcctttg    1860
agtgagctga taccgctcgc cgcagccgaa cgaccgagcg cagcgagtca gtgagcgagg    1920
aagcggaaga gcgcccaata cgcaaaccgc ctctccccgc gcgttggccg attcattaat    1980
gcagctggca cgacaggttt cccgactgga aagcgggcag tgagcgcaac gcaattaatg    2040
tgagttagct cactcattag gcaccccagg ctttacactt tatgcttccg gctcgtatgt    2100
tgtgtggaat tgtgagcgga taacaatttc acacaggaaa cagctatgac catgattacg    2160
ccaagcgcgc aattaaccct cactaaaggg aacaaaagct ggagcttgca agcttcacgt    2220
gatatcccat cggaggaaga tctttaatta attttatttt taacaggaat ttgagtcacg    2280
caatttctaa tacttgttca aattgatttg aaaaaaaaaa ttgaataact caaataatgc    2340
aattcaatta acttgaaatt cgaacaattt tttatttta tttttaat tgaatcaagt        2400
tttacttacc cgtaattatt tgaatggatc aagttgagtt aaattcaacc ttttttttct    2460
ttttaagaat tggaccataa ctcaacttag ctcgtaaata tgttgtaacc gttgagccat    2520
cagtgtaata ttaactacct tgtttgtaac tcctacacaa gtcgtatagt ctattagcgg    2580
ttgcttgag taattctatg tttagatgtc atatatcgta ttatattatt cgagttttag     2640
tgtgattaat gaatataaat acttgtcaac gtagatatac taaattttt taggatttta    2700
tgtattcggg agtcatatat atatatcata ttttcatatt tacgaatgag ttgaatacga    2760
gtttcgaata catatttaaa agaataaata aaatgttggt aacatagggt tggtgggctt    2820
tgataatggg ctaatggcaa tggatttgca catacacccc taaccacctt catttggtt    2880
gattttttaa atatttttttc ttgtgtgctg aataaataaa taaataaata aaacgaatcg    2940
aatccatgtg tttggactat ctaaaaaatg aaactttaac ttaatggaat tctatttttt    3000
tttatttat gattaattta aattttata atatagaaat aagttttta tatttaaaat     3060
aattaaaata acttaaaatt tttatataaa aagtattttt ttcaaaaaat accatttaa    3120
aaagttatta atggttttt atttactttg aaaattatt ttagaaaaaa atttcaaatt     3180
tattttaat aattttatta ttatacattc tcattatatc tgttatttt aacacaatac     3240
ttaaaatcat ctatagtccc tctttaactg cgtttcaacg cactcgaact cacattctcc    3300
```

```
tatattaacg ataatgccat actaatcaaa ttaagactta gtcgacaaaa atacttttaa   3360
actttaccat tatgaatgaa tccaaaaata tatccattaa aaaaaattca acatgctaca   3420
tgattgtttg agatttgact tagtttgttt ttggaccttg acaatcaatc atatctataa   3480
ctatatcttt atttagaatt taaagggttt gttttgatga cacctaagca tagatataaa   3540
atataattta aagtactgaa gttgagaatt tacttttaaa ggcttttcag aaaaaaataa   3600
aaaaataaag gattggatta ttagacaaca atgcaatgtt attaaattaa gtatcgggac   3660
gattgagtct taattagatt agtattagtg ttgttatcag tgtgaaatga tgtgggttcg   3720
agtatgcttt agagcattat cctcctattt aaggattagg aagggggttat gggtagtttt   3780
agatattgta tccaaaatag caaatgatat tgatgttcaa aaaaaaaatt aaaagtttgg   3840
gattaaattt agaagattat ttgtataaat taaaatacaa acttttttt ttatcataat    3900
taagggtat atatcaaaat tatatataaa ttatgattta atattcaatt tgatatacga    3960
actttgattt tatacaattt aatacataaa tattaaattt agctcaattt tcacaaataa   4020
ttaacatcgt actcgatgta gcatcatttt aggaaaaaaa ttatatacct aacatgaatt   4080
ttatttgatt gatttagttt ttaaaatatt tacaattaaa tcaaaatcaa aattatatat   4140
atataattga aacaaaatta tagtttctac attaggcaaa tcatttataa atattttgt    4200
gttatatttt acgtgtttaa aatgatataa aattatacaa aaacaatatt aaatgttaat   4260
aatttgttta atatgaattt tgagagcact atttttatgc cgtgcctaat taaaattatt   4320
tacgcgatcg ctacgtacct gcagggcggc cgcaacatgg tggagcacga cactctcgtc   4380
tactccaaga atatcaaaga tacagtctca gaagaccaaa gggctattga acttttcaa    4440
caaagggtaa tatcgggaaa cctcctcgga ttccattgcc cagctatctg tcacttcatc   4500
aaaaggacag tagaaaagga aggtggcacc tacaaatgcc atcattgcga taaggaaag    4560
gctatcgttc aagatgcccc tgccgacagt ggtcccaaag atggacccccc acccacgagg   4620
agcatcgtgg aaaaagaaga cgttccaacc acgtcttcaa agcaagtgga ttgatgtgat   4680
atctccactg acgtaaggga tgacgcacaa tcccactatc cttcgcaaga cccttcctct   4740
atataaggaa gttcatttca tttggagagg actcgagctc atttctctat tacttcagcc   4800
ataacaaaag aactctttc tcttcttatt aaaccaaaac catggctagt atttcatctt     4860
cagttgccac tgtttcacgt accgcaccag cccaagctaa tatggtggct ccgttcacag   4920
gtcttaagtc aaatgctgca tttccaacca ctaagaaggc taatgacttc tcaacacttc   4980
cgagcaacgg tgggagagta cagtatatgc aagtctggcc agcctatggc aacaagaagt   5040
ttgagacctt atcctactta cctccgctat ctatggctcc cactgtgatg atggccagct   5100
ctgccacagc tgtggcacca tttcaagggt tgaagagtac tgctagtttg ccagttgctc   5160
ggagatcttc cagatcgctg gggaatgtta gcaacggagg taggattaga tgc atg     5216
                                                            Met
                                                             1
gct gat cta tac gag aat cct atg gga ctc atg ggt ttc gag ttc att    5264
Ala Asp Leu Tyr Glu Asn Pro Met Gly Leu Met Gly Phe Glu Phe Ile
         5                  10                 15
gag ttt gct tct cct aca cct ggg acc ctt gaa ccc atc ttt gag att    5312
Glu Phe Ala Ser Pro Thr Pro Gly Thr Leu Glu Pro Ile Phe Glu Ile
         20                 25                 30
atg ggg ttt act aag gta gct aca cat cgc agt aag aac gtg cac cta    5360
Met Gly Phe Thr Lys Val Ala Thr His Arg Ser Lys Asn Val His Leu
         35                 40                 45
```

```
tat cgg caa gga gag att aac ctg atc ttg aac aac gaa cct aac tct      5408
Tyr Arg Gln Gly Glu Ile Asn Leu Ile Leu Asn Asn Glu Pro Asn Ser
 50                  55                  60                  65 ata gca agc tac ttt gct gcc gaa cat gga cca tcc gtt tgt ggc atg      5456
Ile Ala Ser Tyr Phe Ala Ala Glu His Gly Pro Ser Val Cys Gly Met
                 70                  75                  80 gca ttt cga gtt aag gat tcc cag aaa gcc tac aat agg gca tta gaa      5504
Ala Phe Arg Val Lys Asp Ser Gln Lys Ala Tyr Asn Arg Ala Leu Glu
             85                  90                  95 ctt gga gct cag cct att cac att gac act gga cct atg gaa ttg aat      5552
Leu Gly Ala Gln Pro Ile His Ile Asp Thr Gly Pro Met Glu Leu Asn
100                 105                 110 ctt cca gcc atc aaa ggc atc ggt ggt gca ccg ttg tat ctt atc gac      5600
Leu Pro Ala Ile Lys Gly Ile Gly Gly Ala Pro Leu Tyr Leu Ile Asp
    115                 120                 125 aga ttc gga gag ggc agt tct atc tac gac ata gat ttc gtc tat ctt      5648
Arg Phe Gly Glu Gly Ser Ser Ile Tyr Asp Ile Asp Phe Val Tyr Leu
130                 135                 140                 145 gaa ggc gtg gaa cga aat cct gtc ggt gct ggc ttg aag gtt att gat      5696
Glu Gly Val Glu Arg Asn Pro Val Gly Ala Gly Leu Lys Val Ile Asp
                150                 155                 160 cat ttg aca cac aac gtc tat cgt gga cga atg gta tac tgg gct aac      5744
His Leu Thr His Asn Val Tyr Arg Gly Arg Met Val Tyr Trp Ala Asn
            165                 170                 175 ttc tat gag aaa ctc ttc aac ttt agg gaa gct aga tac ttt gac atc      5792
Phe Tyr Glu Lys Leu Phe Asn Phe Arg Glu Ala Arg Tyr Phe Asp Ile
        180                 185                 190 aaa gga gag tat act ggt ctc aca tca aag gct atg agc gct cca gat      5840
Lys Gly Glu Tyr Thr Gly Leu Thr Ser Lys Ala Met Ser Ala Pro Asp
    195                 200                 205 ggt atg ata agg att cca ctc aac gaa gag tca agc aaa ggt gca gga      5888
Gly Met Ile Arg Ile Pro Leu Asn Glu Glu Ser Ser Lys Gly Ala Gly
210                 215                 220                 225 caa atc gaa gag ttt ctt atg cag ttc aat ggt gaa ggc att cag cat      5936
Gln Ile Glu Glu Phe Leu Met Gln Phe Asn Gly Glu Gly Ile Gln His
                230                 235                 240 gtc gct ttt ctg act gat gat ctt gtg aaa acc tgg gat gca ttg aag      5984
Val Ala Phe Leu Thr Asp Asp Leu Val Lys Thr Trp Asp Ala Leu Lys
            245                 250                 255 aag ata ggt atg aga ttc atg act gca cct ccc gat act tac tat gag      6032
Lys Ile Gly Met Arg Phe Met Thr Ala Pro Pro Asp Thr Tyr Tyr Glu
        260                 265                 270 atg cta gaa gga cgc ctg cct gat cat ggg gaa ccc gtg gac caa ctg      6080
Met Leu Glu Gly Arg Leu Pro Asp His Gly Glu Pro Val Asp Gln Leu
275                 280                 285 caa gcc agg ggt ata ctt ctc gat ggt tct tcg gtt gag ggt gat aag      6128
Gln Ala Arg Gly Ile Leu Leu Asp Gly Ser Ser Val Glu Gly Asp Lys
290                 295                 300                 305 agg ctc ctg tta caa atc ttt tcc gag act ctc atg gga ccc gtt ttc      6176
Arg Leu Leu Leu Gln Ile Phe Ser Glu Thr Leu Met Gly Pro Val Phe
                310                 315                 320 ttt gag ttc att cag cgt aaa ggg gac gat ggc ttc gga gaa tgg aac      6224
Phe Glu Phe Ile Gln Arg Lys Gly Asp Asp Gly Phe Gly Glu Trp Asn
            325                 330                 335 ttc aaa gca ctt ttc gaa tcg ata gag agg gat caa gtt cgt aga ggg      6272
Phe Lys Ala Leu Phe Glu Ser Ile Glu Arg Asp Gln Val Arg Arg Gly
        340                 345                 350 gtt ttg acc gct gat taa aagctagcac gcgtggcgcg ccccgatcc              6320
Val Leu Thr Ala Asp
        355
```

```
gcgtttgtgt ttctgggtt tctcacttaa gcgtctgcgt tttacttttg tattgggttt    6380
ggcgtttagt agtttgcggt agcgttcttg ttatgtgtaa ttacgctttt tcttcttgct    6440
tcagcagttt cggttgaaat ataaatcgaa tcaagtttca ctttatcagc gttgttttaa    6500
attttggcat taaattggtg aaaattgctt caattttgta tctaaataga agagacaaca    6560
tgaaattcga cttttgacct caaatcttcg aacatttatt tcctgatttc acgatggatg    6620
aggataacga aagggcggtt cctatgtccg ggaaagttcc cgtagaagac aatgagcaaa    6680
gctactgaaa cgcggacacg acgtcgcatt ggtacggata tgagttaaac cgactcaatt    6740
cctttattaa gacataaacc gattttggtt aaagtgtaac agtgagctga tataaaaccg    6800
aaacaaaccg gtacaagttt gattgagcaa cttgatgaca aacttcagaa ttttggttat    6860
tgaatgaaaa tcatagtcta atcgtaaaaa atgtacagaa gaaagctag agcagaacaa    6920 agattctata ttctggttcc aatttatcat cgctttaacg tccctcagat ttgatcgggg    6980
aattcgatat cattaccctg ttatccctaa agcttattaa tataacttcg tatagcatac    7040
attatacgaa gttatgtttg tcgaggagaa atatgagtcg aggcatggat acactaagtt    7100
cccctgaagt gagcatgatc tttgatgctg agatgattcc cagagcaaga tagtttgtgc    7160
tgcaagtgac acaattgtaa tgaaaccacc actcaacgaa tttacttgtg gctttgacat    7220
gtcgtgtgct ctgtttgtat ttgtgagtgc cggttggtaa ttattttgt taatgtgatt    7280 ttaaaacctc ttatgtaaat agttacttta tctattgaag tgtgttcttg tggtctatag    7340
tttctcaaag ggaaattaaa atgttgacat cccatttaca attgataact tggtatacac    7400
aaactttgta aatttggtga tatttatggt cgaaagaagg caatacccat tgtatgttcc    7460
aatatcaata tcaatacgat aacttgataa tactaacata tgattgtcat tgtttttcca    7520
gtatcaatat acattaagct actacaaaat tagtataaat cactatatta taaatctttt    7580
tcggttgtaa cttgtaattc gtgggtttt aaaataaaag catgtgaaaa ttttcaaata    7640
atgtgatggc gcaattttat tttccgagtt ccaaaatatt gccgcttcat taccctaatt    7700
tgtggcgcca catgtaaaac aaaagacgat tcttagtggc tatcactgcc atcacgcgga    7760
tcactaatat gaaccgtcga ttaaaacaga tcgacggttt atacatcatt ttattgtaca    7820
cacggatcga tatctcagcc gttagattta atatgcgatc tgattgctca aaaaatagac    7880
tctccgtctt tgcctataaa aacaatttca catctttctc acccaaatct actcttaacc    7940
gttcttcttc ttctacagac atcaatttct ctcgactcta gaggatccaa gcttatcgat    8000
ttcgaacccc tcaggcgaag aacaggtatg atttgtttgt aattagatca ggggtttagg    8060
tctttccatt acttttaat gttttttctg ttactgtctc cgcgatctga ttttacgaca    8120
atagagtttc gggttttgtc ccattccagt ttgaaaataa aggtccgtct tttaagtttg    8180
ctggatcgat aaacctgtga agattgagtc tagtcgattt attggatgat ccattcttca    8240 tcgtttttt cttgcttcga agttctgtat aaccagattt gtctgtgtgc gattgtcatt    8300
acctagccgt gtatcgagaa ctagggtttt cgagtcaatt ttgccccttt tggttatatc    8360
tggttcgata acgattcatc tggattaggg ttttaagtgg tgacgtttag tattccaatt    8420
tcttcaaaat ttagttatgg ataatgaaaa tccccaattg actgttcaat ttcttgttaa    8480
atgcgcagat cacaatggct tcgatctcct cctcagtcgc gaccgttagc cggaccgccc    8540
ctgctcaggc caacatggtg gctccgttca ccggccttaa gtccaacgcc gccttcccca    8600
ccaccaagaa ggctaacgac ttctccaccc ttcccagcaa cggtggaaga gttcaatgta    8660
```

-continued

```
tgcaggtgtg gccggcctac ggcaacaaga agttcgagac gctgtcgtac ctgccgccgc    8720
tgtctatggc gcccaccgtg atgatggcct cgtcggccac cgccgtcgct ccgttccagg    8780
ggctcaagtc caccgccagc ctccccgtcg cccgccgctc ctccagaagc ctcggcaacg    8840
tcagcaacgg cggaaggatc cggtgc atg gcc ggc gcc gag gag atc gtg ctg    8893
                              Met Ala Gly Ala Glu Glu Ile Val Leu
                                  360                 365 cag ccc atc aag gag atc tcc ggc acc gtc aag ctg ccg ggg tcc aag    8941
Gln Pro Ile Lys Glu Ile Ser Gly Thr Val Lys Leu Pro Gly Ser Lys
        370                 375                 380 tcg ctt tcc aac cgg atc ctc cta ctc gcc gcc ctg tcc gag ggg aca    8989
Ser Leu Ser Asn Arg Ile Leu Leu Leu Ala Ala Leu Ser Glu Gly Thr
385                 390                 395 aca gtg gtt gat aac ctg ctg aac agt gag gat gtc cac tac atg ctc    9037
Thr Val Val Asp Asn Leu Leu Asn Ser Glu Asp Val His Tyr Met Leu
400                 405                 410                 415 ggg gcc ttg agg act ctt ggt ctc tct gtc gaa gcg gac aaa gct gcc    9085
Gly Ala Leu Arg Thr Leu Gly Leu Ser Val Glu Ala Asp Lys Ala Ala
                420                 425                 430 aaa aga gct gta gtt gtt ggc tgt ggt gga aag ttc cca gtt gag gat    9133
Lys Arg Ala Val Val Val Gly Cys Gly Gly Lys Phe Pro Val Glu Asp
            435                 440                 445 gct aaa gag gaa gtg cag ctc ttc ttg ggg aat gct gga atc gca atg    9181
Ala Lys Glu Glu Val Gln Leu Phe Leu Gly Asn Ala Gly Ile Ala Met
        450                 455                 460 cgg tcc ttg aca gca gct gtt act gct gct ggt gga aat gca act tac    9229
Arg Ser Leu Thr Ala Ala Val Thr Ala Ala Gly Gly Asn Ala Thr Tyr
465                 470                 475 gtg ctt gat gga gta cca aga atg agg gag aga ccc att ggc gac ttg    9277
Val Leu Asp Gly Val Pro Arg Met Arg Glu Arg Pro Ile Gly Asp Leu
480                 485                 490                 495 gtt gtc gga ttg aag cag ctt ggt gca gat gtt gat tgt ttc ctt ggc    9325
Val Val Gly Leu Lys Gln Leu Gly Ala Asp Val Asp Cys Phe Leu Gly
                500                 505                 510 act gac tgc cca cct gtt cgt gtc aat gga atc gga ggg cta cct ggt    9373
Thr Asp Cys Pro Pro Val Arg Val Asn Gly Ile Gly Gly Leu Pro Gly
            515                 520                 525 ggc aag gtc aag ctg tct ggc tcc atc agc agt cag tac ttg agt gcc    9421
Gly Lys Val Lys Leu Ser Gly Ser Ile Ser Ser Gln Tyr Leu Ser Ala
        530                 535                 540 ttg ctg atg gct gct cct ttg gct ctt ggg gat gtg gag att gaa atc    9469
Leu Leu Met Ala Ala Pro Leu Ala Leu Gly Asp Val Glu Ile Glu Ile
545                 550                 555 att gat aaa tta atc tcc att ccg tac gtc gaa atg aca ttg aga ttg    9517
Ile Asp Lys Leu Ile Ser Ile Pro Tyr Val Glu Met Thr Leu Arg Leu
560                 565                 570                 575 atg gag cgt ttt ggt gtg aaa gca gag cat tct gat agc tgg gac aga    9565
Met Glu Arg Phe Gly Val Lys Ala Glu His Ser Asp Ser Trp Asp Arg
                580                 585                 590 ttc tac att aag gga ggt caa aaa tac aag tcc cct aaa aat gcc tat    9613
Phe Tyr Ile Lys Gly Gly Gln Lys Tyr Lys Ser Pro Lys Asn Ala Tyr
            595                 600                 605 gtt gaa ggt gat gcc tca agc gca agc tat ttc ttg gct ggt gct gca    9661
Val Glu Gly Asp Ala Ser Ser Ala Ser Tyr Phe Leu Ala Gly Ala Ala
        610                 615                 620 att act gga ggg act gtg act gtg gaa ggt tgt ggc acc acc agt ttg    9709
Ile Thr Gly Gly Thr Val Thr Val Glu Gly Cys Gly Thr Thr Ser Leu
625                 630                 635 cag ggt gat gtg aag ttt gct gag gta ctg gag atg atg gga gcg aag    9757
```

| | | | | | | | | | | | | |
|---|---|---|---|---|---|---|---|---|---|---|---|---|
| Gln | Gly | Asp | Val | Lys | Phe | Ala | Glu | Val | Leu | Glu | Met | Met | Gly | Ala | Lys |
| 640 | | | | 645 | | | | | 650 | | | | | 655 | |

| gtt | aca | tgg | acc | gag | act | agc | gta | act | gtt | act | ggc | cca | ccg | cgg | gag | 9805 |
|---|---|---|---|---|---|---|---|---|---|---|---|---|---|---|---|---|
| Val | Thr | Trp | Thr | Glu | Thr | Ser | Val | Thr | Val | Thr | Gly | Pro | Pro | Arg | Glu | |
| | | | | 660 | | | | | 665 | | | | | 670 | | |

| cca | ttt | ggg | agg | aaa | cac | ctc | aag | gcg | att | gat | gtc | aac | atg | aac | aag | 9853 |
|---|---|---|---|---|---|---|---|---|---|---|---|---|---|---|---|---|
| Pro | Phe | Gly | Arg | Lys | His | Leu | Lys | Ala | Ile | Asp | Val | Asn | Met | Asn | Lys | |
| | | | 675 | | | | | 680 | | | | | 685 | | | |

| atg | cct | gat | gtc | gcc | atg | act | ctt | gct | gtg | gtt | gcc | ctc | ttt | gcc | gat | 9901 |
|---|---|---|---|---|---|---|---|---|---|---|---|---|---|---|---|---|
| Met | Pro | Asp | Val | Ala | Met | Thr | Leu | Ala | Val | Val | Ala | Leu | Phe | Ala | Asp | |
| | | 690 | | | | | 695 | | | | | 700 | | | | |

| ggc | ccg | aca | gcc | atc | aga | gac | gtg | gct | tcc | tgg | aga | gta | aag | gag | acc | 9949 |
|---|---|---|---|---|---|---|---|---|---|---|---|---|---|---|---|---|
| Gly | Pro | Thr | Ala | Ile | Arg | Asp | Val | Ala | Ser | Trp | Arg | Val | Lys | Glu | Thr | |
| 705 | | | | | 710 | | | | | 715 | | | | | | |

| gag | agg | atg | gtt | gcg | atc | cgg | acg | gag | cta | acc | aag | ctg | gga | gca | tct | 9997 |
|---|---|---|---|---|---|---|---|---|---|---|---|---|---|---|---|---|
| Glu | Arg | Met | Val | Ala | Ile | Arg | Thr | Glu | Leu | Thr | Lys | Leu | Gly | Ala | Ser | |
| 720 | | | | 725 | | | | | 730 | | | | | 735 | | |

| gtt | gag | gaa | ggg | ccg | gac | tac | tgc | atc | atc | acg | ccg | gag | aag | ctg | | 10045 |
|---|---|---|---|---|---|---|---|---|---|---|---|---|---|---|---|---|
| Val | Glu | Glu | Gly | Pro | Asp | Tyr | Cys | Ile | Ile | Thr | Pro | Pro | Glu | Lys | Leu | |
| | | | 740 | | | | | 745 | | | | | 750 | | | |

| aac | gtg | acg | gcg | atc | gac | acg | tac | gac | gac | cac | agg | atg | gcg | atg | gct | 10093 |
|---|---|---|---|---|---|---|---|---|---|---|---|---|---|---|---|---|
| Asn | Val | Thr | Ala | Ile | Asp | Thr | Tyr | Asp | Asp | His | Arg | Met | Ala | Met | Ala | |
| | | | 755 | | | | | 760 | | | | | 765 | | | |

| ttc | tcc | ctt | gcc | gcc | tgt | gcc | gag | gtc | ccc | gtc | acc | atc | cgg | gac | cct | 10141 |
|---|---|---|---|---|---|---|---|---|---|---|---|---|---|---|---|---|
| Phe | Ser | Leu | Ala | Ala | Cys | Ala | Glu | Val | Pro | Val | Thr | Ile | Arg | Asp | Pro | |
| | | 770 | | | | | 775 | | | | | 780 | | | | |

| ggg | tgc | acc | cgg | aag | acc | ttc | ccc | gac | tac | ttc | gat | gtg | ctg | agc | act | 10189 |
|---|---|---|---|---|---|---|---|---|---|---|---|---|---|---|---|---|
| Gly | Cys | Thr | Arg | Lys | Thr | Phe | Pro | Asp | Tyr | Phe | Asp | Val | Leu | Ser | Thr | |
| 785 | | | | | 790 | | | | | 795 | | | | | | |

| ttc | gtc | aag | aat | taa | gctctagaac | tagtggatcc | cccgatccgc | gtttgtgttt | | 10244 |
|---|---|---|---|---|---|---|---|---|---|---|
| Phe | Val | Lys | Asn | | | | | | | |
| 800 | | | | | | | | | | |

| | |
|---|---|
| tctgggtttc tcacttaagc gtctgcgttt tactttgta ttgggtttgg cgtttagtag | 10304 |
| tttgcggtag cgttcttgtt atgtgtaatt acgctttttc ttcttgcttc agcagtttcg | 10364 |
| gttgaaatat aaatcgaatc aagtttcact ttatcagcgt tgttttaaat tttggcatta | 10424 |
| aattggtgaa aattgcttca attttgtatc taaatagaag agacaacatg aaattcgact | 10484 |
| tttgacctca aatcttcgaa catttatttc ctgatttcac gatggatgag gataacgaaa | 10544 |
| gggcggttcc tatgtccggg aaagttcccg tagaagacaa tgagcaaagc tactgaaacg | 10604 |
| cggacacgac gtcgcattgg tacggatatg agttaaaccg actcaattcc tttattaaga | 10664 |
| cataaaccga ttttggttaa agtgtaacag tgagctgata taaaaccgaa acaaaccggt | 10724 |
| acaagtttga ttgagcaact tgatgacaaa cttcagaatt ttggttattg aatgaaaatc | 10784 |
| atagtctaat cgtaaaaaat gtacagaaga aaagctagag cagaacaaag attctatatt | 10844 |
| ctggttccaa tttatcatcg ctttaacgtc cctcagattt gatcgggaaa cataacttcg | 10904 |
| tatagcatac attatacgaa gttatcaaaa cgtcgtgaga cagtttggtt aacttacaag | 10964 |
| tgtttatgtt gatattttaa ttatgtttca tataaatttg tcgtaatagt ttaattgtta | 11024 |
| aatctaaata aaagtattta aaatagata ttatatttt tatgatatat ataaatatca | 11084 |
| tgaaacttta gaatttatgg acaaaaacat cactatccac tagttaatca tttctacaaa | 11144 |
| cgacatttat ttatttaaaa tggtcagaaa aattgtgacc taccaggaat gaggatttga | 11204 |
| ttggagggat gtaaaccaag ttgatatttt tttctcactt gtgaaaaaga tagtgtttgg | 11264 |
| ctggaatttt atgtatgata aatttgatag ggacttgcac ttgagattat tttctgggtt | 11324 |

-continued

```
cttcatgctt ttataataac ttgactatca aattctctct ttggattcta cgacgttcat    11384
atctatttgt atggtggctt cgagtaggaa ttttttaaa agtatttgtg tttgatattt     11444
acatatgttt ttatacaatg tttagaacta cttatagtcc atttcatccc ttaagtaggt    11504
acgccttcct acattgacaa caatatcgat actaatcgaa ctaaaactca atcaacgccc    11564
atattcgaca cttcaatttg gataataagt agagtatttt atagatattt gatttatatg    11624
taaatgattt ttttaatatt ttttgagagt attttaaaat tcgtgttttta ttaattttca   11684
tattatttag attcttagga ttgaaaaaaa atttataaat ttgaaaaact ctctcgtgga    11744
aaagaattac aaaataattt aaccctaat aaaaatataa caaccatttt tttatgtcaa     11804
tcactacgtt attcatcgca tcattactta acgtatcatc aaagatttga tgtaaaaatt    11864
aaattcaagg gctcaagcca tgagagcttc aatgaaaata ttcattgcta acttttgatt    11924
gaaattttaa ttgaatataa ttttttcttg tgagcttaac ggatattta aattaccta     11984
caaaaactgt ttaaaactta aaactgtata ataataaaac ttatattctc taacaacata    12044
taaatctata atttgtagtt tgtcccctaa acttgtccaa caatatcaaa ttaatgtctg    12104
aattttttat cgagttggta cgtctattct aacaccttaa tttatgctga tgcgacacta    12164
ccagccaatc aaatatgaca cataataacc ttcaatatga gatgtgatca attaagaagt    12224
ttagaaatct ttagaaatta tgatttatat tcccatcatc cccacaacca tatcttacct    12284
cttaaaaata tgctttctaa aaatatgatt tgatttgctg tgtgaaaaaa aaaaggcaaa    12344
agaaaatatc taagaaataa atcaataatt gagagaggtc aaaagacgat attatccttt    12404
tgatttgctg gtctctagaa agcaaaagat ggggattag ggtaggcaga ataaaaaaa    12464
aaatctaggg aagaagatc ccactttaac caatgaacga cagcccacct cattagagcc     12524
taggatccag attccaaggg aagcttggcc ttgacggccg tacccaattc gccctatagt    12584
gagtcgtatt acgcgcgctc actggccgtc gttttacaac gtcgtgactg ggaaaaccct    12644
ggcgttaccc aacttaatcg ccttgcagca catcccccctt tcgccagctg gcgtaatagc    12704
gaagaggccc gcaccgatcg cccttcccaa cagttgcgca gcctgaatgg cgaatgggac    12764
gcgccctgta gcggcgcatt aagcgcggcg ggtgtggtgg ttacgcgcag cgtgaccgct    12824
acacttgcca gcgccctagc gcccgctcct ttcgctttct tcccttcctt tctcgccacg    12884
ttcgccggct ttccccgtca gctctaaat cgggggctcc ctttagggtt ccgatttagt     12944
gctttacggc acctcgaccc caaaaaactt gattagggtg atggttcacg tagtgggcca    13004
tcgccctgat agacggtttt tcgccctttg acgttggagt ccacgttctt taatagtgga    13064
ctcttgttcc aaactggaac aacactcaac cctatctcgg tctattcttt tgatttataa    13124
gggattttgc cgatttcggc ctattggtta aaaaatgagc tgatttaaca aaaatttaac    13184
gcgaatttta acaaaatatt aacgcttaca atttag                              13220
```

<210> SEQ ID NO 8
<211> LENGTH: 358
<212> TYPE: PRT
<213> ORGANISM: Artificial Sequence
<220> FEATURE:
<223> OTHER INFORMATION: Synthetic Construct

<400> SEQUENCE: 8

```
Met Ala Asp Leu Tyr Glu Asn Pro Met Gly Leu Met Gly Phe Glu Phe
 1               5                  10                  15

Ile Glu Phe Ala Ser Pro Thr Pro Gly Thr Leu Glu Pro Ile Phe Glu
            20                  25                  30
```

Ile Met Gly Phe Thr Lys Val Ala Thr His Arg Ser Lys Asn Val His
            35                  40                  45

Leu Tyr Arg Gln Gly Glu Ile Asn Leu Ile Leu Asn Asn Glu Pro Asn
 50                  55                  60

Ser Ile Ala Ser Tyr Phe Ala Ala Glu His Gly Pro Ser Val Cys Gly
 65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
            115                 120                 125

Asp Arg Phe Gly Glu Gly Ser Ser Ile Tyr Asp Ile Asp Phe Val Tyr
            130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Tyr Phe Asp
            180                 185                 190

Ile Lys Gly Glu Tyr Thr Gly Leu Thr Ser Lys Ala Met Ser Ala Pro
            195                 200                 205

Asp Gly Met Ile Arg Ile Pro Leu Asn Glu Glu Ser Ser Lys Gly Ala
            210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
            275                 280                 285

Leu Gln Ala Arg Gly Ile Leu Leu Asp Gly Ser Ser Val Glu Gly Asp
            290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Trp
                325                 330                 335

Asn Phe Lys Ala Leu Phe Glu Ser Ile Glu Arg Asp Gln Val Arg Arg
            340                 345                 350

Gly Val Leu Thr Ala Asp
            355

<210> SEQ ID NO 9
<211> LENGTH: 445
<212> TYPE: PRT
<213> ORGANISM: Artificial Sequence
<220> FEATURE:
<223> OTHER INFORMATION: Synthetic Construct

<400> SEQUENCE: 9

Met Ala Gly Ala Glu Glu Ile Val Leu Gln Pro Ile Lys Glu Ile Ser
1               5                   10                  15

Gly Thr Val Lys Leu Pro Gly Ser Lys Ser Leu Ser Asn Arg Ile Leu
            20                  25                  30

-continued

```
Leu Leu Ala Ala Leu Ser Glu Gly Thr Thr Val Val Asp Asn Leu Leu
         35                  40                  45
Asn Ser Glu Asp Val His Tyr Met Leu Gly Ala Leu Arg Thr Leu Gly
 50                  55                  60
Leu Ser Val Glu Ala Asp Lys Ala Ala Lys Arg Ala Val Val Val Gly
 65                  70                  75                  80
Cys Gly Gly Lys Phe Pro Val Glu Asp Ala Lys Glu Glu Val Gln Leu
                 85                  90                  95
Phe Leu Gly Asn Ala Gly Ile Ala Met Arg Ser Leu Thr Ala Ala Val
                100                 105                 110
Thr Ala Ala Gly Gly Asn Ala Thr Tyr Val Leu Asp Gly Val Pro Arg
                115                 120                 125
Met Arg Glu Arg Pro Ile Gly Asp Leu Val Val Gly Leu Lys Gln Leu
            130                 135                 140
Gly Ala Asp Val Asp Cys Phe Leu Gly Thr Asp Cys Pro Pro Val Arg
145                 150                 155                 160
Val Asn Gly Ile Gly Gly Leu Pro Gly Gly Lys Val Lys Leu Ser Gly
                    165                 170                 175
Ser Ile Ser Ser Gln Tyr Leu Ser Ala Leu Leu Met Ala Ala Pro Leu
                180                 185                 190
Ala Leu Gly Asp Val Glu Ile Glu Ile Ile Asp Lys Leu Ile Ser Ile
                195                 200                 205
Pro Tyr Val Glu Met Thr Leu Arg Leu Met Glu Arg Phe Gly Val Lys
            210                 215                 220
Ala Glu His Ser Asp Ser Trp Asp Arg Phe Tyr Ile Lys Gly Gly Gln
225                 230                 235                 240
Lys Tyr Lys Ser Pro Lys Asn Ala Tyr Val Glu Gly Asp Ala Ser Ser
                245                 250                 255
Ala Ser Tyr Phe Leu Ala Gly Ala Ala Ile Thr Gly Gly Thr Val Thr
                260                 265                 270
Val Glu Gly Cys Gly Thr Thr Ser Leu Gln Gly Asp Val Lys Phe Ala
            275                 280                 285
Glu Val Leu Glu Met Met Gly Ala Lys Val Thr Trp Thr Glu Thr Ser
            290                 295                 300
Val Thr Val Thr Gly Pro Pro Arg Glu Pro Phe Gly Arg Lys His Leu
305                 310                 315                 320
Lys Ala Ile Asp Val Asn Met Asn Lys Met Pro Asp Val Ala Met Thr
                325                 330                 335
Leu Ala Val Val Ala Leu Phe Ala Asp Gly Pro Thr Ala Ile Arg Asp
            340                 345                 350
Val Ala Ser Trp Arg Val Lys Glu Thr Glu Arg Met Val Ala Ile Arg
            355                 360                 365
Thr Glu Leu Thr Lys Leu Gly Ala Ser Val Glu Glu Gly Pro Asp Tyr
        370                 375                 380
Cys Ile Ile Thr Pro Pro Glu Lys Leu Asn Val Thr Ala Ile Asp Thr
385                 390                 395                 400
Tyr Asp Asp His Arg Met Ala Met Ala Phe Ser Leu Ala Ala Cys Ala
                405                 410                 415
Glu Val Pro Val Thr Ile Arg Asp Pro Gly Cys Thr Arg Lys Thr Phe
            420                 425                 430
Pro Asp Tyr Phe Asp Val Leu Ser Thr Phe Val Lys Asn
            435                 440                 445
```

<210> SEQ ID NO 10
<211> LENGTH: 554
<212> TYPE: DNA
<213> ORGANISM: Artificial Sequence
<220> FEATURE:
<223> OTHER INFORMATION: probe

<400> SEQUENCE: 10

```
ttgagtctcc ttctggtact cctggtggtc ttagggctta catggtttct gttcataaca      60
ggaagaacaa catctacgct gttcatgaga acggtactat gattcatctt gctcctgagg     120
attacaccgg tttcaccatc tcccccatcc acgccaccca ggtcaataat cagaccagga     180
ccttcatctc cgagaagttc ggcaaccagg gcgactccct gaggttcgag cagtccaaca     240
ccaccgccag gtacaccctg aggggcaacg gcaactccta caacctgtac ctcagggtgt     300
cctccctcgg caactccacc atcagggtca ccatcaacgg caggtgtac accgcctcca     360
acgtgaacac caccaccaac aacgacggcg tcaacgacaa cggcgctagg ttcctggaca     420
tcaacatggg caacgtcgtg gcctccgaca acaccaacgt gccccctggac atcaacgtga     480
catttaactc cggcacccag ttcgagctga tgaacatcat gttcgtgcca actaacctcc     540
cacccatcta ctga                                                       554
```

<210> SEQ ID NO 11
<211> LENGTH: 828
<212> TYPE: DNA
<213> ORGANISM: Artificial Sequence
<220> FEATURE:
<223> OTHER INFORMATION: probe

<400> SEQUENCE: 11

```
accgaagaac catcgagaag tataccctg gcttgcagtt ggtccacggg ttccccatga       60
tcaggcaggc gtccttctag catctcatag taagtatcgg gaggtgcagt catgaatctc     120
atacctatct tcttcaatgc atcccaggtt ttcacaagat catcagtcag aaaagcgaca     180
tgctgaatgc cttcaccatt gaactgcata agaaactctt cgatttgtcc tgcacctttg     240
cttgactctt cgttgagtgg aatccttatc ataccatctg gagcgctcat agcctttgat     300
gtgagaccag tatactctcc tttgatgtca agtatctag cttccctaaa gttgaagagt     360
ttctcataga agttagccca gtataccatt cgtccacgat agacgttgtg tgtcaaatga     420
tcaataacct tcaagccagc accgacagga tttcgttcca cgccttcaag atagacgaaa     480
tctatgtcgt agatagaact gccctctccg aatctgtcga taagatacaa cggtgcacca     540
ccgatgcctt tgatggctgg aagattcaat tccataggtc cagtgtcaat gtgaataggc     600
tgagctccaa gttctaatgc cctattgtag gctttctggg aatccttaac tcgaaatgcc     660
atgccacaaa cggatggtcc atgttcggca gcaaagtagc ttgctataga gttaggttcg     720
ttgttcaaga tcaggttaat ctctccttgc cgatataggt gcacgttctt actgcgatgt     780
gtagctacct tagtaaaccc cataatctca aagatgggtt caagggtc                  828
```

<210> SEQ ID NO 12
<211> LENGTH: 745
<212> TYPE: DNA
<213> ORGANISM: Artificial Sequence
<220> FEATURE:
<223> OTHER INFORMATION: probe

<400> SEQUENCE: 12

```
cggcgtgatg atgcagtagt ccggcccttc ctcaacagat gctcccagct tggttagctc      60
```

```
cgtccggatc gcaaccatcc tctcggtctc ctttactctc caggaagcca cgtctctgat    120
ggctgtcggg ccatcggcaa agagggcaac cacagcaaga gtcatggcga catcaggcat    180
cttgttcatg ttgacatcaa tcgccttgag gtgtttcctc ccaaatggct cccgcggtgg    240
gccagtaaca gttacgctag tctcggtcca tgtaaccttc gctcccatca tctccagtac    300
ctcagcaaac ttcacatcac cctgcaaact ggtggtgcca caaccttcca cagtcacagt    360
ccctccagta attgcagcac cagccaagaa atagcttgcg cttgaggcat cacccttcaac   420 ataggcattt ttaggggact tgtattttg acctccctta atgtagaatc tgtcccagct     480
atcagaatgc tctgctttca caccaaaacg ctccatcaat ctcaatgtca tttcgacgta    540
cggaatggag attaatttat caatgatttc aatctccaca tccccaagag ccaaggagc     600 agccatcagc aaggcactca agtactgact gctgatggag ccagacagct tgaccttgcc    660
accaggtagc cctccgattc cattgacacg aacaggtggg cagtcagtgc caaggaaaca    720
atcaacatct gcaccaagct gcttc                                          745
```

```
<210> SEQ ID NO 13
<211> LENGTH: 25
<212> TYPE: DNA
<213> ORGANISM: Artificial Sequence
<220> FEATURE:
<223> OTHER INFORMATION: primer

<400> SEQUENCE: 13
tccagtacta aaatccagat catgc                                           25

<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
tgatgcgatg aataacgtag tg                                              22

<210> SEQ ID NO 15
<211> LENGTH: 20
<212> TYPE: DNA
<213> ORGANISM: Artificial Sequence
<220> FEATURE:
<223> OTHER INFORMATION: PCR primer

<400> SEQUENCE: 15
ccctggcttg cagttggtcc                                                 20

<210> SEQ ID NO 16
<211> LENGTH: 163
<212> TYPE: PRT
<213> ORGANISM: Chlamydomonas reinhardtii

<400> SEQUENCE: 16

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Thr Phe Gln Val Thr Glu Lys
        35                  40                  45

Thr Gln Arg Arg Trp Phe Leu Asp Lys Leu Val Asp Glu Ile Gly Val
```

```
            50                  55                  60
Gly Tyr Val Arg Asp Arg Gly Ser Val Ser Asp Tyr Ile Leu Ser Glu
 65                  70                  75                  80

Ile Lys Pro Leu His Asn Phe Leu Thr Gln Leu Gln Pro Phe Leu Lys
                 85                  90                  95

Leu Lys Gln Lys Gln Ala Asn Leu Val Leu Lys Ile Ile Glu Gln Leu
             100                 105                 110

Pro Ser Ala Lys Glu Ser Pro Asp Lys Phe Leu Glu Val Cys Thr Trp
         115                 120                 125

Val Asp Gln Ile Ala Ala Leu Asn Asp Ser Lys Thr Arg Lys Thr Thr
     130                 135                 140

Ser Glu Thr Val Arg Ala Val Leu Asp Ser Leu Ser Glu Lys Lys Lys
145                 150                 155                 160

Ser Ser Pro

<210> SEQ ID NO 17
<211> LENGTH: 20
<212> TYPE: DNA
<213> ORGANISM: Artificial Sequence
<220> FEATURE:
<223> OTHER INFORMATION: PCR primer

<400> SEQUENCE: 17
tataaatgcc ggcgcgtagc                                             20

<210> SEQ ID NO 18
<211> LENGTH: 20
<212> TYPE: DNA
<213> ORGANISM: Artificial Sequence
<220> FEATURE:
<223> OTHER INFORMATION: PCR primer

<400> SEQUENCE: 18
cgacagccat cagagacgtg                                             20

<210> SEQ ID NO 19
<211> LENGTH: 358
<212> TYPE: PRT
<213> ORGANISM: Pseudomonas fluorescens

<400> SEQUENCE: 19

Met Ala Asp Leu Tyr Glu Asn Pro Met Gly Leu Met Gly Phe Glu Phe
  1               5                  10                  15

Ile Glu Phe Ala Ser Pro Thr Pro Gly Thr Leu Glu Pro Ile Phe Glu
                 20                  25                  30

Ile Met Gly Phe Thr Lys Val Ala Thr His Arg Ser Lys Asn Val His
             35                  40                  45

Leu Tyr Arg Gln Gly Glu Ile Asn Leu Ile Leu Asn Asn Glu Pro Asn
 50                  55                  60

Ser Ile Ala Ser Tyr Phe Ala Ala Glu His Gly Pro Ser Val Cys Gly
 65                  70                  75                  80

Met Ala Phe Arg Val Lys Asp Ser Gln Lys Ala Tyr Asn Arg Ala Leu
                 85                  90                  95

Glu Leu Gly Ala Gln Pro Ile His Ile Asp Thr Gly Pro Met Glu Leu
             100                 105                 110

Asn Leu Pro Ala Ile Lys Gly Ile Gly Gly Ala Pro Leu Tyr Leu Ile
         115                 120                 125

Asp Arg Phe Gly Glu Gly Ser Ser Ile Tyr Asp Ile Asp Phe Val Tyr
```

```
          130                 135                 140
Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Gly
                325                 330                 335

Asn Phe Lys Ala Leu Phe Glu Ser Ile Glu Arg Asp Gln Val Arg Arg
            340                 345                 350

Gly Val Leu Thr Ala Asp
        355
```

<210> SEQ ID NO 20
<211> LENGTH: 8617
<212> TYPE: DNA
<213> ORGANISM: Artificial
<220> FEATURE:
<223> OTHER INFORMATION: vector
<220> FEATURE:
<221> NAME/KEY: CDS
<222> LOCATION: (949)..(2025)
<223> OTHER INFORMATION: hppdPfW336
<220> FEATURE:
<221> NAME/KEY: CDS
<222> LOCATION: (4602)..(5939)
<223> OTHER INFORMATION: 2mepsps

<400> SEQUENCE: 20

```
aattacaacg gtatatatcc tgccagtact gggcccctc gagggcgatc gctacgtacc      60
tgcaggcccg ggttaattaa gcggccgcaa catggtggag cacgacactc tcgtctactc    120
caagaatatc aaagatacag tctcagaaga ccaaagggct attgagactt ttcaacaaag    180
ggtaatatcg ggaaacctcc tcggattcca ttgcccagct atctgtcact tcatcaaaag    240
gacagtagaa aaggaaggtg gcacctacaa atgccatcat tgcgataaag gaaaggctat    300
cgttcaagat gcccctgccg acagtggtcc caaagatgga ccccacccca cgaggagcat    360
cgtggaaaaa gaagacgttc caaccacgtc ttcaaagcaa gtggattgat gtgatatctc    420
cactgacgta aggatgacg cacaatccca ctatccttcg caagaccctt cctctatata    480
aggaagttca tttcatttgg agaggactcg agctcatttc tctattactt cagccataac    540
```

```
aaaagaactc ttttctcttc ttattaaacc aaaaccatgg ctagtatttc atcttcagtt    600
gccactgttt cacgtaccgc accagcccaa gctaatatgg tggctccgtt cacaggtctt    660
aagtcaaatg ctgcatttcc aaccactaag aaggctaatg acttctcaac acttccgagc    720
aacggtggga gagtacagta tatgcaagtc tggccagcct atggcaacaa gaagtttgag    780
accttatcct acttacctcc gctatctatg gctcccactg tgatgatggc cagctctgcc    840
acagctgtgg caccatttca agggttgaag agtactgcta gtttgccagt tgctcggaga    900
tcttccagat cgctggggaa tgttagcaac ggaggtagga ttagatgc atg gct gat     957
                                                     Met Ala Asp
                                                      1
```

| cta tac gag aat cct atg gga ctc atg ggt ttc gag ttc att gag ttt | 1005 |
|---|---|
| Leu Tyr Glu Asn Pro Met Gly Leu Met Gly Phe Glu Phe Ile Glu Phe | |
| 5                   10                   15 | |

| gct tct cct aca cct ggg acc ctt gaa ccc atc ttt gag att atg ggg | 1053 |
|---|---|
| Ala Ser Pro Thr Pro Gly Thr Leu Glu Pro Ile Phe Glu Ile Met Gly | |
| 20                  25                  30                  35 | |

| ttt act aag gta gct aca cat cgc agt aag aac gtg cac cta tat cgg | 1101 |
|---|---|
| Phe Thr Lys Val Ala Thr His Arg Ser Lys Asn Val His Leu Tyr Arg | |
| 40                  45                  50 | |

| caa gga gag att aac ctg atc ttg aac aac gaa cct aac tct ata gca | 1149 |
|---|---|
| Gln Gly Glu Ile Asn Leu Ile Leu Asn Asn Glu Pro Asn Ser Ile Ala | |
| 55                  60                  65 | |

| agc tac ttt gct gcc gaa cat gga cca tcc gtt tgt ggc atg gca ttt | 1197 |
|---|---|
| Ser Tyr Phe Ala Ala Glu His Gly Pro Ser Val Cys Gly Met Ala Phe | |
| 70                  75                  80 | |

| cga gtt aag gat tcc cag aaa gcc tac aat agg gca tta gaa ctt gga | 1245 |
|---|---|
| Arg Val Lys Asp Ser Gln Lys Ala Tyr Asn Arg Ala Leu Glu Leu Gly | |
| 85                  90                  95 | |

| gct cag cct att cac att gac act gga cct atg gaa ttg aat ctt cca | 1293 |
|---|---|
| Ala Gln Pro Ile His Ile Asp Thr Gly Pro Met Glu Leu Asn Leu Pro | |
| 100                 105                 110                 115 | |

| gcc atc aaa ggc atc ggt ggt gca ccg ttg tat ctt atc gac aga ttc | 1341 |
|---|---|
| Ala Ile Lys Gly Ile Gly Gly Ala Pro Leu Tyr Leu Ile Asp Arg Phe | |
| 120                 125                 130 | |

| gga gag ggc agt tct atc tac gac ata gat ttc gtc tat ctt gaa ggc | 1389 |
|---|---|
| Gly Glu Gly Ser Ser Ile Tyr Asp Ile Asp Phe Val Tyr Leu Glu Gly | |
| 135                 140                 145 | |

| gtg gaa cga aat cct gtc ggt gct ggc ttg aag gtt att gat cat ttg | 1437 |
|---|---|
| Val Glu Arg Asn Pro Val Gly Ala Gly Leu Lys Val Ile Asp His Leu | |
| 150                 155                 160 | |

| aca cac aac gtc tat cgt gga cga atg gta tac tgg gct aac ttc tat | 1485 |
|---|---|
| Thr His Asn Val Tyr Arg Gly Arg Met Val Tyr Trp Ala Asn Phe Tyr | |
| 165                 170                 175 | |

| gag aaa ctc ttc aac ttt agg gaa gct aga tac ttt gac atc aaa gga | 1533 |
|---|---|
| Glu Lys Leu Phe Asn Phe Arg Glu Ala Arg Tyr Phe Asp Ile Lys Gly | |
| 180                 185                 190                 195 | |

| gag tat act ggt ctc aca tca aag gct atg agc gct cca gat ggt atg | 1581 |
|---|---|
| Glu Tyr Thr Gly Leu Thr Ser Lys Ala Met Ser Ala Pro Asp Gly Met | |
| 200                 205                 210 | |

| ata agg att cca ctc aac gaa gag tca agc aaa ggt gca gga caa atc | 1629 |
|---|---|
| Ile Arg Ile Pro Leu Asn Glu Glu Ser Ser Lys Gly Ala Gly Gln Ile | |
| 215                 220                 225 | |

| gaa gag ttt ctt atg cag ttc aat ggt gaa ggc att cag cat gtc gct | 1677 |
|---|---|
| Glu Glu Phe Leu Met Gln Phe Asn Gly Glu Gly Ile Gln His Val Ala | |
| 230                 235                 240 | |

| ttt ctg act gat gat ctt gtg aaa acc tgg gat gca ttg aag aag ata | 1725 |
|---|---|
| Phe Leu Thr Asp Asp Leu Val Lys Thr Trp Asp Ala Leu Lys Lys Ile | |

```
                        245                 250                 255
ggt atg aga ttc atg act gca cct ccc gat act tac tat gag atg cta    1773
Gly Met Arg Phe Met Thr Ala Pro Pro Asp Thr Tyr Tyr Glu Met Leu
260                 265                 270                 275 gaa gga cgc ctg cct gat cat ggg gaa ccc gtg gac caa ctg caa gcc    1821
Glu Gly Arg Leu Pro Asp His Gly Glu Pro Val Asp Gln Leu Gln Ala
                280                 285                 290 agg ggt ata ctt ctc gat ggt tct tcg gtt gag ggt gat aag agg ctc    1869
Arg Gly Ile Leu Leu Asp Gly Ser Ser Val Glu Gly Asp Lys Arg Leu
            295                 300                 305 ctg tta caa atc ttt tcc gag act ctc atg gga ccc gtt ttc ttt gag    1917
Leu Leu Gln Ile Phe Ser Glu Thr Leu Met Gly Pro Val Phe Phe Glu
        310                 315                 320 ttc att cag cgt aaa ggg gac gat ggc ttc gga gaa tgg aac ttc aaa    1965
Phe Ile Gln Arg Lys Gly Asp Asp Gly Phe Gly Glu Trp Asn Phe Lys
    325                 330                 335 gca ctt ttc gaa tcg ata gag agg gat caa gtt cgt aga ggg gtt ttg    2013
Ala Leu Phe Glu Ser Ile Glu Arg Asp Gln Val Arg Arg Gly Val Leu
340                 345                 350                 355 acc gct gat taa aagctagcac gcgtggcgcg ccccccgatcc gcgtttgtgt        2065
Thr Ala Asp tttctgggtt tctcacttaa gcgtctgcgt tttacttttg tattgggttt ggcgtttagt   2125
agtttgcggt agcgttcttg ttatgtgtaa ttacgctttt tcttcttgct tcagcagttt   2185
cggttgaaat ataaatcgaa tcaagtttca ctttatcagc gttgttttaa attttggcat   2245
taaattggtg aaaattgctt caattttgta tctaaataga agagacaaca tgaaattcga   2305
cttttgacct caaatcttcg aacatttatt tcctgatttc acgatggatg aggataacga   2365
aagggcggtt cctatgtccg ggaaagttcc cgtagaagac aatgagcaaa gctactgaaa   2425
cgcggacacg acgtcgcatt ggtacggata tgagttaaac cgactcaatt cctttattaa   2485
gacataaacc gattttggtt aaagtgtaac agtgagctga tataaaaccg aaacaaaccg   2545
gtacaagttt gattgagcaa cttgatgaca aacttcagaa ttttggttat tgaatgaaaa   2605
tcatagtcta atcgtaaaaa atgtacagaa gaaaagctag agcagaacaa agattctata   2665
ttctggttcc aatttatcat cgctttaacg tccctcagat ttgatcgggg aattcgatat   2725
cattaccctg ttatccctaa agcttattaa tataacttcg tatagcatac attatacgaa   2785
gttatgtttg tcgaggagaa atatgagtcg aggcatggat acactaagtt cccctgaagt   2845
gagcatgatc tttgatgctg agatgattcc cagagcaaga tagtttgtgc tgcaagtgac   2905
acaattgtaa tgaaaccacc actcaacgaa tttacttgtg gctttgacat gtcgtgtgct   2965
ctgtttgtat ttgtgagtgc cggttggtaa ttattttttgt taatgtgatt ttaaaacctc   3025
ttatgtaaat agttacttta tctattgaag tgtgttcttg tggtctatag tttctcaaag   3085
ggaaattaaa atgttgacat cccatttaca attgataact tggtatacac aaactttgta   3145
aatttggtga tatttatggt cgaaagaagg caatacccat tgtatgttcc aatatcaata   3205
tcaatacgat aacttgataa tactaacata tgattgtcat tgttttttcca gtatcaatat   3265 acattaagct actacaaaat tagtataaat cactatatta taaatctttt tcggttgtaa   3325
cttgtaattc gtgggttttt aaaataaaag catgtgaaaa ttttcaaata atgtgatggc   3385 gcaatttttat tttccgagtt ccaaaatatt gccgcttcat taccctaatt tgtggcgcca   3445
catgtaaaac aaaagacgat tcttagtggc tatcactgcc atcacgcgga tcactaatat   3505
gaaccgtcga ttaaaacaga tcgacggttt atacatcatt ttattgtaca cacggatcga   3565
```

```
                                            -continued tatctcagcc gttagattta atatgcgatc tgattgctca aaaaatagac tctccgtctt      3625
tgcctataaa aacaatttca catctttctc acccaaatct actcttaacc gttcttcttc      3685
ttctacagac atcaatttct ctcgactcta gaggatccaa gcttatcgat ttcgaacccc      3745
tcaggcgaag aacaggtatg atttgtttgt aattagatca gggtttagg tctttccatt      3805 acttttaat gttttttctg ttactgtctc cgcgatctga ttttacgaca atagagtttc       3865
gggttttgtc ccattccagt ttgaaaataa aggtccgtct tttaagtttg ctggatcgat      3925
aaacctgtga agattgagtc tagtcgattt attggatgat ccattcttca tcgttttttt       3985
cttgcttcga agttctgtat aaccagattt gtctgtgtgc gattgtcatt acctagccgt      4045
gtatcgagaa ctagggtttt cgagtcaatt ttgccccttt tggttatatc tggttcgata     4105
acgattcatc tggattaggg ttttaagtgg tgacgtttag tattccaatt tcttcaaaat    4165
ttagttatgg ataatgaaaa tccccaattg actgttcaat ttcttgttaa atgcgcagat    4225
cacaatggct tcgatctcct cctcagtcgc gaccgttagc cggaccgccc ctgctcaggc    4285
caacatggtg gctccgttca ccggccttaa gtccaacgcc gccttcccca ccaccaagaa    4345
ggctaacgac ttctccaccc ttcccagcaa cggtggaaga gttcaatgta tgcaggtgtg    4405
gccggcctac ggcaacaaga agttcgagac gctgtcgtac ctgccgccgc tgtctatggc    4465
gcccaccgtg atgatggcct cgtcggccac cgccgtcgct ccgttccagg ggctcaagtc    4525
caccgccagc ctccccgtcg cccgccgctc ctccagaagc ctcggcaacg tcagcaacgg    4585
```

| cggaaggatc cggtgc atg gcc ggc gcc gag gag atc gtg ctg cag ccc atc<br>                                Met Ala Gly Ala Glu Glu Ile Val Leu Gln Pro Ile<br>                                360                    365                    370 | 4637 |
|---|---|
| aag gag atc tcc ggc acc gtc aag ctg ccg ggg tcc aag tcg ctt tcc<br>Lys Glu Ile Ser Gly Thr Val Lys Leu Pro Gly Ser Lys Ser Leu Ser<br>                375                       380                       385 | 4685 |
| aac cgg atc ctc cta ctc gcc gcc ctg tcc gag ggg aca aca gtg gtt<br>Asn Arg Ile Leu Leu Leu Ala Ala Leu Ser Glu Gly Thr Thr Val Val<br>           390                     395                       400 | 4733 |
| gat aac ctg ctg aac agt gag gat gtc cac tac atg ctc ggg gcc ttg<br>Asp Asn Leu Leu Asn Ser Glu Asp Val His Tyr Met Leu Gly Ala Leu<br>    405                       410                       415 | 4781 |
| agg act ctt ggt ctc tct gtc gaa gcg gac aaa gct gcc aaa aga gct<br>Arg Thr Leu Gly Leu Ser Val Glu Ala Asp Lys Ala Ala Lys Arg Ala<br>420                       425                       430 | 4829 |
| gta gtt gtt ggc tgt ggt gga aag ttc cca gtt gag gat gct aaa gag<br>Val Val Val Gly Cys Gly Gly Lys Phe Pro Val Glu Asp Ala Lys Glu<br>435                     440                       445                   450 | 4877 |
| gaa gtg cag ctc ttc ttg ggg aat gct gga atc gca atg cgg tcc ttg<br>Glu Val Gln Leu Phe Leu Gly Asn Ala Gly Ile Ala Met Arg Ser Leu<br>                455                       460                       465 | 4925 |
| aca gca gct gtt act gct gct ggt gga aat gca act tac gtg ctt gat<br>Thr Ala Ala Val Thr Ala Ala Gly Gly Asn Ala Thr Tyr Val Leu Asp<br>           470                     475                       480 | 4973 |
| gga gta cca aga atg agg gag aga ccc att ggc gac ttg gtt gtc gga<br>Gly Val Pro Arg Met Arg Glu Arg Pro Ile Gly Asp Leu Val Val Gly<br>                485                       490                       495 | 5021 |
| ttg aag cag ctt ggt gca gat gtt gat tgt ttc ctt ggc act gac tgc<br>Leu Lys Gln Leu Gly Ala Asp Val Asp Cys Phe Leu Gly Thr Asp Cys<br>500                       505                       510 | 5069 |
| cca cct gtt cgt gtc aat gga atc gga ggg cta cct ggt ggc aag gtc<br>Pro Pro Val Arg Val Asn Gly Ile Gly Gly Leu Pro Gly Gly Lys Val<br>515                       520                       525                   530 | 5117 |
| aag ctg tct ggc tcc atc agc agt cag tac ttg agt gcc ttg ctg atg | 5165 |

|  |  |  |  |  |  |  |  |  |  |  |  |  |  |  |
|---|---|---|---|---|---|---|---|---|---|---|---|---|---|---|
| Lys | Leu | Ser | Gly | Ser | Ile | Ser | Ser | Gln | Tyr | Leu | Ser | Ala | Leu | Leu | Met |
|  |  |  |  | 535 |  |  |  | 540 |  |  |  | 545 |  |  |

| gct | gct | cct | ttg | gct | ctt | ggg | gat | gtg | gag | att | gaa | atc | att | gat | aaa | 5213 |
|---|---|---|---|---|---|---|---|---|---|---|---|---|---|---|---|---|
| Ala | Ala | Pro | Leu | Ala | Leu | Gly | Asp | Val | Glu | Ile | Glu | Ile | Ile | Asp | Lys |  |
|  |  |  | 550 |  |  |  |  | 555 |  |  |  |  | 560 |  |  |  |

| tta | atc | tcc | att | ccg | tac | gtc | gaa | atg | aca | ttg | aga | ttg | atg | gag | cgt | 5261 |
| Leu | Ile | Ser | Ile | Pro | Tyr | Val | Glu | Met | Thr | Leu | Arg | Leu | Met | Glu | Arg |
|  |  | 565 |  |  |  |  | 570 |  |  |  |  | 575 |  |  |  |

| ttt | ggt | gtg | aaa | gca | gag | cat | tct | gat | agc | tgg | gac | aga | ttc | tac | att | 5309 |
| Phe | Gly | Val | Lys | Ala | Glu | His | Ser | Asp | Ser | Trp | Asp | Arg | Phe | Tyr | Ile |
|  | 580 |  |  |  |  | 585 |  |  |  |  | 590 |  |  |  |  |

| aag | gga | ggt | caa | aaa | tac | aag | tcc | cct | aaa | aat | gcc | tat | gtt | gaa | ggt | 5357 |
| Lys | Gly | Gly | Gln | Lys | Tyr | Lys | Ser | Pro | Lys | Asn | Ala | Tyr | Val | Glu | Gly |
| 595 |  |  |  |  | 600 |  |  |  |  | 605 |  |  |  |  | 610 |

| gat | gcc | tca | agc | gca | agc | tat | ttc | ttg | gct | ggt | gct | gca | att | act | gga | 5405 |
| Asp | Ala | Ser | Ser | Ala | Ser | Tyr | Phe | Leu | Ala | Gly | Ala | Ala | Ile | Thr | Gly |
|  |  |  |  | 615 |  |  |  |  | 620 |  |  |  |  | 625 |  |

| ggg | act | gtg | act | gtg | gaa | ggt | tgt | ggc | acc | acc | agt | ttg | cag | ggt | gat | 5453 |
| Gly | Thr | Val | Thr | Val | Glu | Gly | Cys | Gly | Thr | Thr | Ser | Leu | Gln | Gly | Asp |
|  |  |  | 630 |  |  |  |  | 635 |  |  |  |  | 640 |  |  |

| gtg | aag | ttt | gct | gag | gta | ctg | gag | atg | atg | gga | gcg | aag | gtt | aca | tgg | 5501 |
| Val | Lys | Phe | Ala | Glu | Val | Leu | Glu | Met | Met | Gly | Ala | Lys | Val | Thr | Trp |
|  |  | 645 |  |  |  |  | 650 |  |  |  |  | 655 |  |  |  |

| acc | gag | act | agc | gta | act | gtt | act | ggc | cca | ccg | cgg | gag | cca | ttt | ggg | 5549 |
| Thr | Glu | Thr | Ser | Val | Thr | Val | Thr | Gly | Pro | Pro | Arg | Glu | Pro | Phe | Gly |
|  | 660 |  |  |  |  | 665 |  |  |  |  | 670 |  |  |  |  |

| agg | aaa | cac | ctc | aag | gcg | att | gat | gtc | aac | atg | aac | aag | atg | cct | gat | 5597 |
| Arg | Lys | His | Leu | Lys | Ala | Ile | Asp | Val | Asn | Met | Asn | Lys | Met | Pro | Asp |
| 675 |  |  |  | 680 |  |  |  |  | 685 |  |  |  |  | 690 |  |

| gtc | gcc | atg | act | ctt | gct | gtg | gtt | gcc | ctc | ttt | gcc | gat | ggc | ccg | aca | 5645 |
| Val | Ala | Met | Thr | Leu | Ala | Val | Val | Ala | Leu | Phe | Ala | Asp | Gly | Pro | Thr |
|  |  |  |  | 695 |  |  |  |  | 700 |  |  |  |  | 705 |  |

| gcc | atc | aga | gac | gtg | gct | tcc | tgg | aga | gta | aag | gag | acc | gag | agg | atg | 5693 |
| Ala | Ile | Arg | Asp | Val | Ala | Ser | Trp | Arg | Val | Lys | Glu | Thr | Glu | Arg | Met |
|  |  |  | 710 |  |  |  |  | 715 |  |  |  |  | 720 |  |  |

| gtt | gcg | atc | cgg | acg | gag | cta | acc | aag | ctg | gga | gca | tct | gtt | gag | gaa | 5741 |
| Val | Ala | Ile | Arg | Thr | Glu | Leu | Thr | Lys | Leu | Gly | Ala | Ser | Val | Glu | Glu |
|  |  | 725 |  |  |  |  | 730 |  |  |  |  | 735 |  |  |  |

| ggg | ccg | gac | tac | tgc | atc | atc | acg | ccg | ccg | gag | aag | ctg | aac | gtg | acg | 5789 |
| Gly | Pro | Asp | Tyr | Cys | Ile | Ile | Thr | Pro | Pro | Glu | Lys | Leu | Asn | Val | Thr |
|  | 740 |  |  |  |  | 745 |  |  |  |  | 750 |  |  |  |  |

| gcg | atc | gac | acg | tac | gac | gac | cac | agg | atg | gcg | atg | gct | ttc | tcc | ctt | 5837 |
| Ala | Ile | Asp | Thr | Tyr | Asp | Asp | His | Arg | Met | Ala | Met | Ala | Phe | Ser | Leu |
| 755 |  |  |  | 760 |  |  |  |  | 765 |  |  |  |  | 770 |  |

| gcc | gcc | tgt | gcc | gag | gtc | ccc | gtc | acc | atc | cgg | gac | cct | ggg | tgc | acc | 5885 |
| Ala | Ala | Cys | Ala | Glu | Val | Pro | Val | Thr | Ile | Arg | Asp | Pro | Gly | Cys | Thr |
|  |  |  |  | 775 |  |  |  |  | 780 |  |  |  |  | 785 |  |

| cgg | aag | acc | ttc | ccc | gac | tac | ttc | gat | gtg | ctg | agc | act | ttc | gtc | aag | 5933 |
| Arg | Lys | Thr | Phe | Pro | Asp | Tyr | Phe | Asp | Val | Leu | Ser | Thr | Phe | Val | Lys |
|  |  |  | 790 |  |  |  |  | 795 |  |  |  |  | 800 |  |  |

| aat | taa | gctctagaac | tagtggatcc | cccgatccgc | gtttgtgttt | tctgggtttc | 5989 |
| Asn |  |  |  |  |  |  |  |

| tcacttaagc | gtctgcgttt | tactttgta | ttgggtttgg | cgtttagtag | tttgcggtag | 6049 |
|---|---|---|---|---|---|---|

| cgttcttgtt | atgtgtaatt | acgctttttc | ttcttgcttc | agcagtttcg | gttgaaatat | 6109 |

| aaatcgaatc | aagtttcact | ttatcagcgt | tgtttttaaat | tttggcatta | aattggtgaa | 6169 |

| aattgcttca | attttgtatc | taaatagaag | agacaacatg | aaattcgact | tttgacctca | 6229 |

| aatcttcgaa | catttatttc | ctgatttcac | gatggatgag | gataacgaaa | gggcggttcc | 6289 |

```
tatgtccggg aaagttcccg tagaagacaa tgagcaaagc tactgaaacg cggacacgac    6349
gtcgcattgg tacggatatg agttaaaccg actcaattcc tttattaaga cataaaccga    6409
ttttggttaa agtgtaacag tgagctgata taaaaccgaa acaaaccggt acaagtttga    6469
ttgagcaact tgatgacaaa cttcagaatt ttggttattg aatgaaaatc atagtctaat    6529
cgtaaaaaat gtacagaaga aaagctagag cagaacaaag attctatatt ctggttccaa    6589
tttatcatcg ctttaacgtc cctcagattt gatcgggaaa cataacttcg tatagcatac    6649
attatacgaa gttatcaaaa cgtcgtgaga cagtttggtt aactataacg gtcctaaggt    6709
agcgatcgag gcattacggc attacggcac tcgcgagggt ccgaatctat gtcgggtgcg    6769
gagaaagagg taatgaaatg gcaatttaca attgaatata tcctgccgcc gctgccgctt    6829
tgcacccggt ggagcttgca tgttggtttc tacgcagaac tgagccggtt aggcagataa    6889
tttccattga gaactgagcc atgtgcacct tcccccaac acggtgagcg acggggcaac    6949
ggagtgatcc acatgggact tttaaacatc atccgtcgga tggcgttgcg agagaagcag    7009
tcgatccgtg agatcagccg acgcaccggg caggcgcgca acacgatcgc aaagtatttg    7069
aacgcaggta caatcgagcc gacgttcacg gtaccggaac gaccaagcaa gctagcttag    7129
taaagccctc gctagatttt aatgcggatg ttgcgattac ttcgccaact attgcgataa    7189
caagaaaaag ccagcctttc atgatatatc tcccaatttg tgtagggctt attatgcacg    7249
cttaaaaata ataaaagcag acttgacctg atagtttggc tgtgagcaat tatgtgctta    7309
gtgcatctaa cgcttgagtt aagccgcgcc gcgaagcggc gtcggcttga acgaattgtt    7369
agacattatt tgccgactac cttggtgatc tcgcctttca cgtagtggac aaattcttcc    7429
aactgatctg cgcgcgaggc caagcgatct tcttcttgtc caagataagc ctgtctagct    7489
tcaagtatga cgggctgata ctgggccggc aggcgctcca ttgcccagtc ggcagcgaca    7549
tccttcggcg cgattttgcc ggttactgcg ctgtaccaaa tgcgggacaa cgtaagcact    7609
acatttcgct catcgccagc ccagtcgggc ggcgagttcc atagcgttaa ggtttcattt    7669
agcgcctcaa atagatcctg ttcaggaacc ggatcaaaga gttcctccgc cgctggacct    7729
accaaggcaa cgctatgttc tcttgctttt gtcagcaaga tagccagatc aatgtcgatc    7789
gtggctggct cgaagatacc tgcaagaatg tcattcgcct gccattctcc aaattgcagt    7849
tcgcgcttag ctggataacg ccacggaatg atgtcgtcgt gcacaacaat ggtgacttct    7909
acagcgcgga gaatctcgct ctctccaggg gaagccgaag tttccaaaag gtcgttgatc    7969
aaagctcgcc gcgttgtttc atcaagcctt acggtcaccg taaccagcaa atcaatatca    8029
ctgtgtggct tcaggccgcc atccactgcg gagccgtaca aatgtacggc cagcaacgtc    8089
ggttcgagat ggcgctcgat gacgccaact acctctgata gttgagtcga tacttcggcg    8149
atcaccgctt ccctcatgat gtttaacttt gttttagggc gactgccctg ctgcgtaaca    8209
tcgttgctgc tccataacat caaacatcga cccacggcgt aacgcgcttg ctgcttggat    8269
gcccgaggca tagactgtac cccaaaaaaa cagtcataac aagccatgaa aaccgccact    8329
gcgccgttac caccgctgcg ttcggtcaag gttctggacc agttgcgtga gcgcatacgc    8389
tacttgcatt acagcttacg aaccgaacag gcttatgtcc actgggttcg tgccttcatc    8449
cgtttccacg gtgtgcgtca cccggcaacc ttgggcagca gcgaagtcga ggcatttctg    8509
tcctggctgg cgaacgagcg caaggttccg gtctccacgc atcgtcaggc attggcggcc    8569
ttgctgttct tctacggcaa gtgctgtgca cggatctgcc ctggcttc    8617
```

```
<210> SEQ ID NO 21
<211> LENGTH: 358
<212> TYPE: PRT
<213> ORGANISM: Artificial
<220> FEATURE:
<223> OTHER INFORMATION: Synthetic Construct

<400> SEQUENCE: 21

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
                20                  25                  30

Ile Met Gly Phe Thr Lys Val Ala Thr His Arg Ser Lys Asn Val His
            35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Trp
                325                 330                 335

Asn Phe Lys Ala Leu Phe Glu Ser Ile Glu Arg Asp Gln Val Arg Arg
            340                 345                 350

Gly Val Leu Thr Ala Asp
        355
```

```
<210> SEQ ID NO 22
<211> LENGTH: 445
<212> TYPE: PRT
<213> ORGANISM: Artificial
<220> FEATURE:
<223> OTHER INFORMATION: Synthetic Construct

<400> SEQUENCE: 22

Met Ala Gly Ala Glu Glu Ile Val Leu Gln Pro Ile Lys Glu Ile Ser
1               5                   10                  15

Gly Thr Val Lys Leu Pro Gly Ser Lys Ser Leu Ser Asn Arg Ile Leu
            20                  25                  30

Leu Leu Ala Ala Leu Ser Glu Gly Thr Thr Val Val Asp Asn Leu Leu
        35                  40                  45

Asn Ser Glu Asp Val His Tyr Met Leu Gly Ala Leu Arg Thr Leu Gly
    50                  55                  60

Leu Ser Val Glu Ala Asp Lys Ala Ala Lys Arg Ala Val Val Val Gly
65                  70                  75                  80

Cys Gly Gly Lys Phe Pro Val Glu Asp Ala Lys Glu Glu Val Gln Leu
                85                  90                  95

Phe Leu Gly Asn Ala Gly Ile Ala Met Arg Ser Leu Thr Ala Ala Val
            100                 105                 110

Thr Ala Ala Gly Gly Asn Ala Thr Tyr Val Leu Asp Gly Val Pro Arg
        115                 120                 125

Met Arg Glu Arg Pro Ile Gly Asp Leu Val Val Gly Leu Lys Gln Leu
    130                 135                 140

Gly Ala Asp Val Asp Cys Phe Leu Gly Thr Asp Cys Pro Pro Val Arg
145                 150                 155                 160

Val Asn Gly Ile Gly Gly Leu Pro Gly Gly Lys Val Lys Leu Ser Gly
                165                 170                 175

Ser Ile Ser Ser Gln Tyr Leu Ser Ala Leu Leu Met Ala Ala Pro Leu
            180                 185                 190

Ala Leu Gly Asp Val Glu Ile Glu Ile Ile Asp Lys Leu Ile Ser Ile
        195                 200                 205

Pro Tyr Val Glu Met Thr Leu Arg Leu Met Glu Arg Phe Gly Val Lys
    210                 215                 220

Ala Glu His Ser Asp Ser Trp Asp Arg Phe Tyr Ile Lys Gly Gly Gln
225                 230                 235                 240

Lys Tyr Lys Ser Pro Lys Asn Ala Tyr Val Glu Gly Asp Ala Ser Ser
                245                 250                 255

Ala Ser Tyr Phe Leu Ala Gly Ala Ala Ile Thr Gly Gly Thr Val Thr
            260                 265                 270

Val Glu Gly Cys Gly Thr Thr Ser Leu Gln Gly Asp Val Lys Phe Ala
        275                 280                 285

Glu Val Leu Glu Met Met Gly Ala Lys Val Thr Trp Thr Glu Thr Ser
    290                 295                 300

Val Thr Val Thr Gly Pro Pro Arg Glu Pro Phe Gly Arg Lys His Leu
305                 310                 315                 320

Lys Ala Ile Asp Val Asn Met Asn Lys Met Pro Asp Val Ala Met Thr
                325                 330                 335

Leu Ala Val Val Ala Leu Phe Ala Asp Gly Pro Thr Ala Ile Arg Asp
            340                 345                 350

Val Ala Ser Trp Arg Val Lys Glu Thr Glu Arg Met Val Ala Ile Arg
        355                 360                 365
```

Thr Glu Leu Thr Lys Leu Gly Ala Ser Val Glu Glu Gly Pro Asp Tyr
370                 375                 380

Cys Ile Ile Thr Pro Pro Glu Lys Leu Asn Val Thr Ala Ile Asp Thr
385                 390                 395                 400

Tyr Asp Asp His Arg Met Ala Met Ala Phe Ser Leu Ala Ala Cys Ala
                405                 410                 415

Glu Val Pro Val Thr Ile Arg Asp Pro Gly Cys Thr Arg Lys Thr Phe
            420                 425                 430

Pro Asp Tyr Phe Asp Val Leu Ser Thr Phe Val Lys Asn
            435                 440                 445

<210> SEQ ID NO 23
<211> LENGTH: 13080
<212> TYPE: DNA
<213> ORGANISM: Artificial Sequence
<220> FEATURE:
<223> OTHER INFORMATION: vector

<400> SEQUENCE: 23
aattacaacg gtatatatcc tgccagtact gggcccccctc gagggcgatc gctacgtacc     60
tgcaggcccg ggttaattaa ggcccgatca aatctgaggg acgttaaagc gatgataaat    120
tggaaccaga atatagaatc tttgttctgc tctagctttt cttctgtaca tttttttacga   180 ttagactatg attttcattc aataaccaaa attctgaagt ttgtcatcaa gttgctcaat    240
caaacttgta ccggtttgtt tcggttttat atcagctcac tgttacactt taaccaaaat    300
cggtttatgt cttaataaag gaattgagtc ggtttaactc atatccgtac caatgcgacg    360
tcgtgtccgc gtttcagtag ctttgctcat tgtcttctac gggaactttc ccggacatag    420
gaaccgccct ttcgttatcc tcatccatcg tgaaatcagg aaataaatgt tcgaagattt    480
gaggtcaaaa gtcgaatttc atgttgtctc ttctatttag atacaaaatt gaagcaattt    540
tcaccaattt aatgccaaaa tttaaaacaa cgctgataaa gtgaaacttg attcgatttta   600 tatttcaacc gaaactgctg aagcaagaag aaaaagcgta attacacata acaagaacgc    660
taccgcaaac tactaaacgc caaacccaat acaaaagtaa aacgcagacg cttaagtgag    720
aaacccagaa aacacaaacg cggatcgggc gacgcgtgct agcttttaat cagcggtcaa    780 aaccccctcta cgaacttgat ccctctctat cgattcgaaa agtgctttga agttccattc    840
tccgaagcca tcgtcccctt tacgctgaat gaactcaaag aaaacgggtc ccatgagagt    900
ctcggaaaag atttgtaaca ggagcctctt atcaccctca accgaagaac catcgagaag    960 tatcccctg gcttgcagtt ggtccacggg ttccccatga tcaggcaggc gtccttctag    1020
catctcatag taagtatcgg gaggtgcagt catgaatctc atacctatct tcttcaatgc    1080
atcccaggtt ttcacaagat catcagtcag aaaagcgaca tgctgaatgc cttcaccatt    1140
gaactgcata agaaactctt cgatttgtcc tgcaccttg cttgactctt cgttgagtgg    1200
aatccttatc ataccatctg gagcgctcat agcctttgat gtgagaccag tatactctcc    1260
tttgatgtca aagtatctag cttccctaaa gttgaagagt ttctcataga agttagccca    1320
gtataccatt cgtccacgat agacgttgtg tgtcaaatga tcaataacct tcaagccagc    1380
accgacagga tttcgttcca cgccttcaag atagacgaaa tctatgtcgt agatagaact    1440
gccctctccg aatctgtcga taagatacaa cggtgcacca ccgatgcctt tgatggctgg    1500
aagattcaat tccataggtc cagtgtcaat gtgaataggc tgagctccaa gttctaatgc    1560
cctattgtag gctttctggg aatccttaac tcgaaatgcc atgccacaaa cggatggtcc    1620

-continued

```
atgttcggca gcaaagtagc ttgctataga gttaggttcg ttgttcaaga tcaggttaat    1680
ctctccttgc cgatataggt gcacgttctt actgcgatgt gtagctacct tagtaaaccc    1740
cataatctca aagatgggtt caagggtccc aggtgtagga gaagcaaact caatgaactc    1800
gaaacccatg agtcccatag gattctcgta tagatcagcc atgcatctaa tcctacctcc    1860
gttgctaaca ttccccagcg atctggaaga tctccgagca actggcaaac tagcagtact    1920
cttcaaccct tgaaatggtg ccacagctgt ggcagagctg ccatcatca cagtgggagc     1980
catagatagc ggaggtaagt aggataaggt ctcaaacttc ttgttgccat aggctggcca    2040
gacttgcata tactgtactc tcccaccgtt gctcggaagt gttgagaagt cattagcctt    2100
cttagtggtt ggaaatgcag catttgactt aagacctgtg aacggagcca ccatattagc    2160
ttgggctggt gcggtacgtg aaacagtggc aactgaagat gaaatactag ccatggtttt    2220
ggacaaactt acaaatttct ctgaagttgt atcctcagta cttcaaagaa aatagcttac    2280
accaaatttt ttcttgtttt cacaaatgcc gaacttggtt ccttatatag gaaaactcaa    2340
gggcaaaaat gacacggaaa aatataaaag ataagtagt gggggataag attcctttgt     2400
gataaggtta ctttccgccc ttacattttc caccttacat gtgtcctcta tgtctctttc    2460
acaatcaccg accttatctt cttcttttca ttgttgtcgt cagtgcttac gtcttcaaga    2520
ttcttttctt cgcctggttc ttcttttttca atttctacgt attcttcttc gtattctggc    2580
agtataggat cttgtatctg tacattcttc atttttgaac ataggttgca tatgtgccgc    2640
atattgatct gcttcttgct gagctcacat aatacttcca tagttttttcc cgtaaacatt   2700
ggattcttga tgctacatct tggataatta ccttcgcggc cgcttggcgc gccgaattcg    2760
atatcattac cctgttatcc ctaaagctta ttaatataac ttcgtatagc atacattata    2820
cgaagttatg tttgtcgagg agaaatatga gtcgaggcat ggatacacta agttcccctg    2880
aagtgagcat gatctttgat gctgagatga ttcccagagc aagatagttt gtgctgcaag    2940
tgacacaatt gtaatgaaac caccactcaa cgaatttact tgtggctttg acatgtcgtg    3000
tgctctgttt gtatttgtga gtgccggttg gtaattattt ttgttaatgt gattttaaaa    3060
cctcttatgt aaatagttac tttatctatt gaagtgtgtt cttgtggtct atagtttctc    3120
aaagggaaat taaaatgttg acatcccatt tacaattgat aacttggtat acacaaactt    3180
tgtaaatttg gtgatattta tggtcgaaag aaggcaatac ccattgtatg ttccaatatc    3240
aatatcaata cgataacttg ataatactaa catatgattg tcattgtttt tccagtatca    3300
atatacatta agctactaca aaattagtat aaatcactat attataaatc tttttcggtt    3360
gtaacttgta attcgtgggt ttttaaaata aaagcatgtg aaaattttca ataatgtga     3420
tggcgcaatt ttattttccg agttccaaaa tattgccgct tcattaccct aatttgtggc    3480
gccacatgta aaacaaaaga cgattcttag tggctatcac tgccatcacg cggatcacta    3540
atatgaaccg tcgattaaaa cagatcgacg gtttatacat cattttattg tacacacgga    3600
tcgatatctc agccgttaga tttaatatgc gatctgattg ctcaaaaaat agactctccg    3660
tctttgccta taaaaacaat ttcacatctt tctcacccaa atctactctt aaccgttctt    3720
cttcttctac agacatcaat ttctctcgac tctagaggat ccaagcttat cgatttcgaa    3780
cccctcaggc gaagaacagg tatgatttgt ttgtaattag atcaggggtt taggtctttc    3840
cattactttt taatgttttt tctgttactg tctccgcgat ctgatttac gacaatagag     3900
tttcgggttt tgtcccattc cagtttgaaa ataaggtcc gtcttttaag tttgctggat     3960
cgataaacct gtgaagattg agtctagtcg atttattgga tgatccattc ttcatcgttt    4020
```

```
ttttcttgct tcgaagttct gtataaccag atttgtctgt gtgcgattgt cattacctag    4080
ccgtgtatcg agaactaggg ttttcgagtc aattttgccc cttttggtta tatctggttc    4140
gataacgatt catctggatt agggttttaa gtggtgacgt ttagtattcc aatttcttca    4200
aaatttagtt atggataatg aaaatcccca attgactgtt caatttcttg ttaaatgcgc    4260
agatcacaat ggcttcgatc tcctcctcag tcgcgaccgt tagccggacc gccctgctc     4320 aggccaacat ggtggctccg ttcaccggcc ttaagtccaa cgccgccttc ccaccacca    4380 agaaggctaa cgacttctcc acccttccca gcaacggtgg aagagttcaa tgtatgcagg    4440
tgtggccggc ctacggcaac aagaagttcg agacgctgtc gtacctgccg ccgctgtcta    4500
tggcgcccac cgtgatgatg gcctcgtcgg ccaccgccgt cgctccgttc caggggctca    4560
agtccaccgc cagcctcccc gtcgcccgcc gctcctccag aagcctcggc aacgtcagca    4620
acggcggaag gatccggtgc atggccggcg ccgaggagat cgtgctgcag cccatcaagg    4680
agatctccgg caccgtcaag ctgccggggt ccaagtcgct ttccaaccgg atcctcctac    4740
tcgccgccct gtccgagggg acaacagtgg ttgataacct gctgaacagt gaggatgtcc    4800
actacatgct cggggccttg aggactcttg gtctctctgt cgaagcggac aaagctgcca    4860
aaagagctgt agttgttggc tgtggtggaa agttcccagt tgaggatgct aaagaggaag    4920
tgcagctctt cttggggaat gctggaatcg caatgcggtc cttgacagca gctgttactg    4980
ctgctggtgg aaatgcaact tacgtgcttg atggagtacc aagaatgagg gagagaccca    5040
ttggcgactt ggttgtcgga ttgaagcagc ttggtgcaga tgttgattgt ttccttggca    5100
ctgactgccc acctgttcgt gtcaatggaa tcggagggct acctggtggc aaggtcaagc    5160
tgtctggctc catcagcagt cagtacttga gtgccttgct gatggctgct cctttggctc    5220 ttgggggatgt ggagattgaa atcattgata aattaatctc cattccgtac gtcgaaatga    5280
cattgagatt gatggagcgt tttggtgtga agcagagca ttctgatagc tgggacagat     5340
tctacattaa gggaggtcaa aaatacaagt cccctaaaaa tgcctatgtt gaaggtgatg    5400
cctcaagcgc aagctatttc ttggctggtg ctgcaattac tggagggact gtgactgtgg    5460
aaggttgtgg caccaccagt ttgcagggtg atgtgaagtt tgctgaggta ctggagatga    5520
tgggagcgaa ggttacatgg accgagacta gcgtaactgt tactggccca ccgcgggagc    5580
catttgggag gaaacacctc aaggcgattg atgtcaacat gaacaagatg cctgatgtcg    5640
ccatgactct tgctgtggtt gccctctttg ccgatggccc gacagccatc agagacgtgg    5700
cttcctggag agtaaaggag accgagagga tggttgcgat ccggacggag ctaaccaagc    5760
tgggagcatc tgttgaggaa gggccggact actgcatcat cacgccgccg gagaagctga    5820
acgtgacggc gatcgacacg tacgacgacc acaggatggc gatggccttc tcccttgccg    5880
cctgtgccga ggtccccgtc accatccggg accctgggtg cacccggaag accttccccg    5940
actacttcga tgtgctgagc actttcgtca agaattaagc tctagaacta gtggatcccc    6000
cgatccgcgt ttgtgttttc tgggtttctc acttaagcgt ctgcgtttta cttttgtatt    6060
gggtttggcg tttagtagtt tgcggtagcg ttcttgttat gtgtaattac gcttttctt     6120 cttgcttcag cagtttcggt tgaaatataa atcgaatcaa gttcactttt atcagcgttg    6180
ttttaaattt tggcattaaa ttggtgaaaa ttgcttcaat tttgtatcta aatagaagag    6240
acaacatgaa attcgacttt tgaccctcaaa tcttcgaaca tttatttcct gatttccga    6300 tggatgagga taacgaaagg gcggttccta tgtccgggaa agttcccgta gaagacaatg    6360
```

```
agcaaagcta ctgaaacgcg gacacgacgt cgcattggta cggatatgag ttaaaccgac   6420
tcaattcctt tattaagaca taaaccgatt ttggttaaag tgtaacagtg agctgatata   6480
aaaccgaaac aaaccggtac aagtttgatt gagcaacttg atgacaaact tcagaattttt  6540 ggttattgaa tgaaaatcat agtctaatcg taaaaaatgt acagaagaaa agctagagca   6600
gaacaaagat tctatattct ggttccaatt tatcatcgct ttaacgtccc tcagatttga   6660
tcgggaaaca taacttcgta tagcatacat tatacgaagt tatcaaaacg tcgtgagaca   6720
gtttggttaa ctataacggt cctaaggtag cgatcgaggc attacggcat tacggcactc   6780
gcgagggtcc gaatctatgt cgggtgcgga gaaagaggta atgaaatggc aatttacaat   6840
tgaatatatc ctgccgccgc tgccgctttg cacccggtgg agcttgcatg ttggtttcta   6900
cgcagaactg agccggttag gcagataatt tccattgaga actgagccat gtgcaccttc   6960
cccccaacac ggtgagcgac ggggcaacgg agtgatccac atgggacttt taaacatcat   7020
ccgtcggatg gcgttgcgag agaagcagtc gatccgtgag atcagccgac gcaccgggca   7080
ggcgcgcaac acgatcgcaa agtatttgaa cgcaggtaca atcgagccga cgttcacggt   7140
accggaacga ccaagcaagc tagcttagta aagccctcgc tagattttaa tgcggatgtt   7200
gcgattactt cgccaactat tgcgataaca agaaaaagcc agccttttcat gatatatctc   7260 ccaatttgtg tagggcttat tatgcacgct taaaaataat aaaagcagac ttgacctgat   7320
agtttggctg tgagcaatta tgtgcttagt gcatctaacg cttgagttaa ccgcgccgc   7380 gaagcggcgt cggcttgaac gaattgttag acattatttg ccgactacct tggtgatctc   7440
gcctttcacg tagtggacaa attcttccaa ctgatctgcg cgcgaggcca agcgatcttc   7500
ttcttgtcca agataagcct gtctagcttc aagtatgacg ggctgatact gggccggcag   7560
gcgctccatt gcccagtcgg cagcgacatc cttcggcgcg attttgccgg ttactgcgct   7620
gtaccaaatg cgggacaacg taagcactac atttcgctca tcgccagccc agtcgggcgg   7680
cgagttccat agcgttaagg tttcatttag cgcctcaaat agatcctgtt caggaaccgg   7740
atcaaagagt tcctccgccg ctggacctac caaggcaacg ctatgttctc ttgcttttgt   7800
cagcaagata gccagatcaa tgtcgatcgt ggctggctcg aagatacctg caagaatgtc   7860
attgcgctgc cattctccaa attgcagttc gcgcttagct ggataacgcc acggaatgat   7920
gtcgtcgtgc acaacaatgg tgacttctac agcgcggaga atctcgctct tccaggggga   7980
agccgaagtt tccaaaaggt cgttgatcaa agctcgccgc gttgtttcat caagccttac   8040
ggtcaccgta accagcaaat caatatcact gtgtggcttc aggccgccat ccactgcgga   8100
gccgtacaaa tgtacggcca gcaacgtcgg ttcgagatgg cgctcgatga cgccaactac   8160
ctctgatagt tgagtcgata cttcggcgat caccgcttcc ctcatgatgt ttaactttgt   8220
tttagggcga ctgccctgct gcgtaacatc gttgctgctc cataacatca aacatcgacc   8280
cacggcgtaa cgcgcttgct gcttggatgc ccgaggcata gactgtaccc caaaaaaaca   8340
gtcataacaa gccatgaaaa ccgccactgc gccgttacca ccgctgcgtt cggtcaaggt   8400
tctggaccag ttgcgtgagc gcatacgcta cttgcattac agcttacgaa ccgaacaggc   8460
ttatgtccac tgggttcgtg ccttcatccg tttccacggt gtgcgtcacc cggcaacctt   8520
gggcagcagc gaagtcgagg catttctgtc ctggctggcg aacgagcgca aggtttcggt   8580
ctccacgcat cgtcaggcat ggcggcctt gctgttcttc tacggcaagt gctgtgcacg   8640
gatctgccct ggcttcagga gatcggaaga cctcggccgt ccgggcgctt gccggtggtg   8700
ctgaccccgg atgaagtctc tagagctcta gagggttcgc atcctcggtt ttctggaagg   8760
```

-continued

```
cgagcatcgt tgttcgccc agcttctgta tggaacgggc atgcggatca gtgagggttt    8820
gcaactgcgg gtcaaggatc tggatttcga tcacggcacg atcatcgtgc gggagggcaa    8880
gggctccaag gatcgggcct tgatgttacc cgagagcttg gcacccagcc tgcgcgagca    8940
gggatcgata ccgtgcggct gcatgaaatc ctggccggtt tgtctgatgc caagctggcg    9000
gcctggccgg ccagcttggc cgctgaagaa accgagcgcc gccgtctaaa aggtgatgt     9060 gtatttgagt aaaacagctt gcgtcatgcg gtcgctgcgt atatgatgcg atgagtaaat    9120
aaacaaatac gcaaggggaa cgcatgaagg ttatcgctgt acttaaccag aaaggcgggt    9180
caggcaagac gaccatcgca acccatctag cccgcgccct gcaactcgcc ggggccgatg    9240
ttctgttagt cgattccgat ccccagggca gtgcccgcga ttgggcggcc gtgcgggaag    9300
atcaaccgct aaccgttgtc ggcatcgacc gcccgacgat tgaccgcgac gtgaaggcca    9360
tcggccggcg cgacttcgta gtgatcgacg agcgcccca ggcggcggac ttggctgtgt     9420
ccgcgatcaa ggcagccgac ttcgtgctga ttccggtgca gccaagccct tacgacatat    9480
gggccaccgc cgacctggtg gagctggtta agcagcgcat tgaggtcacg gatggaaggc    9540
tacaagcggc ctttgtcgtg tcgcgggcga tcaaaggcac gcgcatcggc ggtgaggttg    9600
ccgaggcgct ggccgggtac gagctgccca ttcttgagtc ccgtatcacg cagcgcgtga    9660 gctaccagg cactgccgcc gccggcacaa ccgttcttga atcagaaccc gagggcgacg     9720
ctgcccgcga ggtccaggcg ctggccgctg aaattaaatc aaaactcatt tgagttaatg    9780
aggtaaagag aaaatgagca aaagcacaaa cacgctaagt gccggccgtc cgagcgcacg    9840
cagcagcaag gctgcaacgt tggccagcct ggcagacacg ccagccatga agcgggtcaa    9900
ctttcagttg ccggcggagg atcacaccaa gctgaagatg tacgcggtac gccaaggcaa    9960
gaccattacc gagctgctat ctgaatacat cgcgcagcta ccagagtaaa tgagcaaatg   10020
aataaatgag tagatgaatt ttagcggcta aggaggcgg catggaaaat caagaacaac    10080
caggcaccga cgccgtggaa tgccccatgt gtggaggaac gggcggttgg ccaggcgtaa   10140
gcggctgggt tgtctgccgg ccctgcaatg gcactggaac ccccaagccc gaggaatcgg   10200
cgtgacggtc gcaaaccatc cggcccgta caaatcggcg cggcgctggg tgatgacctg    10260
gtggagaagt tgaaggccgc gcaggccgcc cagcggcaac gcatcgaggc agaagcacgc   10320
cccggtgaat cgtggcaagc ggccgctgat cgaatccgca aagaatcccg gcaaccgccg   10380
gcagccggtg cgccgtcgat taggaagccg cccaagggcg acgagcaacc agatttttc    10440 gttccgatgc tctatgacgt gggcacccgc gatagtcgca gcatcatgga cgtggccgtt   10500
ttccgtctgt cgaagcgtga ccgacgagct ggcgaggtga tccgctacga gcttccagac   10560
gggcacgtag aggtttccgc agggccggcc ggcatggcca gtgtgtggga ttacgacctg   10620
gtactgatgg cggtttccca tctaaccgaa tccatgaacc gataccggga agggaaggga   10680
gacaagcccg gccgcgtgtt ccgtccacac gttgcggacg tactcaagtt ctgccggcga   10740
gccgatggcg gaaagcagaa agacgacctg gtagaaacct gcattcggtt aaacaccacg   10800
cacgttgcca tgcagcgtac gaagaaggcc aagaacggcc gcctggtgac ggtatccgag   10860
ggtgaagcct tgattagccg ctacaagatc gtaaagagcg aaaccgggcg gccggagtac   10920
atcgagatcg agctagctga ttggatgtac cgcgagatca cagaaggcaa gaacccggac   10980
gtgctgacgg ttcaccccga ttacttttg atcgatcccg gcatcggccg ttttctctac    11040
cgcctggcac gccgcgccgc aggcaaggca gaagccagat ggttgttcaa gacgatctac   11100
```

```
gaacgcagtg gcagcgccgg agagttcaag aagttctgtt tcaccgtgcg caagctgatc    11160
gggtcaaatg acctgccgga gtacgatttg aaggaggagg cggggcaggc tggcccgatc    11220
ctagtcatgc gctaccgcaa cctgatcgag ggcgaagcat ccgccggttc ctaatgtacg    11280
gagcagatgc tagggcaaat tgccctagca ggggaaaaag gtcgaaaagg tctctttcct    11340
gtggatagca cgtacattgg gaacccaaag ccgtacattg gaaccggaa cccgtacatt     11400 gggaacccaa agccgtacat tgggaaccgg tcacacatgt aagtgactga tataaaagag    11460
aaaaaaggcg atttttccgc ctaaaactct ttaaaactta ttaaaactct taaaacccgc    11520
ctggcctgtg cataactgtc tggccagcgc acagccgaag agctgcaaaa agcgcctacc    11580
cttcggtcgc tgcgctccct acgccccgcc gcttcgcgtc ggcctatcgc ggccgctggc    11640
cgctcaaaaa tggctggcct acggccaggc aatctaccag ggcgcggaca agccgcgccg    11700
tcgccactcg accgccggcg cccacatcaa ggcaccctgc ctcgcgcgtt tcggtgatga    11760
cggtgaaaac ctctgacaca tgcagctccc ggagacggtc acagcttgtc tgtaagcgga    11820
tgccgggagc agacaagccc gtcagggcgc gtcagcgggt gttggcgggt gtcggggcgc    11880
agccatgacc cagtcacgta gcgatagcgg agtgtatact ggcttaacta tgcggcatca    11940
gagcagattg tactgagagt gcaccatatg cggtgtgaaa taccgcacag atgcgtaagg    12000
agaaaatacc gcatcaggcg ctcttccgct tcctcgctca ctgactcgct gcgctcggtc    12060
gttcggctgc ggcgagcggt atcagctcac tcaaaggcgg taatacggtt atccacagaa    12120 tcagggata acgcaggaaa gaacatgtga gcaaaaggcc agcaaaaggc caggaaccgt     12180
aaaaaggccg cgttgctggc gtttttccat aggctccgcc ccctgacga gcatcacaaa     12240 aatcgacgct caagtcagag gtggcgaaac ccgacaggac tataaagata ccaggcgttt    12300
ccccctggaa gctccctcgt gcgctctcct gttccgaccc tgccgcttac cggatacctg    12360
tccgcctttc tcccttcggg aagcgtggcg ctttctcata gctcacgctg taggtatctc    12420
agttcggtgt aggtcgttcg ctccaagctg ggctgtgtgc acgaaccccc cgttcagccc    12480
gaccgctgcg ccttatccgg taactatcgt cttgagtcca acccggtaag acacgactta    12540
tcgccactgg cagcagccac tggtaacagg attagcagag cgaggtatgt aggcggtgct    12600
acagagttct tgaagtggtg gcctaactac ggctacacta gaaggacagt atttggtatc    12660
tgcgctctgc tgaagccagt taccttcgga aaaagagttg gtagctcttg atccggcaaa    12720
caaaccaccg ctggtagcgg tggtttttt gtttgcaagc agcagattac gcgcagaaaa     12780
aaaggatctc aagaagatcc ggaaaacgca agcgcaaaga gaaagcaggt agcttgcagt    12840
gggcttacat ggcgatagct agactgggcg gttttatgga cagcaagcga accggaattg    12900
ccagattcga agctcggtcc cgtgggtgtt ctgtcgtctc gttgtacaac gaaatccatt    12960
cccattccgc gctcaagatg gcttccctc ggcagttcat cagggctaaa tcaatctagc     13020
cgacttgtcc ggtgaaatgg gctgcactcc aacagaaaca atcaaacaaa catacacagc    13080
```

METHODS AND MEANS TO MODIFY A PLANT GENOME

CROSS-REFERENCE TO RELATED APPLICATIONS

This application is a Divisional Application of U.S. patent application Ser. No. 14/240,500, filed Jun. 27, 2014, which is the U.S. National Phase of International Patent Application No. PCT/EP2012/065867, filed Aug. 14, 2012, which claims priority to: U.S. Provisional Application No. 61/525,892, filed Aug. 22, 2011; EP Application No. 11075198.9, filed Aug. 25, 2011; EP Application No. 11193103.6, filed Dec. 12, 2011; and U.S. Provisional Application No. 61/569,518, filed Dec. 12, 2011, the contents of each are hereby incorporated by reference in their entireties.

FIELD OF THE INVENTION

The invention relates to the field of agronomy. More particularly, the invention provides methods and means to introduce a targeted modification, including insertion, deletion or substitution, at a precisely localized nucleotide sequence in the genome of a plant using a custom-designed double stranded DNA break inducing enzyme. The invention further relates to a cotton plant cell, plant part, plant, or seed comprising a chimeric gene comprising a nucleic acid sequence encoding a protein having HPPD activity, wherein said protein has a tryptophan at a position corresponding to position 336 of SEQ ID NO: 1, wherein said protein provides to said plant tolerance to a field dose of at least 1× of at least one HPPD inhibitor, and methods for making such plants.

BACKGROUND ART

The need to introduce targeted modifications in plant genomes, e.g. to provide plants with agronomically useful traits such as herbicide tolerance, including the control over the location of integration of foreign DNA in plants has become increasingly important. Several methods have been developed in an effort to meet this need (for a review see Kumar and Fladung, 2001, *Trends in Plant Science*, 6, pp 155-159), which mostly rely on the initial introduction of a double stranded DNA break at the targeted location via expression of a double strand break inducing (DSBI) enzyme.

Activation of the target locus and/or repair or donor DNA through the induction of double stranded DNA breaks (DSB) via rare-cutting endonucleases, such as I-SceI has been shown to increase the frequency of homologous recombination by several orders of magnitude. (Puchta et al., 1996, *Proc. Natl. Acad. Sci. U.S.A.*, 93, pp 5055-5060; Chilton and Que, *Plant Physiol.*, 2003; D'Halluin et al. 2008 *Plant Biotechnol. J.* 6, 93-102).

WO96/14408 describes an isolated DNA encoding the enzyme I-SceI. This DNA sequence can be incorporated in cloning and expression vectors, transformed cell lines and transgenic animals. The vectors are useful in gene mapping and site-directed insertion of genes.

WO00/46386 describes methods of modifying, repairing, attenuating and inactivating a gene or other chromosomal DNA in a cell through an I-SceI induced double strand break. Also disclosed are methods of treating or prophylaxis of a genetic disease in an individual in need thereof. Further disclosed are chimeric restriction endonucleases.

WO 2005/049842 describes methods and means to improve targeted DNA insertion in plants using rare-cleaving "double stranded break" inducing (DSBI) enzymes, as well as improved I-SceI encoding nucleotide sequences.

WO2006/105946 describes a method for the exact exchange in plant cells and plants of a target DNA sequence for a DNA sequence of interest through homologous recombination, whereby the selectable or screenable marker used during the homologous recombination phase for temporal selection of the gene replacement events can subsequently be removed without leaving a foot-print and without resorting to in vitro culture during the removal step, employing the therein described method for the removal of a selected DNA by microspore specific expression of a DSBI rare-cleaving endonuclease.

WO2008/037436 describe variants of the methods and means of WO2006/105946 wherein the removal step of a selected DNA fragment induced by a double stranded break inducing rare cleaving endonuclease is under control of a germline-specific promoter. Other embodiments of the method relied on non-homologous endjoining at one end of the repair DNA and homologous recombination at the other end. WO08/148559 describes variants of the methods of WO2008/037436, i.e. methods for the exact exchange in eukaryotic cells, such as plant cells, of a target DNA sequence for a DNA sequence of interest through homologous recombination, whereby the selectable or screenable marker used during the homologous recombination phase for temporal selection of the gene replacement events can subsequently be removed without leaving a foot-print employing a method for the removal of a selected DNA flanked by two nucleotide sequences in direct repeats.

WO 2003/004659 discloses recombination systems and a method for removing nucleic acid sequences from the chromosomal DNA of eukaryotic organisms. The invention also relates to transgenic organisms (preferably plants), containing said systems or produced by said method.

WO 2006/032426 discloses improved recombination systems and methods for eliminating maker sequences from the genome of plants. Particularly the invention is based on use of an expression cassette comprising the parsley ubiquitin promoter, and operably linked thereto a nucleic acid sequence coding for a sequence specific DNA-endonuclease.

U.S. provisional application 61/493,579 and EP11004570.5 describe methods and means to modify in a targeted manner the genome of a cotton plant using a double stranded DNA break inducing enzyme and embryogenic callus.

In addition, methods have been described which allow the design of rare cleaving endonucleases to alter substrate or sequence-specificity of the enzymes, thus allowing to induce a double stranded break at a locus of interest without being dependent on the presence of a recognition site for any of the natural rare-cleaving endonucleases. Briefly, chimeric restriction enzymes can be prepared using hybrids between a zinc-finger domain designed to recognize a specific nucleotide sequence and the non-specific DNA-cleavage domain from a natural restriction enzyme, such as FoId. Such methods have been described e.g. in WO 03/080809, WO94/18313 or WO95/09233 and in Isalan et al., 2001, *Nature Biotechnology* 19, 656-660; Liu et al. 1997, Proc. Natl. Acad. Sci. USA 94, 5525-5530). Another way of producing custom-made meganucleases, by selection from a library of variants, is described in WO2004/067736. Custom made meganucleases or redesigned meganucleases with altered sequence specificity and DNA-binding affinity may also be obtained through rational design as described in WO2007/047859.

WO2007/049095 describes "LADGLIDADG" homing endonuclease variants having mutations in two separate subdomains, each binding a distinct part of a modified DNA target half site, such that the endonuclease variant is able to cleave a chimeric DNA target sequence comprising the nucleotides bound by each subdomain.

WO2007/049156 and WO2007/093836 describe I-CreI homing endonuclease variants having novel cleavage specificity and uses thereof.

WO2007/047859 describes rationally designed meganucleases with altered sequence specificity and DNA binding affinity.

WO11/064736 describes optimized endonucleases, as well as methods of targeted integration, targeted deletion or targeted mutation of polynucleotides using optimized endonucleases. WO11/064750 describes chimeric endonucleases, comprising an endonuclease and a heterologous DNA binding domain comprising one or more Zn2C6 zinc fingers, as well as methods of targeted integration, targeted deletion or targeted mutation of polynucleotides using chimeric endonucleases and WO11/064751 describes chimeric endonucleases, comprising an endonuclease and a heterologous DNA binding domain, as well as methods of targeted integration, targeted deletion or targeted mutation of polynucleotides using chimeric endonucleases.

PCT/EP11/002894 and PCT/EP11/002895 describe methods and means to modify in a targeted manner the plant genome of transgenic plants comprising chimeric genes wherein the chimeric genes have a DNA element commonly used in plant molecular biology, as well as re-designed meganucleases to cleave such an element commonly used in plant molecular biology.

WO 2009/006297 discloses methods and compositions for altering the genome of a monocot plant cell, and a monocot plant, involving the use of a double-stranded break inducing agent to alter a monocot plant or plant cell genomic sequence comprising a recognition sequence for the double-stranded break inducing agent.

Gao et al. 2010, *The Plant Journal* 61, p 176-187 describe heritable targeted mutagenesis in maize using a re-designed endonuclease.

However, in order to efficiently make combinations of agronomically useful traits without having to resort to elaborate breeding schemes or to test large numbers of single events, there thus still remains a need for functional re-designed meganucleases which can recognize a recognition site in close proximity to an already existing elite event, and uses thereof in order to make stacks of genes conferring agronomically favorable properties at a single genetic locus.

One of such agronomically useful traits is tolerance to herbicides, such as HPPD-inhibitor herbicides. HPPD (hydroxyphenylpyruvate dioxygenase) proteins are enzymes which catalyse the reaction in which para-hydroxyphenylpyruvate (abbreviated herein as HPP), a tyrosine degradation product, is transformed into homogentisate (abbreviated herein as HG), the precursor in plants of tocopherol and plastoquinone (Crouch N. P. et al. (1997) Tetrahedron, 53, 20, 6993-7010, Fritze et al., (2004), Plant Physiology 134: 1388-1400). Tocopherol acts as a membrane-associated antioxidant. Plastoquinone, firstly acts as an electron carrier between photosystem II (PSII) and the cytochrome b6/f complex and secondly, is a redox cofactor for phytoene desaturase, which is involved in the biosynthesis of carotenoids.

Up to now, more than 700 nucleic acid sequences from various organisms present in NCBI database were annotated as coding for a putative protein having an HPPD domain. Several HPPD proteins and their primary sequences have been described in the state of the art, in particular the HPPDs of bacteria such as *Pseudomonas* (Rüetschi et al., Eur. J. Biochem., 205, 459-466, 1992, WO 96/38567), of plants such as *Arabidopsis* (WO 96/38567, Genebank AF047834), carrot (WO 96/38567, Genebank 87257), *Avena sativa* (WO 02/046387), wheat (WO 02/046387), *Brachiaria platyphylla* (WO 02/046387), *Cenchrus echinatus* (WO 02/046387), *Lolium rigidum* (WO 02/046387), *Festuca arundinacea* (WO 02/046387), *Setaria faberi* (WO 02/046387), *Eleusine indica* (WO 02/046387), Sorghum (WO 02/046387), Coccicoides (Genebank COITRP), of *Coptis japonica* (WO 06/132270), *Chlamydomonas reinhardtii* (ES 2275365), or of mammals such as mouse or pig.

Inhibition of HPPD leads to uncoupling of photosynthesis, deficiency in accessory light-harvesting pigments and, most importantly, to destruction of chlorophyll by UV-radiation and reactive oxygen species (bleaching) due to the lack of photo protection normally provided by carotenoids (Norris et al. (1995), Plant Cell 7: 2139-2149). Bleaching of photosynthetically active tissues leads to growth inhibition and plant death.

Some molecules which inhibit HPPD, and which bind specifically to the enzyme in order to inhibit transformation of the HPP into homogentisate, have proven to be very effective selective herbicides. At present, most commercially available HPPD inhibitor herbicides belong to one of these three chemical families:

1) the triketones, e.g. sulcotrione, mesotrione; tembotrione; tefuryltrione; bicyclopyrone; benzobicyclon
2) the isoxazoles, e.g. isoxaflutole, or corresponding diketonitriles. In plants, isoxazoles such as isoxaflutole are rapidly converted into diketonitriles, which exhibit the HPPD inhibitor property; and
3) the pyrazolinones, e.g. topramezone, pyrasulfotole and pyrazoxyfen.

These HPPD-inhibiting herbicides can be used against grass and/or broad leaf weeds in crop plants that display metabolic tolerance, such as maize (*Zea mays*) in which they are rapidly degraded (Schulz et al., 1993; Mitchell et al., 2001; Garcia et al., 2000; Pallett et al., 2001). In order to extend the scope of these HPPD-inhibiting herbicides, several efforts have been developed in order to confer to plants, particularly plants without or with an underperforming metabolic tolerance, a tolerance level acceptable under agronomic field conditions.

In that context, it has first been demonstrated that the mere overexpression of a native HPPD enzyme in transformed sensitive plants does provide an effective tolerance to HPPD inhibitors to the transformed plants (WO96/38567).

Another strategy was to mutate the HPPD in order to obtain a target enzyme which, while retaining its properties of catalysing the transformation of HPP into homogentisate, is less sensitive to HPPD inhibitors than is the native HPPD before mutation.

This strategy has been successfully applied for the production of plants tolerant to HPPD-inhibitors, by transforming plants with a gene encoding an HPPD enzyme mutated at one or more positions in its C-terminal part (WO 99/24585). Among the useful mutations in the C-terminal part of HPPD enzymes which can confer tolerance to HPPD-inhibitors, certain mutations were shown to provide increased tolerance to certain diketonitrile herbicides, for example the mutations Pro215Leu, Gly336Glu, Gly336Ile, and Gly336Trp (positions of the mutated amino acid are indicated with reference to the *Pseudomonas* HPPD).

More recently, it has been shown in patent application WO 2009/144079 that certain specific amino acid substitutions at position 336 of the HPPD provide tolerance to certain HPPD inhibitor herbicides in vitro.

US 2010/0197503 also indicates a number of mutations at different positions within or close to the active site of the HPPD taken from *Avena sativa* and examines some of these mutated HPPD enzymes for their inhibition by certain HPPD inhibitors such as sulcotrione.

Despite these successes obtained for the development of plants showing tolerance to some HPPD inhibitors herbicides described above, it is still desirable to develop and/or improve the tolerance of specific plants such as cotton, to more, newer or to several different HPPD inhibitors, particularly HPPD inhibitors belonging to the classes of the triketones (e.g. sulcotrione, mesotrione, tembotrione, tefuryltrione, bicyclopyrone and benzobicyclon), the pyrazolinones (e.g., topramezone, pyrasulfotole and pyrazoxifen) and the isoxazoles (e.g. isoxaflutole) or corresponding diketonitriles. This problem is solved as herein after described in the different embodiments, examples and claims.

These and other problems are solved as described hereinafter in the different detailed embodiments of the invention, as well as in the claims.

SUMMARY OF THE INVENTION

In one embodiment, the invention relates to a method for modifying the genome of a plant cell at a predefined site comprising the steps of
   a. inducing a double stranded DNA break in the vicinity of or at said predefined site, said double stranded break being induced by the introduction into said cell of a double stranded DNA break inducing (DSBI) enzyme which recognizes a recognition sequence in the vicinity of or at said predefined site;
   b. selecting a plant cell wherein said double stranded DNA break has been repaired resulting in a modification in the genome at said preselected site, wherein said modification is selected from
      i. a replacement of at least one nucleotide;
      ii. a deletion of at least one nucleotide;
      iii. an insertion of at least one nucleotide; or
      iv. any combination of i.-iii.;
      characterized in that said predefined site and/or recognition site is located in close proximity to an elite event.

In a particular embodiment the event is GHB119.

In another embodiment, the recognition sequence is comprised within SEQ ID NO: 3 or SEQ ID NO: 4.

The recognition sequence may comprise the nucleotide sequence of SEQ ID NO: 1 or SEQ ID NO: 2.

The invention further provides a method for modifying the genome of a plant cell at a predefined site comprising the steps of
   a. inducing a double stranded DNA break in the vicinity of or at said predefined site, said double stranded break being induced by the introduction into said cell of a double stranded DNA break inducing (DSBI) enzyme which recognizes a recognition sequence in the vicinity of or at said predefined site;
   b. selecting a plant cell wherein said double stranded DNA break has been repaired resulting in a modification in the genome at said preselected site, wherein said modification is selected from
      i. a replacement of at least one nucleotide;
      ii. a deletion of at least one nucleotide;
      iii. an insertion of at least one nucleotide; or
      iv. any combination of i.-iii.;
      characterized in that said recognition site comprises the nucleotide sequence of SEQ ID No. 1 or SEQ ID No. 2.

The DSBI enzyme may be introduced into said cell by the delivery into said cell of a nucleic acid molecule comprising one or more chimeric genes encoding (together) said endonuclease enzyme. The DSBI enzyme may be a single chain meganuclease or a pair of meganucleases which recognizes or recognize in concert said predefined site and induces or induce said double stranded break.

In a particular embodiment, the meganuclease or pair of meganucleases is/are derived from I-CreI and wherein the following amino acids are present in meganuclease unit 1:
   a. S at position 32;
   b. Y at position 33;
   c. Q at position 38;
   d. Q at position 80;
   e. S at position 40;
   f. T at position 42;
   g. R at position 77;
   h. Y at position 68;
   i. Q at position 70;
   j. H at position 75;
   k. T at position 44;
   l. I at position 24;
   m. Q at position 26;
   n. K at position 28;
   o. N at position 30.
   and wherein the following amino acids are present in meganuclease unit 2:
   p. S at position 70;
   q. Q at position 44;
   r. K at position 24;
   s. A at position 26;
   t. K at position 28;
   u. N at position 30;
   v. S at position 32;
   w. Y at position 33;
   x. Q at position 38;
   y. Q at position 80;
   z. S at position 40;
   aa. T at position 42;
   bb. Q at position 77;
   cc. Y at position 68.

The meganuclease or pair of meganucleases may comprises the amino acid sequence of SEQ ID NO. 6 from amino acid position 11-165 and from position 204-360.

The meganuclease or pair of meganucleases may also be encoded by one or more nucleotide sequences which comprises or comprise together the nucleotide sequences of SEQ ID NO 5 from nucleotide position 3120-3584 and from position 3698-4169.

In one embodiment, prior to step b. a repair DNA molecule is delivered into said cell, said repair DNA molecule being used as a template for repair of said double stranded DNA break.

The repair DNA may comprise at least one flanking region comprising a nucleotide sequence having sufficient homology to the upstream or downstream DNA region of said predefined site to allow recombination with said upstream or downstream DNA region. Alternatively, the repair DNA may comprise two flanking regions located on opposite ends of said repair DNA, one of said flanking regions comprising a nucleotide sequence having sufficient homology to the upstream DNA region of said predefined site, the other flanking region comprising a nucleotide sequence having sufficient homology to the downstream sequence of said predefined site to allow recombination between said flanking nucleotide sequences and said upstream and downstream DNA regions.

In a further embodiment, the repair DNA comprises a selectable marker gene and/or a plant expressible gene of interest. The plant expressible gene of interest can be selected from the group of a herbicide tolerance gene, an insect resistance gene, a disease resistance gene, an abiotic stress resistance gene, an enzyme involved in oil biosynthesis, carbohydrate biosynthesis, an enzyme involved in fiber strength or fiber length, an enzyme involved in biosynthesis of secondary metabolites.

In yet another embodiment, plant cell of which the genome was modified at a predefined position is further regenerated into a plant, which also contains the modification at the predefined position. That plant can then be crossed with another plant, resulting in offspring also comprising the genomic modification.

The invention further relates to a plant cell comprising a modification at a predefined site of the genome, obtained by the method as described above. Also encompassed within the invention are; a plant, plant part, seed or propagating material thereof, comprising a modification at a predefined site of the genome, obtained by the method of the invention or consisting essentially of the plant cells of the invention.

Also provided is a method of growing a plant of the invention, i.e. a plant comprising a modification at a predefined site of the genome, comprising the step of applying a chemical to said plant or substrate wherein said plant is grown, as well as a method for producing a plant comprising a modification at a predefined site of the genome, comprising the step of crossing a plant consisting essentially of the plant cells of the invention or a plant of the invention (plant cells and plants comprising the intended genomic modification) with another plant or with itself and optionally harvesting seeds.

In one embodiment, the invention also provides a cotton plant cell, plant part, plant, or seed comprising a chimeric gene comprising
(a) a nucleic acid sequence encoding a protein having HPPD activity, wherein said protein has a tryptophan at a position corresponding to position 336 of SEQ ID NO: 19, wherein said protein provides to said plant tolerance to a field dose of at least 1× of at least one HPPD inhibitor, operably linked to
(b) a plant expressible promoter and optionally
(c) a translational termination and polyadenylation region.

The protein having HPPD activity may have at least 95% sequence identity to the amino acid sequence of SEQ ID NO: 21. The nucleic acid sequence encoding the protein having HPPD activity may be optimized for expression in cotton. The protein may comprise the amino acid sequence of SEQ ID NO: 21 or may be encoded by a nucleic acid comprising the nucleotide sequence of SEQ ID NO: 20 from nt 949 to nt 2025.

The cotton plant cell, plant part, plant, or seed may have a tolerance to a field dose of at least 1.5× of said at least one HPPD inhibitor, or to a field dose of at least 2× of said at least one HPPD inhibitor, or to a field dose of at least 4× of said at least one HPPD inhibitor.

The at least one HPPD inhibitor may be selected from mesotrione, isoxaflutole, topramezone, pyrasulfutole and tembotrione.

The cotton plant cell, plant part, plant, or seed of of the invention may be tolerant to at least two HPPD inhibitors, preferably at least three HPPD inhibitors, more preferably at least four HPPD inhibitors such as at least 5 or at least 6 HPPD inhibitors.

The chimeric gene of the cotton plant cell, plant part, plant, or seed according to the invention may comprise the nucleic acid sequence of SEQ ID NO: 20 from position 88 to position 2714.

The cotton plant cell, plant part, plant or seed of the invention may also comprises at least one further chimeric gene comprising a nucleic acid sequence encoding an enzyme providing to the plant tolerance to a herbicide which is not an HPPD inhibitor or providing tolerance to at least one insect or fungal species.

In another embodiment, the invention provides a method for obtaining a cotton plant or plant cell tolerant to field dose of at least 1× of at least one HPPD inhibitor, comprising
introducing a chimeric gene comprising:
(a) a nucleic acid sequence encoding a protein having HPPD activity, wherein said protein has a tryptophan at a position corresponding to position 336 of SEQ ID NO: 19, wherein said protein provides to said plant tolerance to a field dose of at least 1× of at least one HPPD inhibitor, operably linked to
(b) a plant expressible promoter and optionally
(c) a translational termination and polyadenylation region.

Also provided is a method for controlling weeds in the vicinity of a cotton plant or on a plant field comprising
applying at least one HPPD inhibitor to the vicinity of a cotton plant or to a cotton plant field in a field dose of at least 1×.

In the methods according to the invention the at least one HPPD inhibitor may be selected from mesotrione, isoxaflutole, topramezone, pyrasulfutole and tembotrione. The at least one HPPD inhibitor is applied in a field dose of at least 1.5×, at least 2× or at least 4×.

In a particular embodiment of the methods of the invention the at least one HPPD inhibitor is isoxaflutole and mesotrione, wherein said isofluxatole is applied pre-emergence and said mesotrione is applied post-emergence.

BRIEF DESCRIPTION OF THE DRAWINGS

FIG. 2: Amino acid sequence of the single chain COT-5/6 meganuclease, comprising an SV40 nuclear localization signal (amino acids 1-10), the COT-5 subunit (amino acid 11-165), a linker sequence (amino acids 166-203) and the COT-6 subunit (amino acids 204-360), represented by SEQ ID No. 6.

DESCRIPTION OF DIFFERENT EMBODIMENTS OF THE INVENTION

Figure 1:
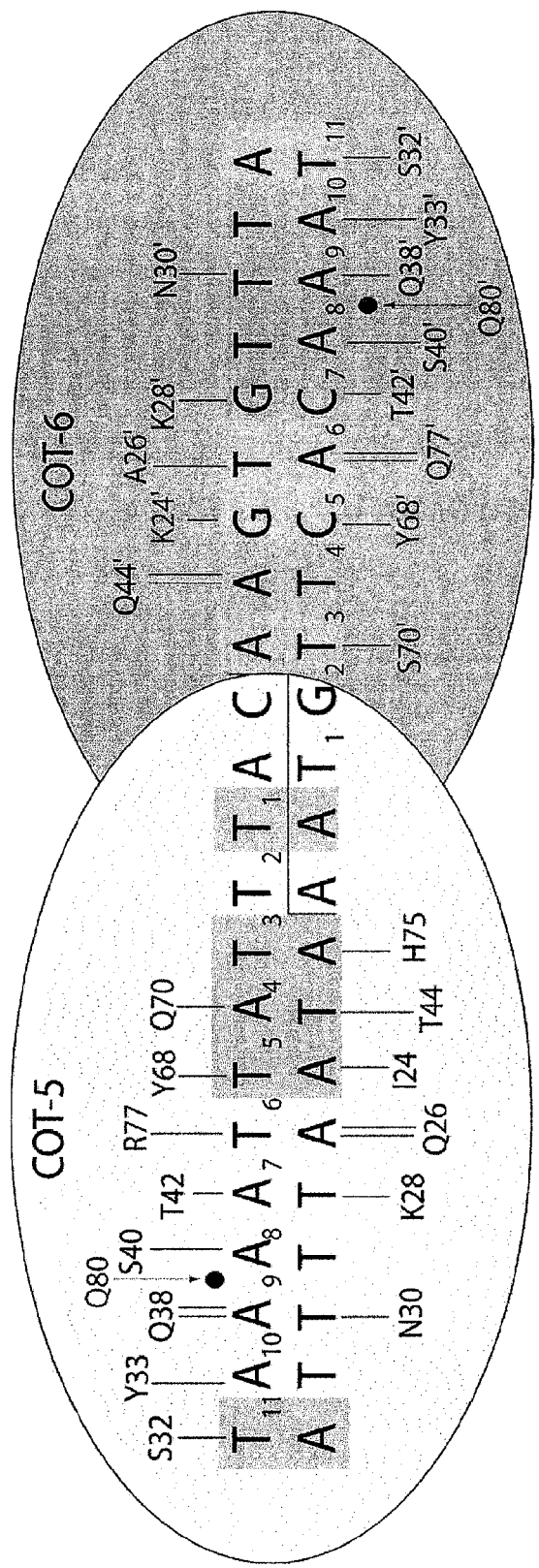
FIG. 1: Schematic representation of the recognition site and interactions with amino acids of the different meganuclease monomeric units COT5 and COT6, represented by SEQ ID No. 1 and SEQ ID No. 2.

The current invention is based on the observation that functional re-designed meganucleases can be obtained which specifically recognize and cleave a nucleotide sequence (SEQ ID No. 1 and SEQ ID No. 2—FIG. 1), which nucleotide sequence is present in close proximity of an existing event, namely cotton event GHB119 (described in 2008/151780, deposit nr ATCC PTA-8398), comprising the Cry2AE gene and the bar gene (conferring Lepidoptera resistance and glufosinate tolerance respectively). Using this specific meganuclease an additional DNA fragment comprising an EPSPS gene and an HPPD gene (conferring tolerance to glyphosate and HPPD inhibiting herbicides respectively) could be inserted within a few kb of the existing GHB119 event, thereby creating a quadruple gene stack which should inherit as a single genetic unit.

A cotton plant was thus generated comprising a chimeric DNA molecule encoding a protein having HPPD activity in which the conserved amino acid corresponding to glycine (Gly or G) at a position corresponding to position 336 of the *Pseudomonas fluorescens* HPPD protein has been replaced by a tryptophan (Trp or W).

It was furthermore surprisingly found that plants, particularly cotton plants, comprising such a chimeric gene leading to the expression of a protein having HPPD activity having a mutation to Trp instead of the conserved native amino acid residue Gly at the position corresponding to position 336 in the amino acid sequence of the protein of *Pseudomonas fluorescens*, whether as a quadruple stack (i.e. targeted) or whether generated by random transformation, showed tolerance to a field dose of at least 1× of several HPPD inhibitor herbicides, such as mesotrione, isoxaflutole, tembotrione, pyrasulfotole and topramezone or any other applicable HPPD inhibitor as listed herein. Surprisingly, the present inventors found that plants, in particular cotton plants, expressing a protein having HPPD activity having a mutation to Trp instead of the conserved native amino acid residue Gly at the position corresponding to position 336 in the amino acid sequence of the protein of *Pseudomonas fluorescens*, showed tolerance to a field dose of at least 1× of several HPPD inhibitors.

There are several advantages of being able to introduce a genomic modification in close proximity to an existing elite event. Firstly, the modification will co-segregate with the earlier event, thereby avoiding complex breeding schemes normally required to combine certain traits conferred by single events. Secondly, the modification will occur in a favorable genomic environment for expression of the desired trait resulting from the modification as the existing elite event is also assumed to show a correct, appropriate and stable spatial and temporal phenotypic expression due to its particular genomic localization, as elaborated below.

Accordingly, in one embodiment, the invention relates to a method for modifying the genome of a plant cell at a predefined site comprising the steps of
a. inducing a double stranded DNA break in the vicinity of or at said predefined site, said double stranded break being induced by the introduction into said cell of an double stranded DNA break inducing (DSBI) enzyme which recognizes a recognition sequence in the vicinity of or at said predefined site;
b. selecting a plant cell wherein said double stranded DNA break has been repaired resulting in a modification in the genome at said preselected site, wherein said modification is selected from
 v. a replacement of at least one nucleotide;
 vi. a deletion of at least one nucleotide;
 vii. an insertion of at least one nucleotide; or
 viii. any combination of i.-iii.;
 characterized in that said predefined site and/or said recognition sequence is/are located in close proximity to an existing elite event.

As used herein, a "double stranded DNA break inducing rare-cleaving endonuclease" is an enzyme capable of inducing a double stranded DNA break at a particular nucleotide sequence, called the "recognition site". Rare-cleaving endonucleases are rare-cleaving in the sense that due to their long recognition sequence (typically about 14-40 nt) they have a very low frequency of cleaving, even in the larger plant genomes, e.g. they cut only 10 times, only 5 times, only 4 times, only three times, only two times or only once per genome. Homing endonucleases constitute a family of such rare-cleaving endonucleases and are sometimes also referred to as meganuclease. They may be encoded by introns, independent genes or intervening sequences, and present striking structural and functional properties that distinguish them from the more classical restriction enzymes, usually from bacterial restriction-modification Type II systems. Their recognition sites have a general asymmetry which contrast to the characteristic dyad symmetry of most restriction enzyme recognition sites. Several homing endonucleases encoded by introns or inteins have been shown to promote the homing of their respective genetic elements into allelic intronless or inteinless sites. By making a site-specific double strand break in the intronless or inteinless alleles, these nucleases create recombinogenic ends, which engage in a gene conversion process that duplicates the coding sequence and leads to the insertion of an intron or an intervening sequence at the DNA level.

A well characterized homing endonuclease is I-SceI. I-SceI is a site-specific endonuclease, responsible for intron mobility in mitochondria in *Saccharomyces cerevisea*. The enzyme is encoded by the optional intron Sc LSU.1 of the 21S rRNA gene and initiates a double stranded DNA break at the intron insertion site generating a 4 bp staggered cut with 3'OH overhangs. The recognition site of I-SceI endonuclease extends over an 18 bp non-symmetrical sequence (Colleaux et al. 1988 *Proc. Natl. Acad. Sci. USA* 85: 6022-6026). The amino acid sequence for I-SceI and a universal code equivalent of the mitochondrial I-SceI gene have been provided by e.g. WO 96/14408. WO 96/14408 further discloses a number of variants of I-SceI protein which are still functional.

PCT application PCT/EP04/013122 (incorporated herein by reference) provides synthetic nucleotide sequence variants of I-SceI which have been optimized for expression in plants.

A list of other rare cleaving DSB inducing enzymes and their respective recognition sites is provided in Table I of WO 03/004659 (pages 17 to 20) (incorporated herein by reference). These include I-Sce I, I-Chu I, I-Dmo I, I-Cre I, I-Csm I, PI-Fli I, Pt-Mtu I, I-Ceu I, I-Sce II, I-Sce III, HO, PI-Civ I, PI-Ctr I, PI-Aae I, PI-BSU I, PI-Dhal, PI-Dra I, PI-May I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I or PI-Tsp I.

Furthermore, methods are available to design custom-tailored rare-cleaving endonucleases that recognize basically any target nucleotide sequence of choice. Briefly, chimeric restriction enzymes can be prepared using hybrids between a zinc-finger domain designed to recognize a specific nucleotide sequence and the non-specific DNA-cleavage domain from a natural restriction enzyme, such as FoId. These enzymes are generally referred to as Zinc finger endonucleases (ZFEs). Such methods have been described e.g. in WO 03/080809, WO94/18313 or WO95/09233 and in Isalan et al., 2001, *Nature Biotechnology* 19, 656-660; Liu et al. 1997, *Proc. Natl. Acad. Sci. USA* 94, 5525-5530). Another way of producing custom-made meganucleases, by selection from a library of variants, is described in WO2004/067736. Custom made meganucleases with altered sequence specificity and DNA-binding affinity may also be obtained through rational design as described in WO2007/047859. Another example of custom-designed rare-cleaving endonucleases include the so-called TALE nucleases, which are based on transcription activator-like effectors (TALEs) from the bacterial genus *Xanthomonas* fused to the catalytic domain of e.g. FOKI. The DNA binding specificity of these TALEs is defined by repeat-variable diresidues (RVDs) of tandem-arranged 34/35-amino acid repeat units, which can be modified to recognize specific target sequences (Christian et al., 2010, Genetics 186: 757-761, WO11/072246, WO10/079430 and WO11/146121. Such custom designed endonucleases are also referred to as a non-naturally occurring endonucleases.

Since the re-designed meganucleases are derived from naturally occurring endonucleases, the available potential recognition sites are not entirely random but appear to have some degree of resemblance to the nucleotide sequence originally recognized by the naturally occurring endonuclease upon which the re-designed meganuclease is based. As stated by Gao et al (2010, *The Plant Journal*, pp 1-11) the structure-based protein design method to modify the DNA-binding characteristics of I-CreI is based on visual inspection of the I-CreI-DNA co-crystal structure leading to a prediction of a a large number of amino acid substitutions that change I-CreI base preference at particular positions in its recognition site. Individual amino acid substitutions were evaluated experimentally, and those that conferred the desired change in base preference were added to a database of mutations that can be "mixed and matched" to generate derivatives of I-CreI that recognize highly divergent DNA sites. In theory, the combinatorial diversity available using the current mutation database is sufficient to target an engineered endonuclease approximately every 1000 bp in a random DNA sequence.

An "event", as used herein, is defined as a (artificial) genetic locus that, as a result of genetic engineering, carries a foreign DNA or transgene comprising at least one copy of a gene of interest or of multiple genes of interest at a particular genomic location. The typical allelic states of an event are the presence or absence of the foreign DNA. An event is characterized phenotypically by the expression of the transgene. At the genetic level, an event is part of the genetic make-up of a plant. At the molecular level, an event can be characterized by the restriction map (e.g., as determined by Southern blotting), by the upstream and/or downstream flanking sequences of the transgene (reflecting the genomic location), the location of molecular markers and/or the molecular configuration of the transgene. Usually transformation of a plant with a transforming DNA comprising at least one gene of interest leads to a population of transformants comprising a multitude of separate events, each of which is unique. An event is characterized by the foreign DNA and at least one of the flanking sequences.

An elite event, as used herein, is an event which is selected from a group of events, obtained by transformation with the same transforming DNA, based on the expression and stability of the transgene(s) and the trait it confers, as well as its compatibility with optimal agronomic characteristics of the plant comprising it. Thus the criteria for elite event selection are one or more, preferably two or more, advantageously all of the following:

a) that the presence of the foreign DNA does not compromise other desired characteristics of the plant, such as those relating to agronomic performance or commercial value (e.g. does not cause an increased susceptibility to disease, does not cause a yield drag, or does not cause increased lodging, etc);

b) that the event is characterized by a well defined molecular configuration which is stably inherited and for which appropriate tools for identity control can be developed;

c) that the gene(s) of interest show(s) a correct, appropriate and stable spatial and temporal phenotypic expression, both in heterozygous (or hemizygous) and homozygous condition of the event, at a commercially acceptable level in a range of environmental conditions in which the plants carrying the event are likely to be exposed in normal agronomic use.

It is furthermore preferred that the foreign DNA is associated with a position in the plant genome that allows easy introgression into desired commercial genetic backgrounds.

The status of an event as an elite event is confirmed by introgression of the elite event in different relevant genetic backgrounds and observing compliance with one, two or all of the criteria e.g. a), b) and c) above.

An "elite event" thus refers to a genetic locus comprising a foreign DNA, which meets the above-described criteria. A plant, plant material or progeny such as seeds can comprise one or more elite events in its genome.

Once one or both of the flanking sequences of the foreign DNA have been sequenced, primers and probes can be developed which specifically recognize this (these) sequence(s) in the nucleic acid (DNA or RNA) of a sample by way of a molecular biological technique. For instance a PCR method can be developed to identify the elite event in biological samples (such as samples of plants, plant material or products comprising plant material). Such a PCR is based on at least two specific "primers", one recognizing a sequence within the 5' or 3' flanking sequence of the elite event and the other recognizing a sequence within the foreign DNA. The primers preferably have a sequence of between 15 and 35 nucleotides which under optimized PCR conditions "specifically recognize" a sequence within the 5' or 3' flanking sequences of the elite event and the foreign DNA of the elite event respectively, so that a specific fragment ("integration fragment" or discriminating amplicon) is amplified from a nucleic acid sample comprising the elite event. This means that only the targeted integration fragment, and no other sequence in the plant genome or foreign DNA, is amplified under optimized PCR conditions.

Transgenic plants containing elite transformation events, or a combination of transformation events, that may be used according to the methods of the invention, include those that are listed for example in the databases for various national or regional regulatory agencies, and include Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US2002120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control—herbicide tolerance, deposited as PTA-6233, described in WO2005/103266 or US2005216969); Event 3006-210-23 (cotton, insect control—herbicide tolerance, deposited as PTA-6233, described in US2007143876 or WO2005/103266); Event 3272 (corn, quality trait, deposited as PTA-9972, described in WO2006098952 or US2006230473); Event 40416 (corn, insect control—herbicide tolerance, deposited as ATCC PTA-11508, described in WO2011/075593); Event 43A47 (corn, insect control—herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US2006162007 or WO2004053062); Event B16 (corn, herbicide tolerance, not deposited, described in US2003126634); Event BPS-CV127-9 (soybean, herbicide tolerance, deposited as NCIMB No. 41603, described in WO2010/080829); Event CE43-67B (cotton, insect control, deposited as DSM ACC2724, described in US2009217423 or WO2006/128573); Event CE44-69D (cotton, insect control, not deposited, described in US20100024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US2006130175 or WO2004039986); Event COT202 (cotton, insect control, not deposited, described in US2007067868 or WO2005054479); Event COT203 (cotton, insect control, not deposited, described in WO2005/054480); Event DAS40278 (corn, herbicide tolerance, deposited as ATCC PTA-10244, described in WO2011/022469); Event DAS-59122-7 (corn, insect control—herbicide tolerance, deposited as ATCC PTA 11384, described in US2006070139); Event DAS-59132 (corn, insect control—herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US2009137395 or WO2008/112019); Event DP-305423-1 (soybean, quality trait, not deposited, described in US2008312082 or WO2008/054747); Event DP-32138-1 (corn, hybridization system, deposited as ATCC PTA-9158, described in US20090210970 or WO2009/103049); Event DP-356043-5 (soybean, herbicide tolerance, deposited as ATCC PTA-8287, described in US20100184079 or WO2008/002872); Event EE-1 (brinjal, insect control, not deposited, described in WO2007/091277); Event FI117 (corn, herbicide tolerance, deposited as ATCC 209031, described in US2006059581 or WO1998/044140); Event GA21 (corn, herbicide tolerance, deposited as ATCC 209033, described in US2005086719 or WO1998/044140); Event GG25 (corn, herbicide tolerance, deposited as ATCC 209032, described in US2005188434 or WO1998/044140); Event GHB119 (cotton, insect control—herbicide tolerance, deposited as ATCC PTA-8398, described in WO2008/151780); Event GHB614 (cotton, herbicide tolerance, deposited as ATCC PTA-6878, described in US2010050282 or WO2007/017186); Event GJ11 (corn, herbicide tolerance, deposited as ATCC 209030, described in US2005188434 or WO1998/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US2004172669 or WO2004/074492); Event JOPLIN1 (wheat, disease tolerance, not deposited, described in US2008064032); Event LL27 (soybean, herbicide tolerance, deposited as NCIMB41658, described in WO2006/108674 or US2008320616); Event LL55 (soybean, herbicide tolerance, deposited as NCIMB 41660, described in WO2006/108675 or US2008196127); Event LLcotton25 (cotton, herbicide tolerance, deposited as ATCC PTA-3343, described in WO2003013224 or US2003097687); Event LLRICE06 (rice, herbicide tolerance, deposited as ATCC-23352, described in U.S. Pat. No. 6,468,747 or WO2000/026345); Event LLRICE601 (rice, herbicide tolerance, deposited as ATCC PTA-2600, described in US20082289060 or WO2000/026356); Event LY038 (corn, quality trait, deposited as ATCC PTA-5623, described in US2007028322 or WO2005061720); Event MIR162 (corn, insect control, deposited as PTA-8166, described in US2009300784 or WO2007/142840); Event MIR604 (corn, insect control, not deposited, described in US2008167456 or WO2005103301); Event MON15985 (cotton, insect control, deposited as ATCC PTA-2516, described in US2004-250317 or WO2002/100163); Event MON810 (corn, insect control, not deposited, described in US2002102582); Event MON863 (corn, insect control, deposited as ATCC PTA-2605, described in WO2004/011601 or US2006095986); Event MON87427 (corn, pollination control, deposited as ATCC PTA-7899, described in WO2011/062904); Event MON87460 (corn, stress tolerance, deposited as ATCC PTA-8910, described in WO2009/111263 or US20110138504); Event MON87701 (soybean, insect control, deposited as ATCC PTA-8194, described in US2009130071 or WO2009/064652); Event MON87705 (soybean, quality trait—herbicide tolerance, deposited as ATCC PTA-9241, described in US20100080887 or WO2010/037016); Event MON87708 (soybean, herbicide tolerance, deposited as ATCC PTA9670, described in WO2011/034704); Event MON87754 (soybean, quality trait, deposited as ATCC PTA-9385, described in WO2010/024976); Event MON87769 (soybean, quality trait, deposited as ATCC PTA-8911, described in US20110067141 or WO2009/102873); Event MON88017 (corn, insect control—herbicide tolerance, deposited as ATCC PTA-5582, described in US2008028482 or WO2005/059103); Event MON88913 (cotton, herbicide tolerance, deposited as ATCC PTA-4854, described in WO2004/072235 or US2006059590); Event MON89034 (corn, insect control, deposited as ATCC PTA-7455, described in WO2007/140256 or US2008260932); Event MON89788 (soybean, herbicide tolerance, deposited as ATCC PTA-6708, described in US2006282915 or WO2006/130436); Event MS11 (oilseed rape, pollination control—herbicide tolerance, deposited as ATCC PTA-850 or PTA-2485, described in WO2001/031042); Event MS8 (oilseed rape, pollination control—herbicide tolerance, deposited as ATCC PTA-730, described in WO2001/041558 or US2003188347); Event NK603 (corn, herbicide tolerance, deposited as ATCC PTA- 2478, described in US2007-292854); Event PE-7 (rice, insect control, not deposited, described in WO2008/114282); Event RF3 (oilseed rape, pollination control—herbicide tolerance, deposited as ATCC PTA-730, described in WO2001/041558 or US2003188347); Event RT73 (oilseed rape, herbicide tolerance, not deposited, described in WO2002/036831 or US2008070260); Event T227-1 (sugar beet, herbicide tolerance, not deposited, described in WO2002/44407 or US2009265817); Event T25 (corn, herbicide tolerance, not deposited, described in US2001029014 or WO2001/051654); Event T304-40 (cotton, insect control—herbicide tolerance, deposited as ATCC PTA-8171, described in US2010077501 or WO2008/122406); Event T342-142 (cotton, insect control, not deposited, described in WO2006/128568); Event TC1507 (corn, insect control—herbicide tolerance, not deposited, described in US2005039226 or WO2004/099447); Event VIP1034 (corn, insect control—herbicide tolerance, deposited as ATCC PTA-3925., described in WO2003/052073), Event 32316 (corn, insect control-herbicide tolerance, deposited as PTA-11507, described in WO2011/084632) and Event 4114 (corn, insect control-herbicide tolerance, deposited as PTA-11506, described in WO2011/084621).

TABLE 1

Overview of transgenic elite events and the nucleotide sequences of the corresponding flanking sequences (all incorporated herein by reference).

| Event name | Plant species | Trait type | Deposit Nr | Patent Reference | | Genomic flanking sequences |
|---|---|---|---|---|---|---|
| 1143-14A | COTTON | INSECT CONTROL | NONE | WO | 2006/128569 | SEQ ID N° 1: nt 1-316 |
| | | | | | | SEQ ID N° 2: nt 319-596 |
| 1143-51B | COTTON | INSECT CONTROL | NONE | WO | 2006/128570 | SEQ ID N° 1: nt 175-589 |
| 1445 | COTTON | HERBICIDE TOLERANCE | NONE | WO | 2002/034946 | SEQ ID N° 7: nt 1-172 (5') |
| | | | | | | SEQ ID N° 8: nt 375-499 (3') |
| 17053 | RICE | HERBICIDE TOLERANCE | ATCC PTA-9843 | WO | 2010/117737 | SEQ ID N° 3: nt 1-574 (5') |
| | | | | | | SEQ ID N° 4: nt 1-635 (3') |
| 17314 | RICE | HERBICIDE TOLERANCE | ATCC PTA-9844 | WO | 2010/117735 | SEQ ID N° 3: nt 1-292 (5') |
| | | | | | | SEQ ID N° 4: nt 1-665 (3') |
| 281-24-236 | COTTON | INSECT CONTROL - HERBICIDE TOLERANCE | ATCC PTA-6233 | WO | 2005/103266 | SEQ ID N° 1: nt 1-2074 (5') |
| | | | | | | SEQ ID N° 1: nt 12749-15490 (3') |
| 3006-210-23 | COTTON | INSECT CONTROL - HERBICIDE TOLERANCE | ATCC PTA-6233 | WO | 2005/103266 | SEQ ID N° 2: nt 1-527 (5') |
| | | | | | | SEQ ID N° 2: nt 8901-9382 (3') |
| 32316 | CORN | INSECT CONTROL - HERBICIDE TOLERANCE | ATCC PTA-11507 | WO | 2011/084632 | SEQ ID N° 6: nt 1-2005 (5') |
| | | | | | | SEQ ID N° 6: nt 13950-15992 (3') |
| 3272 | CORN | QUALITY TRAIT | ATCC PTA-9972 | WO | 2006098952 | SEQ ID N° 5: (1409 nt) ('5) |
| | | | | | | SEQ ID N° 6: (1557 nt) (3') |
| 40416 | CORN | INSECT CONTROL - HERBICIDE TOLERANCE | ATCC PTA-11508 | WO | 2011/075593 | SEQ ID N° 6: nt 1-508 (5') |
| | | | | | | SEQ ID N° 6: nt 12369-13176 (3') |
| 4114 | CORN | INSECT CONTROL - HERBICIDE TOLERANCE | ATCC PTA-11506 | WO | 2011/084621 | SEQ ID N° 6: nt 1-2422 (5') |
| | | | | | | SEQ ID N° 6: nt 14348-16752 (3') |
| 43A47 | CORN | INSECT CONTROL - HERBICIDE TOLERANCE | ATCC PTA-11509 | WO | 2011/075595 | SEQ ID N° 6: nt 1-987 (5') |
| | | | | | | SEQ ID N° 6: nt 12899-14354 (3') |
| 5307 | CORN | INSECT CONTROL | ATCC PTA-9561 | WO | 2010/077816 | SEQ ID N° 5: (1548 nt) (5') |
| | | | | | | SEQ ID N° 6: (1093 nt) (3') |
| ASR-368 | BENT GRASS | HERBICIDE TOLERANCE | ATCC PTA-4816 | WO | 2004053062 | SEQ ID N° 3: nt 1-637 (5') |
| | | | | | | SEQ ID N° 4: nt 249-474 (3') |
| B16 | CORN | HERBICIDE TOLERANCE | NONE | US | 2003126634 | — |
| BPS-CV127-9 | SOYBEAN | HERBICIDE TOLERANCE | NCIMB No. 41603 | WO | 2010/080829 | SEQ ID N° 1: nt 1-1311 (5') |
| | | | | | | SEQ ID N° 1: nt 6070-10656 (3') |
| CE43-67B | COTTON | INSECT CONTROL | DSM ACC2724 | WO | 2006/128573 | SEQ ID N° 1: nt 1-275 (5') |
| | | | | | | SEQ ID N° 2: 134-1198 (3') |
| CE44-69D | COTTON | INSECT CONTROL | NONE | WO | 2006/128571 | SEQ ID N° 1: nt 1-135 (5') |
| | | | | | | SEQ ID N° 2: 272-659 (3') |
| CE46-02A | COTTON | INSECT CONTROL | NONE | WO | 2006/128572 | SEQ ID N° 1: nt 1-266 (5') |
| | | | | | | SEQ ID N° 2: 150-530 (3') |
| COT102 | COTTON | INSECT CONTROL | NONE | WO | 2004/039986 | SEQ ID N° 5: (290 nt) (5') |
| | | | | | | SEQ ID N° 6: (347 nt) (3') |
| COT202 | COTTON | INSECT CONTROL | NONE | WO | 2005/054479 | SEQ ID N° 7: (290 nt) (5') |
| | | | | | | SEQ ID N° 8: (4382 nt) (3') |
| COT203 | COTTON | INSECT CONTROL | NONE | WO | 2005/054480 | SEQ ID N° 7: (290 nt) (5') |
| | | | | | | SEQ ID N° 8: (4382 nt) (3') |
| DAS40278 | CORN | HERBICIDE TOLERANCE | ATCC PTA-10244 | WO | 2011/022469 | SEQ ID N° 29: nt 1-1873 (5') |
| | | | | | | SEQ ID N° 29: nt 6690-8557 (3') |
| DAS-59122-7 | CORN | INSECT CONTROL - HERBICIDE TOLERANCE | ATCC PTA-11384 | US | 2006070139 | SEQ ID N° 19: (2593 nt) (5') |
| | | | | | | SEQ ID N° 20: (1986 nt) (3') |
| DAS-59132 | CORN | INSECT CONTROL - HERBICIDE TOLERANCE | NONE | WO | 2009/100188 | SEQ ID N° 3: nt 118-870 (3') |
| DAS68416 | SOYBEAN | HERBICIDE TOLERANCE | ATCC PTA-10442 | WO | 2011/066384 | SEQ ID N° 1: nt 1-2730 (5') |
| | | | | | | SEQ ID N° 1: nt 9122-10212 (3') |
| DAS68416 | SOYBEAN | HERBICIDE TOLERANCE | ATCC PTA-10442 | WO | 2011/066360 | SEQ ID N° 1: nt 1-2730 (5') |
| | | | | | | SEQ ID N° 1: nt 9122-10212 (3') |
| DP-098140-6 | CORN | HERBICIDE TOLERANCE | ATCC PTA-8296 | WO | 2008/112019 | SEQ ID N° 48: (9423 nt) (5' + insert + 3') |
| DP-305423-1 | SOYBEAN | QUALITY TRAIT | NONE | US | 2008312082 | SEQ ID NO: 5 nt 1-18651 (5' contig1) |
| | | | | | | SEQ ID NO: 5 nt 31580-39,499 (3' contig1) |
| | | | | | | SEQ ID NO: 6 nt 1-12163 (5' contig2) |
| | | | | | | SEQ ID NO: 6 nt 14495-25843 (3' contig3) |
| | | | | | | SEQ ID NO: 7 nt 1-5750 (5' contig3) |

TABLE 1-continued

Overview of transgenic elite events and the nucleotide sequences of the corresponding flanking sequences (all incorporated herein by reference).

| Event name | Plant species | Trait type | Deposit Nr | Patent Reference | Genomic flanking sequences |
|---|---|---|---|---|---|
| | | | | | SEQ ID NO: 7 nt 7814-12465 (3' contig3) |
| | | | | | SEQ ID NO: 8 nt 1-2899 (5' contig4) |
| DP-32138-1 | CORN | HYBRIDIZATION SYSTEM | ATCC PTA-9158 | WO 2009/103049 | SEQ ID NO: 8 nt 7910-10058 (3' contig4) SEQ ID NO: 5 nt 31580-39,499 (3' contig1) |
| DP-356043-5 | SOYBEAN | HERBICIDE TOLERANCE | ATCC PTA-8287 | WO 2008/002872 | SEQ ID NO: 8 nt 1-2899 (5' contig4) |
| EE-1 | BRINJAL | INSECT CONTROL | NONE | WO 2007/091277 | SEQ ID NO: 8 nt 7910-10058 (3' contig4) |
| FI117 | CORN | HERBICIDE TOLERANCE | ATCC 209031 | WO 1998/044140 | — |
| GA21 | CORN | HERBICIDE TOLERANCE | ATCC 209033 | WO 1998/044140 | — |
| GG25 | CORN | HERBICIDE TOLERANCE | ATCC 209032 | WO 1998/044140 | — |
| GHB119 | COTTON | INSECT CONTROL - HERBICIDE TOLERANCE | ATCC PTA-8398 | WO 2008/151780 | SEQ ID N° 11: nt 1-463 (5') SEQ ID N° 2: nt 1-112 (3') |
| GHB614 | COTTON | HERBICIDE TOLERANCE | ATCC PTA-6878 | WO 2007/017186 | SEQ ID N° 1: nt 1-732 (5') SEQ ID N° 2: nt 1-430 (3') |
| GJ11 | CORN | HERBICIDE TOLERANCE | ATCC 209030 | WO 1998/044140 | — |
| GM RZ13 | SUGAR BEET | VIRUS RESISTANCE | NCIMB-41601 | WO 2010/076212 | SEQ ID N° 9: (237 nt) (5') SEQ ID N° 3: (347 nt) (3') |
| H7-1 | SUGAR BEET | HERBICIDE TOLERANCE | NCIMB 41158 or NCIMB 41159 | WO 2004/074492 | SEQ ID N° 5: (3778 nt) (5' + insert + 3') |
| JOPLIN1 | WHEAT | DISEASE TOLERANCE | NONE | US 2008064032 | SEQ ID N° 1: nt 1-1393 (5') SEQ ID N° 2: nt 427-2471 (3') |
| LL27 | SOYBEAN | HERBICIDE TOLERANCE | NCIMB41658 | WO 2006/108674 | SEQ ID N° 1: nt 1-209 (5') SEQ ID N° 2: nt 569-1000 (3') |
| LL55 | SOYBEAN | HERBICIDE TOLERANCE | NCIMB 41660 | WO 2006/108675 | SEQ ID N° 1: nt 1-311 (5') SEQ ID N° 2: nt 510-1880 (3') |
| LLcotton25 | COTTON | HERBICIDE TOLERANCE | ATCC PTA-3343 | WO 2003/013224 | SEQ ID N° 1: nt 1-677 (5') SEQ ID N° 2: nt 180-426 (3') |
| LLRICE06 | RICE | HERBICIDE TOLERANCE | ATCC-23352 | WO 2000/026345 | SEQ ID N° 1: nt 1-92 (5') SEQ ID N° 2: nt 605-1279 (3') |
| LLRICE601 | RICE | HERBICIDE TOLERANCE | ATCC PTA-2600 | US 2008289060 | SEQ ID N° 1: nt 1-603 (5') SEQ ID N° 2: nt 73-607 (3') |
| LLRICE62 | RICE | HERBICIDE TOLERANCE | ATCC-203353 | WO 2000/026356 | SEQ ID N° 1: nt 604-1009 (3') |
| LY038 | CORN | QUALITY TRAIT | ATCC PTA-5623 | WO 2005/061720 | SEQ ID N° 1: nt 1-1781 (5' proximal) SEQ ID N° 9: (1736 nt) (5' distal) SEQ ID N° 2: nt 201-867 (3' proximal) SEQ ID N° 10: (359 nt) (3' distal) |
| MIR162 | CORN | INSECT CONTROL | ATCC PTA-8166 | WO 2007/142840 | SEQ ID N° 46: (1088 nt) (5') SEQ ID N° 48: (1189 nt) (3') |
| MIR604 | CORN | INSECT CONTROL | NONE | WO 2005/103301 | SEQ ID N° 5: (801 nt) (5') SEQ ID N° 6: (1064 nt) (3') |
| MON15985 | COTTON | INSECT CONTROL | ATCC PTA-2516 | WO 2002/100163 | SEQ ID N° 4: 531 (5' MON531) SEQ ID N° 6: (3' MON531) SEQ ID N° 19: (5' MON15985) SEQ ID N° 25: (3' MON15985) |
| MON810 | CORN | INSECT CONTROL | NONE | US 2002102582 | SEQ ID N° 5: (244 nt) (5') SEQ ID N° 6: (606 nt) (3') |
| MON863 | CORN | INSECT CONTROL | ATCC PTA-2605 | WO 2004/011601 | SEQ ID N° 5: (242 nt) (5') SEQ ID N° 6: (224 nt) (3') |
| MON87427 | CORN | POLLINATION CONTROL | ATCC PTA-7899 | WO 2011/062904 | SEQ ID N° 7: (972 nt) (5' + part of transgene) SEQ ID N° 8: (1078 nt) (3' part of transgene) |
| MON87460 | CORN | STRESS TOLERANCE | ATCC PTA-8910 | WO 2009/111263 | SEQ ID N° 5: (1060 nt) (5') SEQ ID N° 6: (1260 nt) (3') |
| MON87701 | SOYBEAN | INSECT CONTROL | ATCC PTA-8194 | WO 2009/064652 | SEQ ID N° 3: nt 1-5747 (5') SEQ ID N° 4: nt 289-2611 (3') |
| MON87705 | SOYBEAN | QUALITY TRAIT - HERBICIDE TOLERANCE | ATCC PTA-9241 | WO 2010/037016 | SEQ ID N° 3: (3458 nt) (5') SEQ ID N° 4: (2515 nt) (3') |
| MON87708 | SOYBEAN | HERBICIDE TOLERANCE | ATCC PTA9670 | WO 2011/034704 | SEQ ID N° 3: nt 1-1126 (5') SEQ ID N° 4: nt 131-1947 (3') |
| MON87754 | SOYBEAN | QUALITY TRAIT | ATCC PTA-9385 | WO 2010/024976 | SEQ ID N° 3: nt 1-942 (5') SEQ ID N° 4: nt 154-1244 (3') |
| MON87769 | SOYBEAN | QUALITY TRAIT | ATCC PTA-8911 | WO 2009/102873 | SEQ ID N° 3: nt 1-978 (5') SEQ ID N° 4: nt 10-939 (3') |
| MON88017 | CORN | INSECT CONTROL - HERBICIDE TOLERANCE | ATCC PTA-5582 | WO 2005/059103 | SEQ ID N° 3: (1461 nt) (5' + part of transgene) SEQ ID N° 4: (3525 nt) (3' + part of transgene) |
| MON88913 | COTTON | HERBICIDE TOLERANCE | ATCC PTA-4854 | WO 2004/072235 | SEQ ID N° 3: (2880 nt) (5' + part of transgene) SEQ ID N° 4: (1675) (3' + part of transgene) |
| MON89034 | CORN | INSECT CONTROL | ATCC PTA-7455 | WO 2007/140256 | SEQ ID N° 3: nt 1-2050 (5') SEQ ID N° 4: nt 1-914 (3') |

TABLE 1-continued

Overview of transgenic elite events and the nucleotide sequences of the corresponding flanking sequences (all incorporated herein by reference).

| Event name | Plant species | Trait type | Deposit Nr | Patent Reference | | Genomic flanking sequences |
|---|---|---|---|---|---|---|
| MON89788 | SOYBEAN | HERBICIDE TOLERANCE | ATCC PTA-6708 | WO | 2006/130436 | SEQ ID N° 3: (1222 nt) (5' + part of T-DNA) SEQ ID N° 4: (1675 nt) (3' + part of T-DNA) |
| MS11 | OILSEED RAPE | POLLINATION CONTROL - HERBICIDE TOLERANCE | ATCC PTA-850 or PTA-2485 | WO | 2001/031042 | SEQ ID N° 8: nt 1-234 (5') SEQ ID N° 10: nt 194-416 (3') |
| MS8 | OILSEED RAPE | POLLINATION CONTROL - HERBICIDE TOLERANCE | ATCC PTA-730 | WO | 2001/041558 | SEQ ID N° 13: 1-867 (5') SEQ ID N° 18: nt 181-537 (3') |
| NK603 | CORN | HERBICIDE TOLERANCE | ATCC PTA-2478 | US | 2004-139493 | SEQ ID N° 7: nt 1-304 (5') SEQ ID N° 8: nt 687-1183 (3') |
| PE-7 | RICE | INSECT CONTROL | NONE | WO | 2008/114282 | SEQ ID N° 7: nt 31-875 (left border) |
| RF3 | OILSEED RAPE | POLLINATION CONTROL - HERBICIDE TOLERANCE | ATCC PTA-730 | WO | 2001/041558 | SEQ ID N° 24: nt 1-881 (5') SEQ ID N° 30: nt 167-1441 (3') |
| RT73 | OILSEED RAPE | HERBICIDE TOLERANCE | NONE | WO | 2002/036831 | SEQ ID N° 7: (5' + part of T-DNA) SEQ ID N° 8: (3' + part of T-DNA |
| T227-1 | SUGAR BEET | HERBICIDE TOLERANCE | NONE | WO | 2002/044407 | FIG. 4.: (right bonder) FIG. 7: (left border) |
| T25 | CORN | HERBICIDE TOLERANCE | NONE | WO | 2001/051654 | SEQ ID N° 6: nt 1-341 (5') SEQ ID N° 10: nt 343-484 (3') |
| T304-40 | COTTON | INSECT CONTROL - HERBICIDE TOLERANCE | ATCC PTA-8171 | WO | 2008/122406 | SEQ ID N° 16: nt 1-563 (5') SEQ ID N° 2: nt 41-452 (3') |
| T342-142 | COTTON | INSECT CONTROL | NONE | WO | 2006/128568 | SEQ ID N° 1: nt 1-162 (5') SEQ ID N° 2: nt 265-570 (3') |
| TC1507 | CORN | INSECT CONTROL - HERBICIDE TOLERANCE | NONE | WO | 2004/099447 | SEQ ID N° 21: (2829 nt) (5') SEQ ID N° 22: (2346 nt) (3') |
| VIP1034 | CORN | INSECT CONTROL - HERBICIDE TOLERANCE | ATCC PTA-3925. | WO | 2003/052073 | SEQ ID N° 11: (716 nt) (5' vip3A) SEQ ID N° 12: (768 nt) (3' vip3A) SEQ ID N° 15: (94 nt) (5' fragmented vip3A) SEQ ID N° 13: (754 nt) (5' pat) SEQ ID N° 14: (94 nt) (3' pat) |

Nt 7060-7976: Ph4a748: sequence including the promoter region of the histone H4 gene of *Arabidopsis thaliana* (Chabouté et al., 1987). As used herein "in close proximity", refers to the predefined site being located at such a distance from the existing transgenic event so as that the introduced modification in the vicinity of or at the predefined site will be genetically linked to the existing event, i.e. they will inherit as a single genetic unit in at least 99% of the cases. Genetic linkage is usually expressed in terms of centimorgans (abbreviated cM). Centimorgan is a unit of recombinant frequency for measuring genetic linkage, defined as that distance between genes for which one product of meiosis in 100 is recombinant, or in other words, the centimorgan is equal to a 1% chance that a marker at one genetic locus on a chromosome will be separated from a marker at a second locus due to crossing over in a single generation. It is often used to infer distance along a chromosome. The number of base-pairs to which cM correspond varies widely across the genome (different regions of a chromosome have different propensities towards crossover) and the species (i.e. the total size of the genome). For instance, the tetraploid cotton genome has been estimated to include about 2200-3000 Mb of DNA distributed across 26 chromosomes, with a total recombinational length of about 400 kb per centimorgan (Smith and Cothren, "Cotton: origin, history, technology and production", p 421). In *A. thaliana*, 1 cM corresponds to approximately 217 kb, while in e.g. *Z. mays* this is about 1460 kb (Mézard C. Meiotic recombination hotspots in plants. Biochem Soc Trans. 2006 August 34:531-4; Civardi et al., The relationship between genetic and physical distances in the cloned a1-sh2 interval of the *Zea mays* L. genome. Proc Natl Acad Sci USA. 1994 91(17):8268-72, p. 8271; from http://bionumbers.hms.harvard.edu/default.aspx). "In close proximity", as used herein, thus refers to at least a 99% chance that the modification and the elite event will inherit as a single genetic unit for at least one generation, and therefore means within 1 cM, within 0.5 cM, within 0.1 cM, within 0.05 cM, within 0.01 cM, within 0.005 cM or within 0.001 cM of the elite event. Relating to base pairs, "in close proximity" can refer to within 5000 kb, within 1000 kb, within 500 kb, within 100 kb, within 50 kb, within 10 kb, within 5 kb, within 4 kb, within 3 kb, within 2 kb, within 1 kb, within 750 bp, or within 500 bp from the existing elite event (depending on the species and location in the genome), e.g. between 1 kb and 10 kb or between 1 kb and 5 kb from the existing elite event.

It will be clear that the predefined site as well as the recognition site should be located such as not to interfere in a negative manner with the existing elite event. Vice versa, the existing elite event should also not negatively influence function of the newly introduced modification, e.g. the functional expression of the newly inserted transgene. It is presently demonstrated that it is possible to make a modification in close proximity to an existing elite event, for example in one of the flanking sequences of the event, which does not negatively affect the existing event (in this case glufosinate tolerance or Lepidoptera resistance) and results in good functional expression of the new modification (e.g. glyphosate tolerance or HPPD inhibitor herbicide tolerance). In one embodiment, "in close proximity" may therefore refer to within one of the flanking sequences of the elite event.

A preferred event in the context of this invention is cotton event GHB119, also known as EE-GH6 (described in 2008/151780, there also referred to as GBH119, deposit nr ATCC PTA-8398). SEQ ID NO. 4 represents the nucleotide sequence of the 5' flanking sequence of the GHB119 event and SEQ ID No. 3 represents the nucleotide sequence of the 3' flanking sequence of the GHB119 event, the latter of which contains a recognition site for the herein described COT-5/6 meganuclease (SEQ ID NO. 1 and its reverse complement SEQ ID NO. 2). The recognition site of SEQ ID No. 1 corresponds to the nucleotide sequence of SEQ ID No. 3 from nucleotide 2114 to 2135. The herein described meganucleases are thus capable of recognizing and cleaving a nucleotide sequence in close proximity of an existing transgenic event, such as GHB119.

Thus, in one embodiment, the predefined site and/or recognition site is/are located in one of the flanking sequences of the elite event. Flanking sequences of elite events which are encompassed in the invention are listed non-exhaustively in table 1. The nucleotide sequences of the flanking sequences of elite event GHB119 are represented by SEQ ID NO: 3 (3') and SEQ ID NO: 4 (5').

In another embodiment, the recognition sequence comprises the nucleotide sequence of SEQ ID NO: 1 or 2.

The redesigned meganucleases described herein are based on the naturally occurring meganuclease I-CreI for use as a scaffold. I-CreI is a homing endonuclease found in the chloroplasts of *Chlamydomonas rheinhardti* (Thompson et al. 1992, Gene 119, 247-251). This endonuclease is a homodimer that recognizes a pseudo-palindromic 22 bp DNA site in the 23SrRNA gene and creates a double stranded DNA break that is used for the introduction of an intron. I-CreI is a member of a group of endonucleases carrying a single LAGLIDADG motif. LAGLIDADG enzymes contain one or two copies of the consensus motif. Single-motif enzymes, such as I-CreI function as homodimers, whereas double-motif enzymes are monomers with two separate domains. Accordingly, when re-designing meganucleases derived from an I-CreI scaffold to recognize a 22 bp nucleotide sequence of interest, two monomeric units are designed, each recognizing a part of the 22 bp recognition site, which are needed in concert to induce a double stranded break at the 22 bp recognition site (WO2007/047859). Concerted action may be achieved by linking the two monomeric units into one single chain meganuclease, or may also be achieved by promoting the formation of heterodimers, as described e.g. in WO2007/047859. Examples of such specifically designed meganucleases are described in e.g. EP10005926.0 and EP10005941.9 (unpublished).

The amino acid sequence of a naturally occurring I-CreI monomer is provided as SEQ ID No. 16. To re-design I-CreI monomeric units such that the heterodimers thereof recognize the nucleotide sequence of SEQ ID No. 1 and/or 2, the following amino acids are present at the mentioned positions in meganuclease unit 1:
  a. S at position 32;
  b. Y at position 33;
  c. Q at position 38;
  d. Q at position 80;
  e. S at position 40;
  f. T at position 42;
  g. R at position 77;
  h. Y at position 68;
  i. Q at position 70;
  j. H at position 75;
  k. T at position 44;
  l. I at position 24;
  m. Q at position 26;
  n. K at position 28;
  o. N at position 30.
and wherein the following amino acids are present in meganuclease unit 2:
  p. S at position 70;
  q. Q at position 44;
  r. K at position 24;
  s. A at position 26;
  t. K at position 28;
  u. N at position 30;
  v. S at position 32;
  w. Y at position 33;
  x. Q at position 38;
  y. Q at position 80;
  z. S at position 40;
  aa. T at position 42;
  bb. Q at position 77;
  cc. Y at position 68.

A schematic representation thereof is provided in FIG. 1. Optionally, a glutamine (Gln/Q) may be present in both subunits at position 47 with respect to the I-CreI amino acid sequence.

The re-designed double stranded break inducing enzyme may comprise, but need not comprise, a nuclear localization signal (NLS), such as the NLS of SV40 large T-antigen [Raikhel, *Plant Physiol.* 100: 1627-1632 (1992) and references therein] [Kalderon et al. *Cell* 39: 499-509 (1984)]. The nuclear localization signal may be located anywhere in the protein, but is conveniently located at the N-terminal end of the protein. The nuclear localization signal may replace one or more of the amino acids of the double stranded break inducing enzyme. It should be noted that if the re-designed meganuclease has been provided with a NLS at the N-terminus of the protein, such as a 10 or 12 amino acid NLS of SV40, the amino acid positions would be shifted (increased) accordingly. Likewise, in the event two monomeric units are linked into a single chain meganuclease, the position of the second unit will also be shifted. The corresponding amino acid positions with regard to the I-CreI amino acid sequence (SEQ ID NO. 16) can also be identified by determining the optimal alignment as described below. It will be clear that in the single chain redesigned meganuclease the order of the units is irrelevant, i.e. whether the above unit 1 and 2 occur indeed within that order in the single amino acid chain or unit 2 precedes unit one in the single amino acid chain does not make a difference in order for the two units combined to be able to recognize the target sequence.

Re-designed meganucleases suitable for the invention may comprise an amino acid sequence as represented by SEQ ID No. 6, which encodes a single chain meganuclease comprising two subunits (amino acids 11-165 and 204-360, respectively) coupled by a linker sequence (amino acids 166-203) and preceded by a nuclear localization sequence (amino acids 1-10). Alternatively such meganucleases may consist of two monomeric units which can cleave the recognition site as a heterodimer. Such a heterodimeric meganuclease may also comprise the amino acids sequences of SEQ ID NO 5. from amino acid position 11-165 and 204-360.

Conveniently, the DSBI enzyme can be provided by expression of a plant expressible recombinant (chimeric) gene(s) encoding such meganuclease(s). To this end, a DNA region comprising a nucleotide sequence encoding a redesigned meganuclease or meganuclease monomeric unit can be operably linked to a plant-expressible promoter and optionally a DNA region involved in transcription termination and polyadenylation and introduced into a plant, plant part or plant cells. The recombinant gene(s) encoding DSBI enzyme may be introduced transiently or stably. The DSBI enzyme may also be introduced into the plant, plant part or plant cell by introducing into the cell an RNA molecule which is translated into the DSBI enzyme. Alternatively, the DSBI enzyme may be introduced into the plant, plant part or plant cell directly as a protein. Methods for the introduction of DNA or RNA molecules or proteins into a plant, plant part, tissue or plant cell are described elsewhere in this application.

For the purpose of the invention, the term "plant-operative promoter" and "plant-expressible promoter" mean a promoter which is capable of driving transcription in a plant, plant tissue, plant organ, plant part, or plant cell. This includes any promoter of plant origin, but also any promoter of non-plant origin which is capable of directing transcription in a plant cell.

Promoters that may be used in this respect are constitutive promoters, such as the promoter of the cauliflower mosaic virus (CaMV) 35S transcript (Hapster et al., 1988, *Mol. Gen. Genet.* 212: 182-190), the CaMV 19S promoter (U.S. Pat. No. 5,352,605; WO 84/02913; Benfey et al., 1989, *EMBO J.* 8:2195-2202), the subterranean clover virus promoter No 4 or No 7 (WO 96/06932), the Rubisco small subunit promoter (U.S. Pat. No. 4,962,028), the ubiquitin promoter (Holtorf et al., 1995, *Plant Mol. Biol.* 29:637-649), T-DNA gene promoters such as the octopine synthase (OCS) and nopaline synthase (NOS) promoters from *Agrobacterium*, and further promoters of genes whose constitutive expression in plants is known to the person skilled in the art.

Further promoters that may be used in this respect are tissue-specific or organ-specific promoters, preferably seed-specific promoters, such as the 2S albumin promoter (Joseffson et al., 1987, *J. Biol. Chem.* 262:12196-12201), the phaseolin promoter (U.S. Pat. No. 5,504,200; Bustos et al., 1989, *Plant Cell* 1. (9):839-53), the legumine promoter (Shirsat et al., 1989, *Mol. Gen. Genet.* 215(2):326-331), the "unknown seed protein" (USP) promoter (Baumlein et al., 1991, *Mol. Gen. Genet.* 225(3):459-67), the napin promoter (U.S. Pat. No. 5,608,152; Stalberg et al., 1996, *Planta* 199:515-519), the *Arabidopsis* oleosin promoter (WO 98/45461), the *Brassica* Bce4 promoter (WO 91/13980), and further promoters of genes whose seed-specific expression in plants is known to the person skilled in the art.

Other promoters that can be used are tissue-specific or organ-specific promoters like organ primordia-specific promoters (An et al., 1996, *Plant Cell* 8: 15-30), stem-specific promoters (Keller et al., 1988, *EMBO J.* 7(12): 3625-3633), leaf-specific promoters (Hudspeth et al., 1989, *Plant Mol. Biol.* 12: 579-589), mesophyl-specific promoters (such as the light-inducible Rubisco promoters), root-specific promoters (Keller et al., 1989, *Genes Dev.* 3: 1639-1646), tuber-specific promoters (Keil et al., 1989, *EMBO J.* 8(5): 1323-1330), vascular tissue-specific promoters (Peleman et al., 1989, *Gene* 84: 359-369), stamen-selective promoters (WO 89/10396, WO 92/13956), dehiscence zone-specific promoters (WO 97/13865), and the like.

Nucleotide sequences encoding DSBI enzymes (re-designed meganucleases) suitable for the invention may comprise the nucleotide sequence of SEQ ID No. 5 from nucleotide position 3120-3584 and the nucleotide sequence of SEQ ID No. 5 from nucleotide position 3698-4169 (excluding linker and NLS). In case of a single chain meganuclease, this may include a linker sequence between the two subunit, such as a linker sequence as encoded by the nucleotide sequence of SEQ ID NO. 5 from nucleotide position 3584-3697. A nucleotide sequence encoding a nuclear localization signal may also be included in the DSBI enzyme encoding nucleotide sequences, such as the nucleotide sequence of SEQ ID NO. 5 from position 3091-3119. To facilitate cloning and other recombinant DNA techniques, it may be advantageous to include an intron functional in plants into the region encoding a meganuclease, particularly a single chain meganuclease.

The DNA region encoding the DSBI enzyme may be optimized for expression in plants by adapting GC content, codon usage, elimination of unwanted nucleotide sequences. The coding region may further be optimized for expression in plants and the synthetic coding region may have a nucleotide sequence which has been designed to fulfill the following criteria:

a) the nucleotide sequence encodes a functional redesigned homing endonuclease as herein described;
b) the codon usage is adapted to the preferred codon usage of the target organism;
c) the nucleotide sequence has a GC content of about 50% to about 60%;
d) the nucleotide sequence does not comprise a nucleotide sequence selected from the group consisting of GATAAT, TATAAA, AATATA, AATATT, GATAAA, AATGAA, AATAAG, AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA and CATAAA;
e) the nucleotide does not comprise a nucleotide sequence selected from the group consisting of CCAAT, ATTGG, GCAAT and ATTGC;
f) the nucleotide sequence does not comprise a sequence selected from the group consisting of ATTTA, AAGGT, AGGTA, GGTA or GCAGG;
g) the nucleotide sequence does not comprise a GC stretch consisting of 7 consecutive nucleotides selected from the group of G or C;
h) the nucleotide sequence does not comprise a AT stretch consisting of 5 consecutive nucleotides selected from the group of A or T; and
i) the nucleotide sequence does not comprise codons coding for Leu, Ile, Val, Ser, Pro, Thr, Ala that comprise TA or CG duplets in positions 2 and 3 (i.e. the nucleotide sequence does not comprise the codons TTA, CTA, ATA, GTA, TCG, CCG, ACG and GCG).

It will also be clear that the terms used to describe the method such as "introduction of a DNA fragment" as well as "regeneration of a plant from the cell" do not imply that such DNA fragment necessarily needs to be introduced by transformation techniques. Indeed, it will be immediately clear to the person skilled in the art that the DNA molecule of interest may also be introduced by breeding or crossing techniques from one plant to another. Thus, "Introducing" in connection with the present application relate to the placing of genetic information in a plant cell or plant by any known means. This can be effected by any method known in the art for transforming RNA or DNA into plant cells, tissues, protoplasts or whole plants or by introgressing said RNA or DNA into plants as described below. More particularly, "introducing" means stably integrating into the plant's genome.

Nucleic acid molecules may be introduced into the plant cells by any method known in the art, including *Agrobacterium*-mediated transformation but also by direct DNA transfer methods. Various methods for DNA delivery into cells/tissues (intact plant cells or partially degraded tissues or plant cells) are known in the art, and include electroporation as illustrated in U.S. Pat. No. 5,384,253; microprojectile bombardment (biolistics) as illustrated in U.S. Pat. Nos. 5,015,580; 5,550,318; 5,538,880; 6,160,208; 6,399,861; and 6,403,865; Cotton transformation by particle bombardment is reported e.g. in WO 92/15675; *Agrobacterium*- mediated transformation as illustrated in U.S. Pat. Nos. 5,635,055; 5,824,877; 5,591,616; 5,981,840; and 6,384,301; *Agrobacterium*-mediated transformation of cotton has been described e.g. in U.S. Pat. No. 5,004,863, in U.S. Pat. No. 6,483,013 and WO2000/71733.; protoplast transformation as illustrated in U.S. Pat. No. 5,508,184, electroporation, chemically-assisted transformation, liposome-mediated transformation (see, e.g., A. Deshayes, et al. (1985) EMBO J. 4:2731-7.), carbon fiber, silicon carbide fiber or aluminum borate fiber (generally termed whiskers) (see, e.g., J. Brisibe, Exp. Bot. 51 (343):187-196 (2000); Dunwell (1999) Methods Mol. Biol. 1 11:375-82; and U.S. Pat. No. 5,464,765), micro-injection (see, e.g., T J. Reich, of al. (1986) Biotechnology 4: 1001-1004) and viral-mediated transformation (see, e.g., S. B. Gelvin, (2005) Nat Biotechnol. 23:684-5, WO 90/12107, WO 03/052108 and WO 2005/098004), bombardment of plant cells with heterologous foreign DNA adhered to particles, ballistic particle acceleration, aerosol beam transformation (U.S. Patent Application No. 20010026941; U.S. Pat. No. 4,945,050; International Publication No. WO 91/00915; U.S. Patent Application No. 2002015066, WO 01/038514; all incorporated herein by reference), Led transformation, PEG transformation, and various other non-particle direct-mediated methods to transfer DNA. As used herein "direct DNA transfer" is any method of DNA introduction into plant cells which does not involve the use of natural *Agrobacterium* spp. and which is capable of introducing DNA into plant cells.

In one embodiment, the nucleic acid molecule(s), such as the repair DNA and/or the DSBI enzyme expression construct, is/are introduced into the plant cell by direct DNA transfer, e.g via particle bombardment. In another embodiment, introduction of DNA molecules takes place using *Agrobacterium*.

In a specific embodiment, the plant cells are comprised within embryogenic callus, preferable friable callus (i.e. the plant cells are callus cells). The term "callus" or "embryogenic callus" refers to a disorganized mass of mainly embryogenic cells and cell clusters produced as a consequence of plant tissue culture. Friable callus refers to callus with a friable texture with the potential to form shoots and roots and eventually regenerate into whole plants. Such callus can further be distinguished by a parrot-green/creamy color, readily dispersed cell clumps in liquid medium, and a nodular shape. Callus can be regenerated/induced from various tissue explants, such as hypocotyl, cotyledon, immature zygotic embryos, leaves, anthers, microspores, petals, ovules, roots, and meristems, stem cells and petioles. Transformation of embryogenic callus for the purpose of targeted genome modification in cotton plants cells is described in U.S. provisional application 61/493,579 and EP11004570.5 (herein incorporated by reference, in particular pages 12-15, paragraphs 40-50, and pages 31-35, examples 2-5).

The capability of inducing a double stranded break at a preselected site opens up several potential applications, i.e. insertion, replacement or deletion of one or more nucleotides. In case a DNA of interest present in the repair DNA molecule is to be inserted into the preselected site, this can occur by either homologous recombination, or by the process of non-homologous end-joining. The double stranded break may also be used to induce the formation of small deletions or insertions at the preselected site, thereby potentially inactivating a gene or regulatory element comprising the nucleotide sequence of the preselected site. The double stranded break at the preselected site will also facilitate replacement of a DNA region in the vicinity of that site for a DNA of interest using a repair DNA, e.g. as described in WO 06/105946, WO08/037436 or WO08/148559.

If the double stranded DNA break induction is accompanied by the introduction of a repair DNA molecule which is used as a template, the double stranded break repair can occur basically in three ways. The repair DNA can be integrated into the genomic DNA at the DSB site by non-homologous end joining at both ends, or if one or two flanking regions with homology to the up- and/or downstream regions of the preselected site (the homology regions) are present in the repair DNA, integration of the repair DNA can also occur (partly) through homologous recombination. As such, the double stranded break at the preselected site will also facilitate replacement of a DNA region in the vicinity of that site for a DNA region of interest e.g. as described in WO 06/105946, WO08/037436 or WO08/148559.

To insert a DNA of interest by homologous recombination at the preselected site, the repair DNA may comprise at least one flanking DNA region having a nucleotide sequence which is similar to the nucleotide sequence of the DNA region upstream or downstream of the preselected site. The foreign DNA may also comprise two flanking DNA regions, located on opposite ends of the molecule and which have sufficient homology to nucleotide sequence of the DNA region upstream and downstream of the preselected site respectively to allow recombination between said flanking regions and said upstream and downstream region.

As used herein "a flanking DNA region" is a DNA region in the repair DNA with a nucleotide sequence having homology (i.e. high sequence identity) to the DNA regions respectively upstream or downstream of the target DNA sequence or preselected site (the homology regions). This allows to better control the insertion of DNA of interest. Indeed, integration by homologous recombination will allow precise joining of the DNA of interest to the plant nuclear genome up to the nucleotide level.

To have sufficient homology for recombination, the flanking DNA regions of the repair DNA may vary in length, and should be at least about 10 nucleotides in length. However, the flanking region may be as long as is practically possible (e.g. up to about 100-150 kb such as complete bacterial artificial chromosomes (BACs). Preferably, the flanking region will be about 50 bp to about 2000 bp. Moreover, the regions flanking the DNA of interest need not be identical to the homology regions (the DNA regions flanking the preselected site) and may have between about 80% to about 100% sequence identity, preferably about 95% to about 100% sequence identity with the DNA regions flanking the preselected site. The longer the flanking region, the less stringent the requirement for homology. Furthermore, it is preferred that the sequence identity is as high as practically possible in the vicinity of the DSB. Furthermore, to achieve exchange of the target DNA sequence without changing the DNA sequence of the adjacent DNA sequences, the flanking DNA sequences should preferably be identical to the upstream and downstream DNA regions flanking the preselected site or the target DNA sequence to be exchanged. The same criteria apply for recombination between the upstream and downstream region bearing homology to each other to remove the intervening DNA sequences by intrachromosomal homologous recombination.

Moreover, the flanking region(s) of the repair DNA do not need to have homology to the regions immediately flanking the preselected site, but may have homology to a DNA region of the nuclear genome further remote from that preselected site. Insertion of the DNA of interest will then result in a removal of the target DNA between the preselected insertion site and the DNA region of homology. In other words, the target DNA located between the homology regions (i.e. the genomic regions with homology to the flanking regions of the foreign repair DNA) will be substituted for the DNA of interest located between the two flanking regions of the repair DNA. When the repair DNA consists of the two flanking regions only, i.e. lacking any intervening sequences (DNA of interest), this approach can be used to specifically delete the genomic region located between the two homology regions.

As used herein "a preselected site" or "predefined site" indicates a particular nucleotide sequence in the plant genome (e.g. the nuclear genome) located in or near the target DNA sequence at which location it is desired to insert, replace or delete one or more nucleotides. A person skilled in the art would be able to either choose a double stranded DNA break inducing ("DSBI") enzyme recognizing the selected target nucleotide sequence or engineer such a DSBI endonuclease. Alternatively, a DSBI enzyme recognition site may be introduced into the plant genome using any conventional transformation method or by conventional breeding using a plant line having a DSBI endonuclease recognition site in its genome, and any desired DNA may afterwards be introduced into that preselected site.

In a further embodiment, the invention provides the use of a DSBI enzyme, such as a non-naturally occurring DSBI enzyme as described above, to modify the genome of a plant cell in the proximity of an existing elite event.

As used herein "located in the vicinity" refers to the site of double DNA stranded break induction, i.e. the recognition site of the DSBI enzyme, being located at a distance of 100 bp, 250 bp, 500 bp, 1 kbp, 2 kbp, 3 kbp, 4 kbp, 5 kbp to 10 kbp from the predefined site, i.e. the site in the genomic DNA which is to be modified (the target site).

The DNA of interest to be inserted may also comprise a selectable or screenable marker, which may or may not be removed after insertion.

"Selectable or screenable markers" as used herein have there usual meaning in the art and include, but are not limited to plant expressible phosphinotricin acetyltransferase, neomycine phosphotransferase, glyphosate oxidase, glyphosate tolerant EPSP enzyme, nitrilase gene, mutant acetolactate synthase or acetohydroxyacid synthase gene, β-glucoronidase (GUS), R-locus genes, green fluorescent protein and the likes.

The selection of the plant cell or plant wherein the selectable or screenable marker and the rest of the DNA of interest has been introduced by homologous recombination through the flanking DNA regions can e.g. be achieved by screening for the absence of sequences present in the transforming DNA but located outside of the flanking DNA regions. Indeed, presence of sequences from the transforming DNA outside the flanking DNA regions would indicate that the origination of the transformed plant cells is by random DNA insertion. To this end, selectable or screenable markers may be included in the transforming DNA molecule outside of the flanking DNA regions, which can then be used to identify those plant cells which do not have the selectable or screenable markers located outside of the transforming DNA and which may have arisen by homologous recombination through the flanking DNA regions. Alternatively, the transforming DNA molecule may contain selectable markers outside the flanking DNA regions that allow selection for the absence of such genes (negative selectable marker genes).

It will be clear that the methods according to the invention allow insertion of any DNA of interest including DNA comprising a nucleotide sequence with a particular nucleotide sequence signature e.g. for subsequent identification, or DNA comprising (inducible) enhancers or silencers, e.g. to modulate the expression of the existing elite event. The DNA of interest may also comprise one or more plant expressible gene(s) of interest including but not limited to a herbicide tolerance gene, an insect resistance gene, a disease resistance gene, an abiotic stress resistance gene, an enzyme involved in oil biosynthesis or carbohydrate biosynthesis, an enzyme involved in fiber strength and/or length, an enzyme involved in the biosynthesis of secondary metabolites. Particular mention may be made of herbicide-tolerance genes conferring tolerance to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, and WO 99/24586, WO 2009/144079, WO 2002/046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshydrogenase (PDH) activity in addition to a gene encoding an HPPD-tolerant enzyme, as described in WO 2004/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

In particular embodiments, the invention discloses a cotton plant cell, plant part, plant, or seed comprising a chimeric gene comprising (a) a nucleic acid sequence encoding a protein having HPPD activity, wherein said protein has a tryptophan at a position corresponding to position 336 of SEQ ID NO: 19, wherein said protein provides to said plant tolerance to a field dose of at least 1× of at least one HPPD inhibitor, operably linked to (b) a plant expressible promoter and optionally (c) a translational termination and polyadenylation region.

It will be understood that the cotton plant cell, plant part, plant, or seed comprising a chimeric gene comprising (a) a nucleic acid sequence encoding a protein having HPPD activity according to the invention does not need to be generated according to the methods described herein above for the targeted modification of the genome of a plant or plant cell, but may also be created by random transformation with the chimeric gene or by traditional breeding processes, as described elsewhere in this application.

The term "a protein having HPPD activity" refers to a protein which catalyzes the reaction converting para-hydroxyphenylpyruvate (abbreviated herein as HPP), a tyrosine degradation product, into homogentisate (abbreviated herein as HG).

The catalytic activity of a protein having HPPD activity may be defined by various methods well-known in the art. WO 2009/144079 describes various suitable screening methods. Initial screens may be performed with chimeric genes comprising the nucleic acid encoding the HPPD protein described herein being expressed in bacteria, such as a complementation assay in e.g. *E. coli* (WO08/124495). Further and more elaborate screens may be carried out in plant cells or plants expressing the HPPD protein disclosed herein.

The same screenings may also be used when examining whether an HPPD protein provides to a plant such as a cotton plant tolerance to a field dose of at least 1× of at least one HPPD inhibitor as described further below, with the difference that said HPPD inhibitor is added in addition to an HPPD substrate. HPPD inhibitors which may be tested include isoxaflutole, tembotrione, mesotrione, pyrasulfotole, bicyclopyrone, topramezone, tefuryltrione and sulcotrione and other HPPD inhibitors mentioned in this application. A screening method which is simple to implement is (a) to determine the dose of an HPPD inhibitor which does not inhibit the protein having HPPD activity according to the invention, such as that of SEQ ID NO: 3 which, e.g. for in vitro or cell culture experiments, should be a dose corresponding to a field dose of at least 1×, at least 2× or even at least 3× or at least 4× of an HPPD inhibitor of choice; (b) to subject plant cells, plant parts or plants each comprising a chimeric gene according to the invention, wherein the nucleic acid encoding a protein having HPPD activity is a protein as described above, to this dose, and thereafter (c) to isolate the plant cells, plant parts or plants which have withstood this otherwise lethal dose. At the same time or alternatively, the damage to the aerial parts of said plant parts or plants upon treatment with said inhibitor, such as the extent of chlorosis, bleaching and/or necrosis, may be assessed and scored. Scoring may be effected e.g. as done on the appended examples or as described below.

A position corresponding to position 336 of SEQ ID NO: 19 refers to the amino acid sequence of HPPD proteins comprising an amino acid sequence other than that of SEQ ID NO: 19, having a similar or the same overall structure and, accordingly, also having an amino acid position corresponding to position 336 of SEQ ID NO: 19 but, depending on the length of the amino acid sequence, possibly at a different position. The corresponding position in other HPPD proteins can be determined by aligning the sequences of these proteins with SEQ ID NO: 19 as described above.

In one example of the plant cell, plant part, plant or seed described herein said nucleic acid sequence encoding a protein having HPPD activity comprises the nucleotide sequence of SEQ ID NO: 20 from nt 949-2025 or a nucleic acid sequence having at least 70%, at least 80%, at least 90%, at least 95%, at least 98% or at least 99% sequence identity thereto, wherein said protein provides to a plant tolerance to a field dose of at least 1× of at least one HPPD inhibitor. Sequences falling within this definition include those which encode the amino acid sequence of SEQ ID NO: 21 or an amino acid sequence with at least 70%, at least 80%, at least 90%, at least 95%, at least 98% or at least 99% sequence identity to SEQ ID NO:21.

Also included are fragments of said SEQ ID NO: 20 from nt 949-2025 as long as the protein encoded thereby provides to a plant tolerance to a field dose of at least 1× of at least one HPPD inhibitor. Such fragments comprise for example at least 300, at least 400, at least 500, at least 600, at least 700, at least 800, at least 900 or at least 1000 nucleotides. In one example, any of the above described fragments include a nucleic acid sequence encoding an HPPD protein comprising a tryptophan at a position equivalent to position 336 of SEQ ID NO: 19. In another example, said fragments include in addition at least the first five, first ten, first 20, first 30 amino acids N- and/or C-terminal of said tryptophan.

Accordingly, in one example of the plant cell, plant part, plant or seed described herein said amino acid sequence of a protein having HPPD activity comprises the amino acid sequence of SEQ ID NO: 21 or an amino acid sequence having at least 90%, at least 95%, at least 96%, at least 97%, at least 98% or at least 99% sequence identity thereto, wherein said protein comprises the above amino acid substitution and provides to said plant tolerance to a field dose of at least 1× of at least one HPPD inhibitor. Also included are fragments of said SEQ ID NO: 21 as long said protein having HPPD activity comprises the above amino acid substitution and provides to a plant tolerance to a field dose of at least 1× of at least one HPPD inhibitor. Such fragments comprise for example at least 100 amino acids, at least 150 amino acids, at least 200 amino acids, at least 250 amino acids, at least 300 amino acids.

As a regulatory sequence which functions as a promoter in plant cells and plants, use may be made of any promoter sequence of a gene which is naturally expressed in plants, in particular a promoter which is expressed especially in the leaves of plants, such as for example "constitutive" promoters of bacterial, viral or plant origin.

A plant expressible promoter can be a constitutive promoter, i.e. a promoter capable of directing high levels of expression in most cell types (in a spatio-temporal independent manner). Examples of plant expressible constitutive promoters include promoters of bacterial origin, such as the octopine synthase (OCS) and nopaline synthase (NOS) promoters from *Agrobacterium*, but also promoters of viral origin, such as that of the cauliflower mosaic virus (CaMV) 35S transcript (Hapster et al., 1988, Mol. Gen. Genet. 212: 182-190) or 19S RNAs genes (Odell et al., 1985, Nature. 6; 313(6005):810-2; U.S. Pat. No. 5,352,605; WO 84/02913; Benfey et al., 1989, EMBO J. 8:2195-2202), the enhanced 2×35S promoter (Kay at al., 1987, Science 236:1299-1302; Dada et al. (1993), Plant Sci 94:139-149) promoters of the cassava vein mosaic virus (CsVMV; WO 97/48819, U.S. Pat. No. 7,053,205), 2×CsVMV (WO2004/053135) the circovirus (AU 689 311) promoter, the sugarcane bacilliform badnavirus (ScBV) promoter (Samac et al., 2004, Transgenic Res. 13(4):349-61), the figwort mosaic virus (FMV) promoter (Sanger et al., 1990, Plant Mol Biol. 14(3):433-43), the subterranean clover virus promoter No 4 or No 7 (WO 96/06932) and the enhanced 35S promoter as described in U.S. Pat. No. 5,164,316, U.S. Pat. No. 5,196, 525, U.S. Pat. No. 5,322,938, U.S. Pat. No. 5,359,142 and U.S. Pat. No. 5,424,200. Among the promoters of plant origin, mention will be made of the promoters of the plant ribulose-biscarboxylase/oxygenase (Rubisco) small subunit promoter (U.S. Pat. No. 4,962,028; WO99/25842) from *zea mays* and sunflower, the promoter of the *Arabidopsis thaliana* histone H4 gene (Chabouté et al., 1987), the ubiquitin promoters (Holtorf et al., 1995, Plant Mol. Biol. 29:637-649, U.S. Pat. No. 5,510,474) of Maize, Rice and sugarcane, the Rice actin 1 promoter (Act-1, U.S. Pat. No. 5,641,876), the histone promoters as described in EP 0 507 698 A1, the Maize alcohol dehydrogenase 1 promoter (Adh-1) (from http://www.patentlens.net/daisy/promoters/242.html)). Also the small subunit promoter from *Chrysanthemum* may be used if that use is combined with the use of the respective terminator (Outchkourov et al., Planta, 216: 1003-1012, 2003).

Alternatively, a promoter sequence specific for particular regions, tissues or organs of plants can be used to express the HPPD protein disclosed herein. Promoters that can be used are tissue-specific or organ-specific promoters like organ primordia-specific promoters (An et al., 1996, Plant Cell 8:

15-30), stem-specific promoters (Keller et al., 1988, EMBO J. 7(12): 3625-3633), mesophyl-specific promoters (such as the light-inducible Rubisco promoters), root-specific promoters (Keller et al., 1989, Genes Dev. 3: 1639-1646), vascular tissue-specific promoters (Peleman et al., 1989, Gene 84: 359-369), and the like.

Use may also be made of an inducible promoter advantageously chosen from the phenylalanine ammonia lyase (PAL), HMG-CoA reductase (HMG), chitinase, glucanase, proteinase inhibitor (PI), PRI family gene, nopaline synthase (nos) and vspB promoters (U.S. Pat. No. 5,670,349, Table 3), the HMG2 promoter (U.S. Pat. No. 5,670,349), the apple beta-galactosidase (ABGI) promoter and the apple aminocyclopropane carboxylate synthase (ACC synthase) promoter (WO 98/45445).

According to the invention, use may also be made, in combination with the promoter, of other regulatory sequences, which are located between the promoter and the coding sequence, such as transcription activators ("enhancers"), for instance the translation activator of the tobacco mosaic virus (TMV) described in Application WO 87/07644, or of the tobacco etch virus (TEV) described by Carrington & Freed 1990, J. Virol. 64: 1590-1597, for example.

Other regulatory sequences that enhance functional expression and thereby herbicide tolerance may also be located within the chimeric gene. One example of such regulatory sequences are introns. Introns are intervening sequences present in the pre-mRNA but absent in the mature RNA following excision by a precise splicing mechanism. The ability of natural introns to enhance gene expression, a process referred to as intron-mediated enhancement (IME), has been known in various organisms, including mammals, insects, nematodes and plants (WO 07/098042, p 11-12). IME is generally described as a posttranscriptional mechanism leading to increased gene expression by stabilization of the transcript. The intron is required to be positioned between the promoter and the coding sequence in the normal orientation. However, some introns have also been described to affect translation, to function as promoters or as position and orientation independent transcriptional enhancers (Chaubet-Gigot et al., 2001, Plant Mol Biol. 45(1):17-30, p 27-28).

Examples of genes containing such introns include the 5' introns from the rice actin 1 gene (see U.S. Pat. No. 5,641,876), the rice actin 2 gene, the maize sucrose synthase gene (Clancy and Hannah, 2002, Plant Physiol. 130(2):918-29), the maize alcohol dehydrogenase-1 (Adh-1) and Bronze-1 genes (Callis et al. 1987 Genes Dev. 1(10):1183-200; Mascarenhas et al. 1990, Plant Mol Biol. 15(6):913-20), the maize heat shock protein 70 gene (see U.S. Pat. No. 5,593,874), the maize shrunken 1 gene, the light sensitive 1 gene of *Solanum tuberosum*, and the heat shock protein 70 gene of *Petunia hybrida* (see U.S. Pat. No. 5,659,122), the replacement histone H3 gene from alfalfa (Keleman et al. 2002 Transgenic Res. 11(1):69-72) and either replacement histone H3 (histone H3.3-like) gene of *Arabidopsis thaliana* (Chaubet-Gigot et al., 2001, Plant Mol Biol. 45(1):17-30).

Other suitable regulatory sequences include 5' UTRs. As used herein, a 5'UTR, also referred to as leader sequence, is a particular region of a messenger RNA (mRNA) located between the transcription start site and the start codon of the coding region. It is involved in mRNA stability and translation efficiency. For example, the 5' untranslated leader of a *petunia* chlorophyll a/b binding protein gene downstream of the 35S transcription start site can be utilized to augment steady-state levels of reporter gene expression (Harpster et al., 1988, Mol Gen Genet. 212(1):182-90). WO95/006742 describes the use of 5' non-translated leader sequences derived from genes coding for heat shock proteins to increase transgene expression.

The chimeric gene may also comprise a transcription termination or polyadenylation sequence operable in plant cells. As a transcription termination or polyadenylation sequence, use may be made of any corresponding sequence of bacterial origin, such as for example the nos terminator of *Agrobacterium tumefaciens*, of viral origin, such as for example the CaMV 35S terminator, or of plant origin, such as for example a histone terminator as described in published Patent Application EP 0 633 317 A1.

In connection with the present application, the expression of chimeric genes conferring tolerance to at least one HPPD inhibitor in cotton may be further enhanced by optimizing the sequence encoding the protein to be expressed in cotton, thereby taking into account, inter alia, the codon usage of cotton. Accordingly, the nucleic acid sequence encoding the HPPD protein disclosed herein may be optimized for expression in cotton, e.g. by codon optimization (available e.g. via www.entelechon.com).

An example of a cotton codon-optimized nucleic acid sequence encoding a protein having HPPD activity disclosed herein is represented by SED ID No. 20 from nt 949-2025. The protein having HPPD activity disclosed herein may be encoded by the nucleic acid sequence of SEQ ID NO: 20 from nt 949-2025 or have the amino acid sequence of SEQ ID NO: 21. In one example, said chimeric gene comprises or consists of the nucleic acid sequence of SEQ ID NO: 20 from position 88 to position 2714.

Tolerance to at least one HPPD inhibitor as observed in the plant cell, plant part, plant or seed disclosed herein is caused by the protein having HPPD activity disclosed herein and introduced into said plant cell, plant part, plant which provides to said plant cell, plant part, plant or seed said tolerance to at least one HPPD inhibitor.

The terms "tolerance" or "tolerant" denote the reduced or complete lack of susceptibility of a plant expressing the protein having HPPD activity disclosed herein to substances, particularly herbicides, which inhibit HPPD proteins, optionally in comparison with the plant's own HPPD protein. More specifically, said terms mean the relative levels of inherent tolerance, i.e. reduced or complete lack of susceptibility as described above, of the protein having HPPD activity screened according to a visible indicator phenotype of the strain or plant transformed with a nucleic acid comprising the gene coding for the respective protein in the presence of different concentrations of an HPPD inhibitor. The HPPD inhibitor may be selected from any available HPPD inhibitors.

Usually, application of an HPPD inhibitor to plants not expressing an HPPD enzyme providing tolerance to said HPPD inhibitor results in serious damage of the aerial parts of the plant shortly after application, whereas no or only minor damage is observed in plants expressing an HPPD protein according to the invention or other HPPD proteins believed to provide tolerance. Accordingly, the tolerance observed for said at least one HPPD inhibitor provides plants expressing the HPPD protein according to the invention and treated with at least one HPPD inhibitor with agronomical advantages as compared to plants not expressing said HPPD protein or expressing a different HPPD protein. Although the plants of the invention may show some minor damage after herbicide treatment, said plants recover a short time after treatment. Therefore, plants expressing the HPPD protein of the invention, when treated, preferably do not have a reduced agronomical performance, e.g. do not display a reduced yield, compared to untreated plants.

At present, most commercially available HPPD inhibitors are attributed to one of these four chemical families:

1) the triketones, e.g. sulcotrione [i.e. 2-[2-chloro-4-(methylsulfonyl)benzoyl]-1,3-cyclohexanedione], mesotrione [i.e. 2-[4-(methylsulfonyl)-2-nitrobenzoyl]-1,3-cyclohexanedione]; tembotrione [i.e. 2-[2-chloro-4-(methylsulfonyl)-3-[(2,2,2,-tri-fluoroethoxy)methyl] benzoyl]-1,3-cyclo-hexanedione]; tefuryltrione [i.e. 2-[2-chloro-4-(methylsulfonyl)-3-[[(tetrahydro-2-furanyl) methoxy]methyl]benzoyl]-1,3 cyclohexanedione]]; bicyclopyrone [i.e. 4-hydroxy-3-[[2-[(2-methoxyethoxy)methyl]-6-(trifluoromethyl)-3-pyridinyl]carbonyl]bicyclo [3.2.1]oct-3-en-2-one]; benzobicyclone [i.e. 3-(2-chloro-4-mesylbenzoyl)-2-phenylthiobicyclo [3.2.1]oct-2-en-4-one];

2) The isoxazoles, e.g. isoxaflutole [i.e. (5-cyclopropyl-4-isoxazolyl)[2-(methylsulfonyl)-4-(trifluoromethyl)phenyl]methanone] or corresponding diketonitriles; and 3) the pyrazolinones, e.g. topramezone [i.e. [3-(4,5-dihydro-3-isoxazolyl)-2-methyl-4-(methylsulfonyl)phenyl](5-hydroxy-1-methyl-1H-pyrazol-4-yl)methanone], pyrasulfotole [(5-hydroxy-1,3-dimethylpyrazol-4-yl(2-mesyl-4trifluaromethylphenyl) methanone]; pyrazoxyfen [2-[4-(2,4-dichlorobenzoyl)-1,3-dimethylpyrazol-5-yloxy] acetophenone].

Further compound classes of HPPD inhibitors useful in the present invention are the N-(tetrazol-5-yl)- and N-(triazol-5-yl)arylcarboxamides as disclosed in PCT/EP2011/064820 and the N-(1,2,5-Oxadiazol-3-yl)benzamides as disclosed in WO2011/035874.

In one example, the at least one HPPD inhibitor is selected from isoxaflutole, tembotrione, mesotrione, pyrasulfotole and topramezone or any other applicable HPPD inhibitor or HPPD herbicide such as the ones listed herein.

Dose responses and relative shifts in dose responses associated with these indicator phenotypes (growth inhibition, chlorosis, bleaching, leaf damage in general, wilting, necrosis, herbicidal effect etc) are conveniently expressed in terms, for example, of GR50 (concentration for 50% reduction of growth) or MIC (minimum inhibitory concentration) values where increases in values correspond to increases in inherent tolerance of the expressed HPPD, in the normal manner based upon plant damage (such as damage of the aerial parts of the plant, which may manifest in bleaching, chlorosis and/or necrosis), meristematic bleaching symptoms etc. at a range of different concentrations of herbicides. These data can be expressed in terms of, for example, GR50 values derived from dose/response curves having "dose" plotted on the x-axis and "percentage kill", "herbicidal effect", "numbers of emerging green plants" etc. plotted on the y-axis where increased GR50 values correspond to increased levels of inherent tolerance of the expressed HPPD. Herbicides can be applied pre-emergence or post-emergence, as described in the appended examples. Alternatively, plants can be evaluated for damage of their green parts or leaves based on the relevant indicator phenotypes as mentioned above, e.g. on a scale of 0-100, where 0% indicates no damage and 100% indicated complete bleaching, chlorosis, necrosis and/or wilting etc.

As used herein "pre-emergence", refers to the application of a herbicide, e.g. the at least one HPPD inhibitor, prior to the emergence above the surface of the soil or growth medium of the seedlings grown from the sowed seeds, e.g. just prior to or at the time of sowing of the seeds, or just after sowing, to the soil or growth medium wherein the seeds are sown. As used herein "post-emergence", refers to the application of the herbicide to the plant and the soil or growth medium after the emergence of the seedlings, for instance at the 2-3 leaf-stage or later.

The plant cell, plant part, plant or seed comprising the chimeric HPPD gene as disclosed herein is tolerant to a field dose of at least 1× of at least one HPPD inhibitor. The at least one HPPD inhibitor can be applied at the pre-emergence stage and/or at the post-emergence stage.

As used herein "1×", refers to a normal, single field dose of an HPPD-inhibitor, such as an HPPD-inhibiting herbicide or a formulation comprising an HPPD inhibitor, indicated in g a.i./ha, whereby a.i. stands for active ingredient, as commercially used. Field doses may differ depending on e.g. the HPPD inhibitor used, the crop to which it is applied and the conditions of application, e.g the type of soil on which the crop is grown and the weed expected to be present. Field doses of 1× of commercial products are stated on the product label. Depending on product and label recommendations, commercial 1× field rates may vary between e.g. 18.41 g a.i./ha for topramezone as present in the product Impact™ and e.g. 138 g a.i./ha for tembotrione as present in the product Laudis SC™.

In the field trials in the present examples, mesotrione present in the product Callisto™ was applied in a field dose of 1× corresponding to 105 g a.i./ha, and topramezone as present in the product Impact™ was applied in a field dose of 1× corresponding to 18.41 g a.i./ha.

Further exemplary 1× field doses for selected HPPD inhibitors are
Isoxaflutole (Balance Flexx™): 105 g a.i./ha
Pyrasulfutole: 37.5 g a.i./ha
Tembotrione (2-{2-chloro-4-mesyl-3-[(2,2,2-trifluoroethoxy)methyl]benzoyl}cyclohexane-1,3-dione or 2-[2-chloro-4-(methylsulfonyl)-3-[(2,2,2-trifluoroethoxy)methyl]benzoyl]-1,3-cyclohexanedione; formulation Laudis SC™): 138 g a.i./ha.

Another exemplary 1× field dose of tembotrione: 100 g a.i./ha. Accordingly, a field dose of 1.5× refers to an applied dose of 150% of the 1× dose, a field dose of 2× refers to an applied dose of 200% of the 1× dose of a specific HPPD inhibitor or HPPD inhibitor formulation and so on.

In another example, the plant cell, plant part, plant or seed disclosed herein has tolerance to a field dose of at least 2× of at least one HPPD inhibitor.

In yet a further example, the plant cell, plant part, plant or seed disclosed herein has tolerance to a field dose of at least 3× or at least 4× of at least one HPPD inhibitor.

In a particular embodiment, the plant cell, plant part, plant or seed disclosed herein has tolerance to a field dose of at least 1×IFT, of at least 2×IFT or of at least 4×IFT. In an even further embodiment, said dose of at least 1×IFT, of at least 2×IFT, or of at least 4×IFT is applied pre-emergence.

Tolerance to a particular dose of an HPPD inhibitor such as an HPPD inhibitor herbicide, as used herein, refers to a plant displaying a minimal amount of damage after treatment with said herbicide dose. Accordingly, a herbicide tolerant plant according to the invention, in the field, shows a visual damage of the aerial parts of the plant of not more than 40%, not more than 35%, not more than 30%, not more than 27%, not more than 25%, not more than 20%, not more than 15%, not more than 10%, not more than 9%, not more than 8%, not more than 7%, not more than 6% or not more than 5% seven days after treatment with at least one HPPD inhibitor. Damage may be assessed by the extent of bleaching, chlorosis and/or necrosis of the aerial parts of the plant, including leaves and stem. Accordingly, tolerance may manifest in chlorosis, bleaching and/or necrosis of not more than 40%, not more than 35%, not more than 30%, not more than 27%, not more than 25%, not more than 20%, not more than 15%, not more than 10%, not more than 9%, not more than 8%, not more than 7%, not more than 6% or not more than 5% seven days after treatment with at least one HPPD inhibitor. Damage or plant response scoring is described elsewhere in the application.

Alternatively, a herbicide tolerant plant according to the invention, in the field, shows a visual damage of the aerial parts of the plant of not more than 20%, not more than 15%, not more than 10%, not more than 9%, not more than 8%, not more than 7%, not more than 6% or not more than 5% 21 days after treatment with at least one HPPD inhibitor. In other words and in accordance with the above, tolerance may manifest in chlorosis, bleaching and/or necrosis of not more than 20%, not more than 15%, not more than 10%, not more than 9%, not more than 8%, not more than 7%, not more than 6% or not more than 5% 21 days after treatment with at least one HPPD inhibitor.

In a different alternative, a herbicide tolerant plant according to the invention, in the field, shows a visual damage of the aerial parts of the plant of not more than 10%, not more than 6%, not more than 5%, not more than 4% or not more than 3% 21 days after treatment with at least one HPPD inhibitor. In other words and in accordance with the above, tolerance may manifest in chlorosis, bleaching and/or necrosis of not more than 10%, not more than 6%, not more than 5%, not more than 4% or not more than 3% 21 days after treatment with at least one HPPD inhibitor.

Said at least one HPPD inhibitor can also be more than one HPPD inhibitor such as at least two, at least three, at least, four, at least five, at least six, at least 10 or even more HPPD inhibitors. Thereby, any combination of HPPD inhibitors for each of the above options is possible. For example, plants of the invention may be tolerant to at least two HPPD inhibitors or the chimeric gene of the invention may confer tolerance to at least two HPPD inhibitors, wherein said at least two inhibitors may comprise isoxaflutole and topramezone, isoxaflutole and mesotrione, isoxaflutole and pyrasulfutole, isoxaflutole and tembotrione, topramezone and mesotrione, topramezone and pyrasulfutole, topramezone and tembotrione, mesotrione and pyrasulfutole, mesotrione and tembotrione or pyrasulfultole and tembotrione. Or said at least one HPPD inhibitor may be at least three HPPD inhibitors, wherein said at least three inhibitors may comprise isoxaflutole, topramezone and mesotrione; isoxaflutole, topramezone and pyrasulfutole; isoxaflutole, topramezone and tembotrione; isoxaflutole, mesotrione and pyrasulfutole; isoxaflutole, mesotrione and tembotrione; isoxaflutole, mesotrione and pyrasulfutole; isoxaflutole, isoxaflutole and tembotrione; topramezone, mesotrione and pyrasulfutol; topramezone, mesotrione and tembotrione; topramezone, pyrasulfutole and tembotrione or mesotrione, pyrasulfutole and tembotrione. Combinations of at least four HPPD inhibitors may comprise isoxaflutole, topramezone, mesotrione and pyrasulfutole; isoxaflutole, topramezone, mesotrione and tembotrione; isoxaflutole, mesotrione, pyrasulfutole and tembotrione or topramezone, mesotrione, pyrasulfutole and tembotrione. An exemplary combination of at least five HPPD inhibitors comprises comprise isoxaflutole, topramezone, mesotrione, pyrasulfutole and tembotrione.

Tolerance levels to different HPPD inhibitors may also differ. For example, whereas the chimeric gene of the invention confers tolerance to cotton plants to 2× for one HPPD inhibitor, it may be 1× for another one. In any case, tolerance is provided to at least 1× of each HPPD inhibitor as claimed.

Other herbicide-tolerance genes include a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992, Curr. Topics Plant Physiol. 7, 139-145), the genes encoding a *Petunia* EPSPS (Shah et al., 1986, Science 233, 478-481), a Tomato EPSPS (Gasser et al., 1988, J. Biol. Chem. 263, 4280-4289), or an Eleusine EPSPS (WO 01/66704). It can also be a mutated EPSPS as described in for example EP 0837944, WO 00/66746, WO 00/66747 or WO02/26995. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 02/36782, WO 03/092360, WO 05/012515 and WO 07/024782. Glyphosate-tolerant plants can also be obtained by selecting plants containing naturally-occurring mutations of the above-mentioned genes, as described in for example WO 01/024615 or WO 03/013226. EPSPS genes that confer glyphosate tolerance are described in e.g. U.S. patent application Ser. Nos. 11/517,991, 10/739,610, 12/139,408, 12/352,532, 11/312,866, 11/315,678, 12/421,292, 11/400, 598, 11/651,752, 11/681,285, 11/605,824, 12/468,205, 11/760,570, 11/762,526, 11/769,327, 11/769,255, 11/943801 or 12/362,774. Other genes that confer glyphosate tolerance, such as decarboxylase genes, are described in e.g. U.S. patent application Ser. Nos. 11/588,811, 11/185, 342, 12/364,724, 11/185,560 or 12/423,926.

Among the DNA sequences encoding a suitable EPSPS which confer tolerance to the herbicides which have EPSPS as a target, mention will more particularly be made of the gene which encodes a plant EPSPS, in particular maize EPSPS, particularly a maize EPSPS which comprises two mutations, particularly a mutation at amino acid position 102 and a mutation at amino acid position 106 (WO 2004/074443), and which is described in Patent Application U.S. Pat. No. 6,566,587, hereinafter named double mutant maize EPSPS or 2mEPSPS (see also SEQ ID NO: 20 from nt 4602-5939 for a nucleic acid sequence encoding this EPSPS and SEQ ID NO: 22 for the amino acid sequence of the resulting enzyme).

In the case of the DNA sequences encoding EPSPS, and more particularly encoding the above genes, the sequence encoding these enzymes is advantageously preceded by a sequence encoding a transit peptide targeting the EPSPS protein to the chloroplast. A particular chloroplast transit peptide of interest to express EPSPS proteins is the "optimized transit peptide" as described in U.S. Pat. No. 5,510, 471 or 5,633,448.

Even other herbicide tolerance genes may encode an enzyme detoxifying the herbicide or a mutant glutamine synthase enzyme that is resistant to inhibition, e.g. described in U.S. patent application Ser. No. 11/760,602. One such efficient detoxifying enzyme is an enzyme encoding a phosphinothricin acetyltransferase (such as the bar or pat protein from *Streptomyces* species). Phosphinothricin acetyltransferases are for example described in U.S. Pat. Nos. 5,561, 236; 5,648,477; 5,646,024; 5,273,894; 5,637,489; 5,276, 268; 5,739,082; 5,908,810 and 7,112,665.

Still further herbicide tolerance genes encode variant ALS enzymes (also known as acetohydroxyacid synthase, AHAS) as described for example in Tranel and Wright (2002, Weed Science 50:700-712), but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270. Other imidazolinone-tolerance genes are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerance genes are described in for example WO 07/024782 and U.S. Patent Application No. 61/288,958.

Insect resistance gene may comprise a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP 1999141 and WO 2007/107302), or such proteins encoded by synthetic genes as e.g. described in and U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774) or the binary toxin made up of the Cry1A or Cry1F proteins and the Cry2Aa or Cry2Ab or Cry2Ae proteins (U.S. patent application Ser. No. 12/214, 022 and EP 08010791.5); or 3) a hybrid insecticidal protein comprising parts of different insecticidal crystal proteins from *Bacillus thuringiensis*, such as a hybrid of the proteins in 1) above or a hybrid of the proteins of 2) above, e.g., the Cry1A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. No. 61/126,083 and 61/195,019), or the binary toxin made up of the VIP3 protein and the Cry2Aa or Cry2Ab or Cry2Ae proteins (U.S. patent application Ser. No. 12/214, 022 and EP 08010791.5);

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein).

An "insect-resistant gene as used herein, further includes transgenes comprising a sequence producing upon expression a double-stranded RNA which upon ingestion by a plant insect pest inhibits the growth of this insect pest, as described e.g. in WO 2007/080126, WO 2006/129204, WO 2007/074405, WO 2007/080127 and WO 2007/035650.

Abiotic stress tolerance genes include 1) a transgene capable of reducing the expression and/or the activity of poly(ADP-ribose) polymerase (PARP) gene in the plant cells or plants as described in WO 00/04173, WO/2006/045633, EP 04077984.5, or EP 06009836.5.

2) a transgene capable of reducing the expression and/or the activity of the PARG encoding genes of the plants or plants cells, as described e.g. in WO 2004/090140.

3) a transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase as described e.g. in EP 04077624.7, WO 2006/133827, PCT/EP07/002433, EP 1999263, or WO 2007/107326.

Enzymes involved in carbohydrate biosynthesis include those described in e.g. EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. No. 5,824,790, U.S. Pat. No. 6,013,861, WO 94/04693, WO 94/09144, WO 94/11520, WO 95/35026 or WO 97/20936 or enzymes involved in the production of polyfructose, especially of the inulin and levan-type, as disclosed in EP 0663956, WO 96/01904, WO 96/21023, WO 98/39460, and WO 99/24593, the production of alpha-1,4-glucans as disclosed in WO 95/31553, US 2002031826, U.S. Pat. No. 6,284,479, U.S. Pat. No. 5,712,107, WO 97/47806, WO 97/47807, WO 97/47808 and WO 00/14249, the production of alpha-1,6 branched alpha-1,4-glucans, as disclosed in WO 00/73422, the production of alternan, as disclosed in e.g. WO 00/47727, WO 00/73422, EP 06077301.7, U.S. Pat. No. 5,908,975 and EP 0728213, the production of hyaluronan, as for example disclosed in WO 2006/032538, WO 2007/039314, WO 2007/039315, WO 2007/039316, JP 2006304779, and WO 2005/012529.

Cotton plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:
a) Plants, such as cotton plants, containing an altered form of cellulose synthase genes as described in WO 98/00549
b) Plants, such as cotton plants, containing an altered form of rsw2 or rsw3 homologous nucleic acids as described in WO 2004/053219
c) Plants, such as cotton plants, with increased expression of sucrose phosphate synthase as described in WO 01/17333
d) Plants, such as cotton plants, with increased expression of sucrose synthase as described in WO 02/45485
e) Plants, such as cotton plants, wherein the timing of the plasmodesmatal gating at the basis of the fiber cell is altered, e.g. through downregulation of fiber-selective β-1,3-glucanase as described in WO 2005/017157, or as described in EP 08075514.3 or U.S. Patent Appl. No. 61/128,938
f) Plants, such as cotton plants, having fibers with altered reactivity, e.g. through the expression of N-acetylglucosaminetransferase gene including nodC and chitin synthase genes as described in WO 2006/136351.

It is also an embodiment of the invention to provide chimeric genes encoding re-designed meganucleases as herein described, wherein the chimeric gene comprise a plant expressible promoter operably linked to a DNA region encoding a protein comprising an amino acid sequence corresponding to the amino acid sequence of I-CreI as a scaffold (SEQ ID NO 16) comprising an S at position 32; Y at position 33; Q at position 38; Q at position 80; S at position 40; T at position 42; R at position 77; Y at position 68; Q at position 70; H at position 75; T at position 44; I at position 24; Q at position 26; K at position 28 and an N at position 30, and/or wherein the chimeric gene comprise a plant expressible promoter operably linked to a DNA region encoding a second protein protein comprising an amino acid sequence corresponding to the amino acid sequence of I-CreI as a scaffold (SEQ ID NO 16) comprising an S at position 70; Q at position 44; K at position 24; A at position 26; K at position 28; N at position 30; S at position 32; Y at position 33; Q at position 38; Q at position 80; S at position 40; T at position 42; Q at position 77 and a Y at position 68, such as a protein comprising the amino acid sequence of SEQ ID 5 or SEQ ID 6 (corresponding amino acid positions in redesigned meganucleases with respect to I-CreI can be determined by alignment).

The person skilled in the art will appreciate that, in addition to the nuclear genome, the methods of the invention may also be applied to modify e.g. the chloroplast genome or mitochondrial genome, whereby DSB induction at the predefined site and can further be enhanced by providing the correct targeting signal to the endonuclease enzyme.

It will be appreciated that the methods of the invention can be applied to any plant (Angiospermae or Gymnospermae) including but not limited to cotton, canola, oilseed rape, soybean, vegetables, potatoes, *Lemna* spp., *Nicotiana* spp., *Arabidopsis*, alfalfa, barley, bean, corn, cotton, flax, millet, pea, rape, rice, rye, safflower, sorghum, soybean, sunflower, tobacco, turfgrass, wheat, asparagus, beet and sugar beet, broccoli, cabbage, carrot, cauliflower, celery, cucumber, eggplant, lettuce, onion, oilseed rape, pepper, potato, pumpkin, radish, spinach, squash, sugar cane, tomato, zucchini, almond, apple, apricot, banana, blackberry, blueberry, cacao, cherry, coconut, cranberry, date, grape, grapefruit, guava, kiwi, lemon, lime, mango, melon, nectarine, orange, *papaya*, passion fruit, peach, peanut, pear, pineapple, pistachio, plum, raspberry, strawberry, tangerine, walnut and watermelon.

In a specific embodiment, the plant is cotton. Cotton, as used herein refers to any existing cotton variety. For example, the cotton plant cell can be from a variety useful for growing cotton. The most commonly used cotton varieties are *Gossypium barbadense, G. hirsutum, G. arboreum* and *G. herbaceum*. Further varieties include *G. africanum* and *G. raimondii*. The same applies to the cotton plant, cotton plant part and the cotton seed described herein.

Example cotton plants disclosed herein include those from which embryogenic callus can be derived, such as Coker 312, Coker310, Coker 5Acala SJ-5, GSC25110, FIBERMAX 819, Siokra 1-3, T25, GSA75, Acala SJ2, Acala SJ4, Acala SJ5, Acala SJ-C1, Acala B1644, Acala B1654-26, Acala B1654-43, Acala B3991, Acala GC356, Acala GC510, Acala GAM1, Acala C1, Acala Royale, Acala Maxxa, Acala Prema, Acala B638, Acala B1810, Acala B2724, Acala B4894, Acala B5002, non Acala "picker" Siokra, "stripper" variety FC2017, Coker 315, STONEVILLE 506, STONEVILLE 825, DP50, DP61, DP90, DP77, DES119, McN235, HBX87, HBX191, HBX107, FC 3027, CHEMBRED A1, CHEMBRED A2, CHEMBRED A3, CHEMBRED A4, CHEMBRED B1, CHEMBRED B2, CHEMBRED B3, CHEMBRED C1, CHEMBRED C2, CHEMBRED C3, CHEMBRED C4, PAYMASTER 145, HS26, HS46, SICALA, PIMA S6 ORO BLANCO PIMA, FIBERMAX FM5013, FIBERMAX FM5015, FIBERMAX FM5017, FIBERMAX FM989, FIBERMAX FM832, FIBERMAX FM966, FIBERMAX FM958, FIBERMAX FM989, FIBERMAX FM958, FIBERMAX FM832, FIBERMAX FM991, FIBERMAX FM819, FIBERMAX FM800, FIBERMAX FM960, FIBERMAX FM966, FIBERMAX FM981, FIBERMAX FM5035, FIBERMAX FM5044, FIBERMAX FM5045, FIBERMAX FM5013, FIBERMAX FM5015, FIBERMAX FM5017 or FIBERMAX FM5024 and plants with genotypes derived thereof. These are suitable for introducing the chimeric gene disclosed herein.

It is also an object of the invention to provide plant cells, plant parts and plants generated according to the methods of the invention, such as fruits, seeds, embryos, reproductive tissue, meristematic regions, callus tissue, leaves, roots, shoots, flowers, fibers, vascular tissue, gametophytes, sporophytes, pollen and microspores, which are characterised in that they comprise a specific modification in the genome (insertion, replacement and/or deletion) or in that they comprise the chimeric HDDP gene according to the invention. Gametes, seeds, embryos, either zygotic or somatic, progeny or hybrids of plants comprising the DNA modification events, which are produced by traditional breeding methods, are also included within the scope of the present invention. Such plants may contain a DNA of interest inserted at or instead of a target sequence or may have a specific DNA sequence deleted (even single nucleotides), and will only be different from their progenitor plants by the presence of this heterologous DNA or DNA sequence or the absence of the specifically deleted sequence post exchange. Alternatively, such plants contain the chimeric HPPD gene according to the invention. It will be clear that the plant cells, plant parts and plants of the invention can be from any plant as listed herein above, including all cotton plants.

In particular embodiments the plant cell described herein is a non-propagating plant cell or a plant cell that cannot be regenerated into a plant or a plant cell that cannot maintain its life by synthesizing carbohydrate and protein from the inorganics, such as water, carbon dioxide, and inorganic salt, through photosynthesis.

Seed is formed by an embryonic plant enclosed together with stored nutrients by a seed coat. It is the product of the ripened ovule of gymnosperm and angiosperm plants, which occurs after fertilization and to a certain extent growth within the mother plant. The seed disclosed herein retain the distinguishing characteristics of the parents, such as seed obtained by selfing or crossing, e.g. hybrid seed (obtained by crossing two inbred parental lines).

The plant cells and plants described herein such as those obtained by the methods described herein may be further used in breeding procedures well known in the art, such as crossing, selfing, and backcrossing. Breeding programs may involve crossing to generate an F1 (first filial) generation, followed by several generations of selfing (generating F2, F3, etc.). The breeding program may also involve backcrossing (BC) steps, whereby the offspring is backcrossed to one of the parental lines, termed the recurrent parent.

"Introgressing" means the integration of a gene in a plant's genome by natural means, i.e. by crossing a plant comprising the chimeric gene described herein with a plant not comprising said chimeric gene. The offspring can be selected for those comprising the chimeric gene.

Accordingly, also disclosed herein is a method for producing plants comprising the introduced trait (i.e. the genomic modification or HPPD gene according to the invention) comprising the step of crossing the plant disclosed herein with another plant or with itself and selecting for offspring comprising the introduced trait.

The plant cells and plants described herein and/or obtained by the methods disclosed herein may also be further used in subsequent transformation procedures, e.g. to introduce a further chimeric gene.

The plants and seeds according to the invention may be further treated with a chemical compound, such as a chemical compound selected from the following lists:

Fruits/Vegetables:
Herbicides: Atrazine, Bromacil, Butafenacil, Diuron, Fluazifop, Glufosinate, Glyphosate, Halosulfuron, Halosulfuron-methyl, Indaziflam, Linuron, Metribuzin, Paraquat, Propyz amide, Sethoxydim, Simazine, Trifluralin.
Insecticides: Abamectin, Acequinocyl, Acetamiprid, Aldicarb, Azadirachtin, Benfuracarb, Bifenazate, Buprofezin, Carbaryl, Carbofuran, Chlorantraniliprole (Rynaxypyr), Chlorpyrifos, Chromafenozide, Clothianidin, Cyanopyrafen, Cyantraniliprole (Cyazypyr), Cyflumetofen, beta-Cyfluthrin, gamma-Cyhalothrin, lambda-Cyhalothrin, alpha-Cypermethrin, Deltamethrin, Diafenthiuron, Dinotefuran, Emamectin-benzoate, Esfenvalerate, Fenamiphos, Fenbutatin-oxid, Flonicamid, Fluacrypyrim, Flubendiamide, Fluensulfone, Fluopyram, Flupyradifurone, Imicyafos, Imidacloprid, Indoxacarb, Metaflumizone, Methiocarb, Methoxyfenozide, Novaluron, Pymetrozine, Pyrifluquinazon, Pyriproxifen, Spinetoram, Spinosad, Spirodiclofen, Spiromesifen, Spirotetramat, Sulfoxaflor, Thiacloprid, Thiamethoxam, Thiodicarb, Triflumuron, 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide, 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide, 1-{2-fluoro-4-methyl-5-[(2,2,2-trifluorethyl)sulfinyl]phenyl}-3-(trifluoromethyl)-1H-1,2,4-triazol-5-amine, (1E)-N-[(6-chloropyridin-3-yl)methyl]-N'-cyano-N-(2,2-difluoroethyl)ethanimidamide, Bacillus firmus, Bacillus firmus strain I-1582, Bacillus thuriengiensis, Bacillus subtilis, Bacillus subtilis strain GB03, Bacillus subtilis strain QST 713, Metarhizium anisopliae, Metarhizium anisopliae strain F52.
Fruits/Vegetables Fungicides: Ametoctradin, Amisulbrom, Azoxystrobin, Benthiavalicarb, N-[9-(dichloromethylene)-1,2,3,4-tetrahydro-1,4-methanonaphthalen-5-yl]-3-(difluoromethyl)-1-methyl-1H-pyrazole-4-carboxamide (Benzovindiflupyr, Benzodiflupyr), Bixafen, Boscalid, Captan, Carbendazim, Chlorothalonil, Copper, Cyazofamid, Cyflufenamid, Cymoxanil, Cyproconazole, Cyprodinil, Difenoconazole, Dimetomorph, Dithianon, Epoxiconazole, Famoxadone, Fenamidone, Fenhexamid, Fenpyraz amine, Fluazinam, Fludioxonil, Fluopicolide, Fluopyram, Fluoxastrobin, Fluquinconazole, Fluthianil, Fluxapyroxad, Folpet, Fosetyl, Iprodione, Iprovalicarb, Isopyrazam, Isotianil, Kresoxim-methyl, Mancozeb, Mandipropamid, Meptyldinocap, Metalaxyl/Mefenoxam, Metiram, Metrafenone, Myclobutanil, Penconazole, Penflufen, Penthiopyrad, Phosphonic acid (H3PO3), Picoxystrobin, Propamocarb, Propiconazole, Propineb, Proquinazid, Prothioconazole, Pyraclostrobin, Pyrimethanil, Pyriofenone, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, Quinoxyfen, Sedaxane, Spiroxamine, Sulphur, Tebuconazole, Thiophanate-methyl, Thiram, Triadimenol, Trifloxystrobin.
Cereals:
Herbicides: 2,4-D, Amidosulfuron, Beflubutamid, Bentazon, Bifenox, Bromoxynil, Carfentrazone-ethyl, Chlorotoluron, Chlorsulfuron, Cinidon-ethyl, Clodinafop-propargyl, Clopyralid, Dicamba, Dichlorprop, Dichlorprop-P, Diclofop-methyl, Diflufenican, Fenoxaprop, Florasulam, Flucarbazone-sodium, Flufenacet, Flupyrsulfuron-methyl-sodium, Fluroxypyr, Flurtamone, Glyphosate, Imazamox, Imazamethabenz, Iodosulfuron, Ioxynil, Isoproturon, Isoxaben, MCPA, MCPB, Mecoprop-P, Mesosulfuron, Metsulfuron, Pendimethalin, Picolinafen, Pinoxaden, Prop oxycarbazone, Prosulfocarb, Pyraflufen, Pyrasulfotole, Pyroxsulam, Sulfosulfuron, Thiencarbaz one, Thifensulfuron, Traloxydim, Triallat, Triasulfuron, Tribenuron, Trifluralin, Tritosulfuron (Safener: Mefenpyr, Mefenpyr-diethyl, Cloquintocet).
Fungicides: Azoxystrobin, N-[9-(dichloromethylene)-1,2,3,4-tetrahydro-1,4-methanonaphthalen-5-yl]-3-(difluoromethyl)-1-methyl-1H-pyrazole-4-carboxamide (Benzovindiflupyr, Benzodiflupyr), Bixafen, Boscalid, Carbendazim, Carboxin, Chlorothalonil, Cyflufenamid, Cyproconazole, Cyprodinil, Difenoconazole, Dimoxystrobin, Diniconazole, Epoxiconazole, Fenpropidin, Fenpropimorph, Fludioxonil, Fluopyram, Fluoxastrobin, Fluquinconazole, Flusilazole, Fluthianil, Flutriafol, Fluxapyroxad, Imazalil, Ipconazole, Isopyrazam, Kresoxim-methyl, Mefenoxam, Metalaxyl, Metconazole, Metominostrobin, Metrafenone, Myclobutanil, Penflufen, Penthiopyrad, Picoxystrobin, Prochloraz, Propiconazole, Proquinazid, Prothioconazole, Pyraclostrobin, Pyriofenone, Quinoxyfen, Sedaxane, Silthiofam, Spiroxamine, Tebuconazole, Thiabendazole, Thiophanate-methyl, Triadimenol, Trifloxystrobin, Triticonazole, *Bacillus firmus, Bacillus firmus* strain I-1582, *Bacillus subtilis, Bacillus subtilis* strain GB03, *Bacillus subtilis* strain QST 713.

Insecticides: Acetamiprid, Azadirachtin, Benfuracarb, Bifenthrin, Chlorantraniliprole (Rynaxypyr), Chlorpyriphos, Clothianidin, Cyantraniliprole (Cyazypyr), beta-Cyfluthrin, alpha-Cypermethrin, Deltamethrin, Diafenthiuron, Dimethoate, Dinetofuran, Fipronil, Fluensulfone, Fluopyram, Flupyradifurone, Imicyafos, Imidacloprid, Metaflumizone, Metamidophos, Methiocarb, Phorate, Pirimicarb, Pymetrozine, Pyrifluquinaz on, Spirotetramate, Sulfoxaflor, Tefluthrin, Thiacloprid, Thiamethoxam, Thiodicarb, Transfluthim, Triflumuron, 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide, 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide, 1-{2-fluoro-4-methyl-5-[(2,2,2-trifluoroethyl)sulfinyl]phenyl}-3-(trifluoromethyl)-1H-1,2,4-triazol-5-amine, (1E)-N-[(6-chloropyridin-3-yl)methyl]-N'-cyano-N-(2,2-difluoroethyl)ethanimidamide, *Bacillus firmus, Bacillus firmus* strain I-1582, *Bacillus subtilis, Bacillus subtilis* strain GB03, *Bacillus subtilis* strain QST 713, *Metarhizium anisopliae* F52.

Maize:
Herbicides/Plant Growth Regulators (PGRs): Aclonifen, Atrazine, Alachlor, Bentazon, Bicyclopyrone, Bromoxynil, Acetochlor, Aclonifen, Dicamba, Clopyralid, Dimethenamid-P, Florasulam, Flufenacet, Fluroxypyr, Foramsulfuron, Glufosinate, Glyphosate, Isoxadifen, Isoxaflutole, (S-)Metolachlor, Mesotrione, Nicosulfuron, Pendimethalin, Pethoxamid, Primisulfuron, Pyroxasulfon, Rimsulfuron, Sulcotrione, Tembotrione, Terbuthylazin, Thiencarbaz one, Thifensulfuron-methyl, Topramezone, Saflufenacil (Safener: Isoxadifen-ethyl).

Insecticides: Abamectin, Acetamiprid, Azadirachtin, Benfuracarb, Bifenthrin, Carbofuran, Chlorantraniliprole (Rynaxypyr), Chlorpyrifos, Clothianidin, Cyantraniliprole (Cyazypyr), (beta-) Cyfluthrin, lambda-Cyhalothrin, (alpha-)Cypermethrin, Deltamethrin, Dinotefuran, Ethiprole, Fipronil, Flubendiamide, Fluensulfone, Fluopyram, Flupyradifurone, Indoxacarb, Imicyafos, Imidacloprid, Lufenuron, Metaflumiz one, Methiocarb, Pymetrozine, Pyrifluquinazon, Spinetoram, Spinosad, Spiromesifen, Spirotetramate, Sulfoxaflor, Tefluthrin, Terbufos, Thiamethoxam, Thiodicarb, Triflumuron, Tebupirimphos, Thiacloprid, 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide, 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide, 1-{2-fluoro-4-methyl-5-[(2,2,2-trifluorethyl)sulfinyl]phenyl}-3-(trifluoromethyl)-1H-1,2,4-triazol-5-amine, (1E)-N-[(6-chloropyridin-3-yl)methyl]-N'-cyano-N-(2,2-difluoroethyl)ethanimidamide, *Bacillus firmus, Bacillus firmus* strain I-1582, *Bacillus subtilis, Bacillus subtilis* strain GB03, *Bacillus subtilis* strain QST 713, *Metarhizium anisopliae* F52.

Fungicides: Azoxystrobin, N-[9-(dichloromethylene)-1,2,3,4-tetrahydro-1,4-methanonaphthalen-5-yl]-3-(difluoromethyl)-1-methyl-1H-pyrazole-4-carboxamide (Benzovindiflupyr, Benzodiflupyr), Bixafen, Boscalid, Carbendazim, *Chenopodium quinjoa*, Cyproconazole, Dimoxystrobin, Epoxiconazole, Fenamidone, Fipronil, Fluopyram, Fluthianil, Fluoxastrobin, Flusilazole, Flutriafol, Fluxapyroxad, Ipconazole, Isopyrazam, Mancozeb, Mefenoxam, Metalaxyl, Metominostrobin, Metconazole, Myclobutanil, Penflufen, Penthiopyrad, Picoxystrobin, Propiconazole, Prothioconazole, Pyraclostrobin, Saponin, Sedaxane, Tebuconazole, Thiram, Triadimenol, Trifloxystrobin, Ziram, *Bacillus firmus, Bacillus firmus* strain I-1582, *Bacillus subtilis, Bacillus subtilis* strain GB03, *Bacillus subtilis* strain QST 713, *Bacillus pumulis, Bacillus. pumulis* strain GB34.

Rice:
Herbicides: Anilofos, Azimsulfuron, Benfuresate, Bensulfuron, Bentazone, Benzobicyclon, Benzofenap, Bispyribac, Bromobutide, Butachlor, Cafenstrole, Carfentrazone-ethyl, Clomazone, Clomeprop Cumyluron, Cyhalofop, Daimuron, Dimepiperate, Esprocarb, Ethoxysulfuron, Fenoxaprop, Fenoxasulfone, Fentrazamide, Flucetosulfuron, Flufenacet, Halosulfuron, Imazosulfuron, Indanofan, Ipfencarbazone, Mefenacet, Mesotrione, Metamifop, Metazosulfuron, Molinate, Naproanilide, Orthosulfamuron, Oxadiargyl, Oxadiazone, Oxaziclomefone, Penoxsulam, Pentoxazone, Pretilachlor, Profoxydim, Propanil, Propyrisulfuron, Pyraclonil, Pyrazolate, Pyrazosulfuron, Pyrazoxyfen, Pyributicarb, Pyriftalid, Pyriminobac-methyl, Pyrimisulfan, Quinclorac, Tefuryltrione, Thenylchlor, Thiobencarb, Triafamone.

Insecticides: Acetamiprid, Azadirachtin, Benfuracarb, Buprofezin, Carbofuran, Chlorantraniliprole (Rynaxypyr), Chlorpyriphos, Chromafenozide, Clothianidin, Cyantraniliprole (Cyazypyr), Cypermethrin, Deltamethrin, Diazinon, Dinotefuran, Emamectin-benzoate, Ethiprole, Etofenprox, Fenobucarb, Fipronil, Flubendiamide, Fluensulfone, Fluopyram, Flupyradifurone, Imicyafos, Imidacloprid, Isoprocarb, Metaflumizone, Pymetrozine, Pyrifluquinazon, Spinetoram, Spinosad, Spirotetramate Sulfoxaflor, Thiacloprid, Thiamethoxam, 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide, 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide, 1-{2-fluoro-4-methyl-5-[(2,2,2-trifluorethyl)sulfinyl]phenyl}-3-(trifluoromethyl)-1H-1,2,4-triazol-5-amine, (1E)-N-[(6-chloropyridin-3-yl)methyl]-N'-cyano-N-(2,2-difluoroethyl)ethanimidamide, *Bacillus firmus, Bacillus firmus* strain I-1582, *Bacillus subtilis, Bacillus subtilis* strain GB03, *Bacillus subtilis* strain QST 713, *Metarhizium anisopliae* F52.

Fungicides: Azoxystrobin, N-[9-(dichloromethylene)-1,2,3,4-tetrahydro-1,4-methanonaphthalen-5-yl]-3-(difluoromethyl)-1-methyl-1H-pyrazole-4-carboxamide (Benzovindiflupyr, Benzodiflupyr), Bixafen, Carbendazim, Carpropamid, Chlorothalonil, Copper-oxychloride, Cyproconazole, Diclocymet, Difenoconazole, Edifenphos, Epoxiconazole, Ferimzone, Fludioxonil, Fluopyram, Fluoxastrobin, Flusilazole, Fluthianil, Flutolanil, Fluxapyroxad, Furametpyr, Gentamycin, Hexaconazole, Hymexazol, Ipconazole, Iprobenfos (IBP), Iprodione, Isoprothiolane, Isotianil, Kasugamycin, Mancozeb, Mefenoxam, Metalaxyl, Metominostrobin, Myclobutanil, Orysastrobin, Pencycuron, Penflufen, Phthalide, Probenazole, Prochloraz, Propamocarb, Propiconazole, Propineb, Prothioconazole, Pyroquilon, Sedaxane, Simconazole, Streptomycin, Sulphur, Tebuconazole, Thifluzamide, Thiophanate-methyl, Thiram, Tiadinil, Tricyclazole, Trifloxystrobin, Validamycin, *Bacillus firmus, Bacillus firmus* strain I-1582, *Bacillus subtilis, Bacillus subtilis* strain GB03, *Bacillus subtilis* strain QST 713.

Cotton:
Herbicides: Carfentrazone, Clethodim, Diuron, Fluazifop-butyl, Flumioxazin, Fluometuron, Glufosinate, Glyphosate, MSMA, Norflurazon, Oxyfluorfen, Pendimethalin, Prometryn, Pyrithiobac-sodium, Tepraloxydim, Thidiazuron, Trifloxysulfuron, Trifluralin.

Insecticides: Abamectin, Acephate, Acetamiprid, Aldicarb, Azadirachtin, Bifenthrin, Chlorantraniliprole (Rynaxypyr), Chlorpyrifos, Clothianidin, Cyantraniliprole (Cyazypyr), (beta-)Cyfluthrin, gamma-Cyhalothrin, lambda-Cyhalothrin, Cypermethrin, Deltamethrin, Diafenthiuron, Dinotefuran, Emamectin-benzoate, Flonicamid, Flubendiamide, Fluensulfone, Fluopyram, Flupyradifurone, Imicyafos, Imidacloprid, Indoxacarb, Metaflumizone, Pymetrozine, Pyridalyl, Pyrifluquinazon, Spinetoram, Spinosad, Spiromesifen, Spirotetramat, Sulfoxaflor, Thiacloprid, Thiamethoxam, Thiodicarb, Triflumuron, 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide, 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide, 1-{2-fluoro-4-methyl-5-[(2,2,2-trifluorethyl)sulfinyl]phenyl}-3-(trifluoromethyl)-1H-1,2,4-triazol-5-amine, (1E)-N-[(6-chloropyridin-3-yl)methyl]-N'-cyano-N-(2,2-difluoroethyl)ethanimidamide, *Bacillus firmus, Bacillus firmus* strain I-1582, *Bacillus subtilis, Bacillus subtilis* strain GB03, *Bacillus subtilis* strain QST 713, Metarhizium anisopliae F52.

Fungicides: Azoxystrobin, N-[9-(dichloromethylene)-1,2,3,4-tetrahydro-1,4-methanonaphthalen-5-yl]-3-(difluoromethyl)-1-methyl-1H-pyrazole-4-carboxamide (Benzovindiflupyr, Benzodiflupyr), Bixafen, Boscalid, Carbendazim, Chlorothalonil, Copper, Cyproconazole, Difenoconazole, Dimoxystrobin, Epoxiconazole, Fenamidone, Fluazinam, Fluopyram, Fluoxastrobin, Fluxapyroxad, Ipconazole, Iprodione, Isopyrazam, Isotianil, Mancozeb, Maneb, Mefenoxam, Metalaxyl, Metominostrobin, Pencycuron, Penflufen, Penthiopyrad, Picoxystrobin, Propineb, Prothioconazole, Pyraclostrobin, Quintozene, Sedaxane, Tebuconazole, Tetraconazole, Thiophanate-methyl, Triadimenol, Trifloxystrobin, *Bacillus firmus, Bacillus firmus* strain I-1582, *Bacillus subtilis, Bacillus subtilis* strain GB03, *Bacillus subtilis* strain QST 713.

Soybean:
Herbicides: Alachlor, Bentaz one, Chlorimuron-Ethyl, Cloransulam-Methyl, Fenoxaprop, Fluazifop, Fomesafen, Glufosinate, Glyphosate, Imazamox, Imazaquin, Imazethapyr, (S-)Metolachlor, Metribuzin, Pendimethalin, Tepraloxydim, Trifluralin.

Insecticides: Acetamiprid, Azadirachtin, Chlorantraniliprole (Rynaxypyr), Clothianidin, Cyantraniliprole (Cyazypyr), (beta-) Cyfluthrin, gamma-Cyhalothrin, lambda-Cyhalothrin, Deltamethrin, Dinotefuran, Emamectin-benzoate, Ethiprole, Fipronil, Flonicamid, Flubendiamide, Fluensulfone, Fluopyram, Flupyradifurone, Imicyafos, Imidacloprid, Metaflumizone, Methomyl, Pyrifluquinaz on, Pymetrozine, Spinetoram, Spinosad, Spirodiclofen, Spiromesifen, Spirotetramat, Sulfoxaflor, Thiacloprid, Thiamethoxam, Thiodicarb, Triflumuron, 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide, 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide, 1-{2-fluoro-4-methyl-5-[(2,2,2-trifluorethyl)sulfinyl]phenyl}-3-(trifluoromethyl)-1H-1,2,4-triazol-5-amine, (1E)-N-[(6-chloropyridin-3-yl)methyl]-N'-cyano-N-(2,2-difluoroethyl)ethanimidamide, *Bacillus firmus, Bacillus firmus* strain I-1582, *Bacillus subtilis, Bacillus subtilis* strain GB03, *Bacillus subtilis* strain QST 713, Metarhizium anisopliae F52, *Rhizobia*.

Fungicides: Azoxystrobin, N-[9-(dichloromethylene)-1,2,3,4-tetrahydro-1,4-methanonaphthalen-5-yl]-3-(difluoromethyl)-1-methyl-1H-pyrazole-4-carboxamide (Benzovindiflupyr, Benzodiflupyr), Bixafen, Boscalid, Carbendazim, Carboxin, *Chenopodium quinoa* saponins, Chlorothalonil, Copper, Cyproconazole, Difenoconazole, Dimoxystrobin, Epoxiconazole, Fluazinam, Fludioxonil, Fluopicolide, Fluopyram, Fluoxastrobin, Fluquinconazole, Flutriafol, Fluthianil, Fluxapyroxad, Ipconazole, Isopyrazam, Iprodione, Isotianil, Mancozeb, Maneb, Mefenoxam, Metalaxyl, Metconazole, Metominostrobin, Myclobutanil, Penflufen, Penthiopyrad, Picoxystrobin, Propiconazole, Propineb, Prothioconazole, Pyraclostrobin, Sedaxane, Tebuconazole, Tetraconazole, Thiophanate-methyl, Thiram, Triadimenol, Trifloxystrobin, *Bacillus subtilis, Bacillus subtilis* strain GB03, *Bacillus subtilis* strain QST 713, *Bacillus pumilis, Bacillus pumilis* GB34.

Sugarbeet:
Herbicides: Chloridazon, Clopyralid, Cycloxydim, Desmedipham, Ethofumesate, Fluazifop, Lenacil, Metamitron, Phenmedipham, Quinmerac, Quizalofop, Tepraloxydim, Triallate, Triflusulfuron. Insecticides: Acetamiprid, Aldicarb, Az adirachtin, Clothianidin, Dinetofuran, Deltamethrin, Carbofuran, Chlorantraniliprole (Rynaxypyr), Cyantraniliprole (Cyazypyr), (beta-)Cyfluthrin, gamma-Cyhalothrin, lambda-Cyhalothrin, Cypermethrin, Fipronil, Fluensulfone, Fluopyram, Flupyradifurone, Imicyafos, Imidacloprid, Metaflumizone, Methiocarb, Pymetrozine, Pyrifluquinaz on, Spirotetramate, Sulfoxaflor, Tefluthrin, Thiacloprid, Thiamethoxam, 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide, 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide, 1-{2-fluoro-4-methyl-5-[(2,2,2-trifluorethyl)sulfinyl]phenyl}-3-(trifluoromethyl)-1H-1,2,4-triazol-5-amine, (1E)-N-[(6-chloropyridin-3-yl)methyl]-N'-cyano-N-(2,2-difluoroethyl)ethanimidamide, *Bacillus firmus, Bacillus firmus* strain I-1582, *Bacillus subtilis, Bacillus subtilis* strain GB03, *Bacillus subtilis* strain QST 713, Metarhizium anisopliae F52.

Fungicides: Azoxystrobin, N-[9-(dichloromethylene)-1,2,3,4-tetrahydro-1,4-methanonaphthalen-5-yl]-3-(difluoromethyl)-1-methyl-1H-pyrazole-4-carboxamide (Benzovindiflupyr, Benzodiflupyr), Bixafen, Carbendazim, Chlorothalonil, Copper, Cyproconazole, Difenoconazole, Epoxiconazole, Fefenoxam, Fenpropidin, Fenpropimorph, Fluopyram, Flusilazole, Fluthianil, Flutriafol, Fluxapyroxad, Hymexazol, Ipconazole, Isopyrazam, Kresoximmethyl, Mancozeb, Maneb, Metalaxyl, Myclobutanil, Penflufen, Prochloraz, Propiconazole, Prothioconazole, Tebuconazole, Pyraclostrobin, Quinoxyfen, Sedaxane, Sulphur, Tetraconazole, Thiophanate-methyl, Thiram, Trifloxystrobin, *Bacillus firmus, Bacillus firmus* strain I-1582, *Bacillus subtilis, Bacillus subtilis* strain GB03, *Bacillus subtilis* strain QST 713.

Canola:
Herbicides: Clethodim, Clopyralid, Diclofop, Ethametsulfuron, Fluazifop, Glufosinate, Glyphosate, Metazachlor, Quinmerac, Quizalofop, Tepraloxydim, Trifluralin.
Fungicides/PGRs: Azoxystrobin, N-[9-(dichloromethylene)-1,2,3,4-tetrahydro-1,4-methanonaphthalen-5-yl]-3-(difluoromethyl)-1-methyl-1H-pyrazole-4-carboxamide (Benzovindiflupyr, Benzodiflupyr), Bixafen, Boscalid, Carbendazim, Carboxin, Chlormequat-chloride, Coniothryrium minitans, Cyproconazole, Cyprodinil, Difenoconazole, Dimethomorph, Dimoxystrobin, Epoxiconazole, Famoxadone, Fluazinam, Fludioxonil, Fluopicolide, Fluopyram, Fluoxastrobin, Fluquinconazole, Flusilazole, Fluthianil, Flutriafol, Fluxapyroxad, Iprodione, Isopyrazam, Mefenoxam, Mepiquat-chloride, Metalaxyl, Metconazole, Metominostrobin, Paclobutrazole, Penflufen, Penthiopyrad, Picoxystrobin, Prochloraz, Prothioconazole, Pyraclostrobin, Sedaxane, Tebuconazole, Tetraconazole, Thiophanate-methyl, Thiram, Triadimenol, Trifloxystrobin, *Bacillus firmus, Bacillus firmus* strain I-1582, *Bacillus subtilis, Bacillus subtilis* strain GB03, *Bacillus subtilis* strain QST 713, *Bacillus* pumulis, *Bacillus*. pumulis strain GB34.
Insecticides: Acetamiprid, Aldicarb, Azadirachtin, Carbofuran, Chlorantraniliprole (Rynaxypyr), Clothianidin, Cyantraniliprole (Cyazypyr), (beta-)Cyfluthrin, gamma-Cyhalothrin, lambda-Cyhalothrin, Cypermethrin, Deltamethrin, Dimethoate, Dinetofuran, Ethiprole, Flonicamid, Flubendiamide, Fluensulfone, Fluopyram, Flupyradifurone, tau-Fluvalinate, Imicyafos, Imidacloprid, Metaflumizone, Methiocarb, Pymetrozine, Pyrifluquinazon, Spinetoram, Spinosad, Spirotetramate, Sulfoxaflor, Thiacloprid, Thiamethoxam, 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide, 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide, 1-{2-fluoro-4-methyl-5-[(2,2,2-trifluorethyl)sulfinyl]phenyl}-3-(trifluoromethyl)-1H-1,2,4-triazol-5-amine, (1E)-N-[(6-chloropyridin-3-yl)methyl]-N'-cyano-N-(2,2-difluoroethyl)ethanimidamide, *Bacillus firmus, Bacillus firmus* strain I-1582, *Bacillus subtilis, Bacillus subtilis* strain GB03, *Bacillus subtilis* strain QST 713, Metarhizium anisopliae F52.

Further disclosed herein is a fiber or oil obtained from the cotton plant or seed disclosed herein comprising an HPPD gene according to the invention. Further disclosed herein is yarn, fabric or filler comprising the fiber disclosed herein as well a meal comprising at least a part of the seed of the invention.

In another aspect, the present application discloses a method for obtaining a cotton plant or plant cell tolerant to a field dose of at least 1× of at least one HPPD inhibitor, comprising introducing a chimeric gene comprising (a) a nucleic acid sequence encoding a protein having HPPD activity, wherein said protein has a tryptophan at a position corresponding to position 336 of SEQ ID NO: 19, wherein said protein provides to said plant tolerance to a field dose of at least 1× of at least one HPPD inhibitor, operably linked to (b) a plant expressible promoter and optionally (c) a translational termination and polyadenylation region into a cotton plant cell.

The method may further comprise growing a plant from the plant cell.

Also disclosed herein is a method for controlling weeds in the vicinity of a cotton plant or on a field of cotton plants according to the invention, comprising applying at least one HPPD inhibitor to the vicinity of said cotton plant or to a cotton plant field in a field dose of at least 1×.

In a particular embodiment, the at least one HPPD inhibitor is applied pre-emergence and the same or another at least one HPPD inhibitor is applied post-emergence. For example, the pant or field of plants may be treated with a pre-emergence dose of at least 1× of e.g. IFT followed by a post-emergence dose of at least 1× of the same or another HPPD inhibitor, e.g. MST or TBT.

The term "weed", as used herein, refers to undesired vegetation on e.g. a field, or to plants, other then the intentionally planted plants, which grow unwantedly between the plants of interest and may inhibit growth and development of said plants of interest. The term "controlling weeds" thus includes inhibition of weed growth and killing of weeds.

The vicinity of a plant of interest includes the area around it, in particular the area covered by the roots of a plant through all stages of growth.

At least one HPPD inhibitor is applied to the cotton field or to the vicinity of a cotton plant by spraying a solution comprising said HPPD inhibitor(s) on a cotton field or in the vicinity of a cotton plant such that a concentration of said at least one HPPD inhibitor according to the desired field dose is obtained.

In a particular embodiment, the at least one HPPD inhibitor is applied pre-emergence and the same or another at least one HPPD inhibitor is applied post-emergence. For example, the pant or field of plants may be treated with a pre-emergence dose of at least 1× of IFT and a post-emergence dose of at least 1× of the same or another HPPD inhibitor, such as MST.

In one example, at least one HPPD inhibitor is applied in a dose which is toxic for said weeds. Such a dose is usually 1× but may in individual cases be higher such as 1,5×, 2×, 4× or even more. As already indicated above, dose rates corresponding to 1× may vary depending on many factors. In any case, the dose rate for a given situation may be increased.

As used herein, the amount or concentration of an HPPD inhibitor "toxic for a weed" is interchangeably used with the term "effective amount" or "effective concentration." An "effective amount" and "effective concentration" is an amount or concentration that is sufficient to kill or inhibit the growth of a weed, but that said amount does not kill or inhibit as severely the growth of the cotton plants, plant tissues, plant cells, and seeds disclosed herein. Typically, the effective amount of at least one HPPD inhibitor is an amount that is routinely used in agricultural production systems to kill weeds of interest, expressed as a "field dose". In this regard, for cotton, a field dose of 1× may differ depending on the HPPD inhibitor chosen as has been exemplified above.

In one example, said at least one HPPD inhibitor is applied in a field dose of at least 1.5×.

In a further example said at least one HPPD inhibitor is applied in a field dose of at least 2×.

In yet another example, said at least one HPPD inhibitor is applied in a field dose of at least 3× or at least 4×.

Said at least one HPPD inhibitor may be applied post-emergence but also pre-emergence, or both.

Also disclosed herein is a method of producing a cotton seed or a cotton fiber comprising a chimeric gene comprising (a) a nucleic acid sequence encoding a protein having HPPD activity, wherein said protein has a tryptophan at a position corresponding to position 336 of SEQ ID NO: 19, wherein said protein provides to a cotton plant growing from said seed tolerance to a field dose of at least 1× of at least one HPPD inhibitor, operably linked to (b) a plant expressible promoter; and optionally (c) an translational termination and polyadenylation region, the method comprising providing the plant disclosed herein or the plant obtained by the method described herein above, wherein said plant produces said seed and said chimeric gene is comprised in said seed; and isolating said seed or said fiber from said cotton plant. In one example, said protein having HPPD activity has at least 95% sequence identity to SEQ ID NO: 21, comprises SEQ ID NO: 21 or consists of SEQ ID NO: 19. Other suitable examples for the protein having HPPD function are disclosed elsewhere in this description.

The present application also discloses a method for producing fabric comprising processing the fiber disclosed herein.

Further disclosed is the use of a chimeric gene as disclosed herein, such as a chimeric gene comprising (a) a nucleic acid sequence encoding a protein having HPPD activity, wherein said protein has a tryptophan at a position corresponding to position 336 of SEQ ID NO: 19, wherein said protein provides to a plant tolerance to a field dose of at least 1× of at least one HPPD inhibitor, operably linked to (b) a plant expressible promoter and optionally (c) a translational termination and polyadenylation region for (i) obtaining tolerance to a field dose of at least 1× of at least one HPPD inhibitor in a cotton plant, or (ii) producing a cotton plant tolerant to a field dose of at least 1× of at least one HPPD inhibitor.

Also disclosed herein is the use of the cotton fiber disclosed herein for producing yarn, fabric or filler material.

Further disclosed herein is the use of the seed disclosed herein, such as the cotton seed, for producing seed oil or meal.

A chimeric gene is an artificial gene constructed by operably linking fragments of unrelated genes or other nucleic acid sequences. In other words "chimeric gene" denotes a gene which is not normally found in a plant species or refers to any gene in which the promoter or one or more other regulatory regions of the gene are not associated in nature with a part or all of the transcribed nucleic acid, i.e. are heterologous with respect to the transcribed nucleic acid. More particularly, a chimeric gene is an artificial, i.e. non-naturally occurring, gene produced by an operable linkage of a nucleic acid sequence to be transcribed.

The term "heterologous" refers to the relationship between two or more nucleic acid or protein sequences that are derived from different sources. For example, a promoter is heterologous with respect to an operably linked nucleic acid sequence, such as a coding sequence, if such a combination is not normally found in nature. In addition, a particular sequence may be "heterologous" with respect to a cell or organism into which it is inserted (i.e. does not naturally occur in that particular cell or organism). For example, the chimeric gene disclosed herein is a heterologous nucleic acid.

The expression "operably linked" means that said elements of the chimeric gene are linked to one another in such a way that their function is coordinated and allows expression of the coding sequence, i.e. they are functionally linked. By way of example, a promoter is functionally linked to another nucleotide sequence when it is capable of ensuring transcription and ultimately expression of said other nucleotide sequence. Two proteins encoding nucleotide sequences, e.g. a transit peptide encoding nucleic acid sequence and a nucleic acid sequence encoding a protein having HPPD activity, are functionally or operably linked to each other if they are connected in such a way that a fusion protein of first and second protein or polypeptide can be formed.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region which is functionally or structurally defined may comprise additional DNA regions etc.

As used herein, "plant part" includes any plant organ or plant tissue, including but not limited to fruits, seeds, embryos, meristematic regions, callus tissue, leaves, roots, shoots, flowers, gametophytes, sporophytes, pollen, and microspores.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other, is regarded as a position with non-identical residues. The optimal alignment of the two sequences is performed by the Needleman and Wunsch algorithm (Needleman and Wunsch 1970). The computer-assisted sequence alignment above, can be conveniently performed using standard software program such as GAP which is part of the Wisconsin Package Version 10.1 (Genetics Computer Group, Madison, Wis., USA) using the default scoring matrix with a gap creation penalty of 50 and a gap extension penalty of 3.

Nucleic acids can be DNA or RNA, single- or double-stranded. Nucleic acids can be synthesized chemically or produced by biological expression in vitro or even in vivo. Nucleic acids can be chemically synthesized using appropriately protected ribonucleoside phosphoramidites and a conventional DNA/RNA synthesizer. Suppliers of RNA synthesis reagents are Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). In connection with the chimeric gene of the present disclosure, DNA includes cDNA and genomic DNA.

The terms "protein" or "polypeptide" as used herein describe a group of molecules consisting of more than 30 amino acids, whereas the term "peptide" describes molecules consisting of up to 30 amino acids. Proteins and peptides may further form dimers, trimers and higher oligomers, i.e. consisting of more than one (poly)peptide molecule. Protein or peptide molecules forming such dimers, trimers etc. may be identical or non-identical. The corresponding higher order structures are, consequently, termed homo- or heterodimers, homo- or heterotrimers etc. The terms "protein" and "peptide" also refer to naturally modified proteins or peptides wherein the modification is effected e.g. by glycosylation, acetylation, phosphorylation and the like. Such modifications are well known in the art.

It will be clear that whenever nucleotide sequences of RNA molecules are defined by reference to nucleotide sequence of corresponding DNA molecules, the thymine (T) in the nucleotide sequence should be replaced by uracil (U). Whether reference is made to RNA or DNA molecules will be clear from the context of the application.

The following non-limiting Examples describe the use of a re-designed meganuclease to introduce a DNA of interest in close proximity to the GHB119 elite event and the generation of cotton plants comprising an HPPD gene conferring tolerance to a field dose of at least 1× of at least one HPPD inhibitor.

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

All patents, patent applications and publications mentioned herein are hereby incorporated by reference, in their entireties, for all purposes.

Throughout the description and Examples, reference is made to the following sequences:

SEQ ID NO. 1: Recognition sequence of the BAY-5/6 meganuclease (sense)
SEQ ID NO. 2: Recognition sequence of the BAY-5/6 meganuclease (reverse complement of SEQ ID NO. 1)
SEQ ID NO. 3: 3' flanking sequence of GHB119 containing the BAY-5/6 recognition site
SEQ ID NO. 4: 5' flanking sequence of GHB119
SEQ ID NO. 5: meganuclease expression vector pCV193
SEQ ID NO. 6: Amino acid sequence of the COT-5/6 single chain meganuclease
SEQ ID NO. 7: Repair DNA vector pCV211
SEQ ID NO. 8: Amino acid sequence of Pf-HPPD (W336)
SEQ ID NO. 9: Amino acid sequence of 2mEPSPS
SEQ ID NO. 10: Nucleotide sequence of Cry2A probe
SEQ ID NO. 11: Nucleotide sequence of HPPD probe
SEQ ID NO. 12: Nucleotide sequence of 2mEPSPS probe
SEQ ID NO. 13: PCR primer IB527
SEQ ID NO. 14: PCR primer IB616
SEQ ID NO. 15: PCR primer IB617
SEQ ID NO. 16: Amino acid sequence of I-CreI
SEQ ID NO. 17: PCR primer IB589
SEQ ID NO. 18: PCR primer VDS406
SEQ ID NO. 19: Amino acid sequence of the wild type (wt) *Pseudomonas fluorescens* HPPD protein
SEQ ID NO. 20: Nucleic acid sequence of T-DNA of vector pTIF16, comprising a chimeric gene according to the invention
SEQ ID NO. 21: Amino acid sequence encoding the *Pseudomonas fluorescens* HPPD protein wherein the glycine at amino acid position 336 has been replaced by a tryptophan SEQ ID NO: 22: Amino acid sequence of the 2mEPSPS protein of *Z. mays*
SEQ ID NO. 23: Nucleic acid sequence of T-DNA of vector pTSIH09, comprising a chimeric gene according to the invention The sequence listing contained in the file named "BCS11-2012-WO_ST25", which is 105 kilobytes (size as measured in Microsoft Windows®), contains 23 sequences SEQ ID NO. 1 through SEQ ID NO: 23, is filed herewith by electronic submission and is incorporated by reference herein.

EXAMPLES

All re-designed meganucleases and their expression vectors described herein have been designed by Precision BioSciences Inc., 104 T.W. Alexander Drive, Research Triangle Park, NC27713.

Example 1: Vector Construction

Using standard recombinant DNA techniques, the following DNA vector was constructed comprising the following operably linked elements (schematically depicted in FIG. 3):
Repair DNA vector pCV211 (SEQ ID NO: 7)
Nt 2252-4310: GHB119 upstream COT-5/6 recognition site: 3'flanking genomic DNA of event GHB119 upstream of the COT-5/6 recognition site.
4354-4771: P35S2c: P35S2 promoter sequence.
Nt 4772-4840: 5'cab22L: Sequence including the leader sequence of the chlorophyl a/b binding protein gene of *Petunia hybrida* (Harpster et al., 1988).
Nt 4842-5213: TPotpY-1 Pa: coding sequence of an optimized transit peptide derivative (position 55 changed into Tyr), containing sequence of the RuBisCO small subunit genes of *Zea mays* (corn) and *Helianthus annuus* (sunflower) (Lebrun et al., 1996), adapted for cotton codon usage.
Nt 5214-6290 (incl stop): hppdPfW336-1 Pa: coding sequence of the 4-hydroxyphenylpyruvate dioxygenase gene of *Pseudomonas fluorescens* strain A32 modified by the replacement of the amino acid Glycine 336 with a Tryptophane (Boudec et al., 1999), adapted to cotton codon usage.
Nt 6316-6976: 3'histonAt: sequence including the 3' untranslated region of the histone H4 gene of *Arabidopsis thaliana* (Chabouté et al., 1987).
Nt 8026-8488: intron1 h3At: first intron of gene II of the histone H3.III variant of *Arabidopsis thaliana* (Chaubet et al., 1992).
Nt 8495-8866: TPotpC: coding sequence of the optimized transit peptide, containing sequence of the RuBisCO small subunit genes of *Zea mays* (corn) and *Helianthus annuus* (sunflower) (Lebrun et al., 1996).
Nt 8867-10204: 2mepsps: coding sequence of the double-mutant 5-enol-pyruvylshikimate-3-phosphate synthase gene of *Zea mays* (corn) (Lebrun et al., 1997).
Nt 10228-10888: 3'histonAt: sequence including the 3' untranslated region of the histone H4 gene of *Arabidopsis thaliana* (Chabouté et al., 1987).
Nt 10971-12521: FGD GHB119: downstream COT-5/6 recognition site: 3'flanking genomic DNA of event GHB119 downstream of COT-5/6 recognition site.
COT-5/6 meganuclease expression vector pCV193 (SEQ ID NO: 5)
Nt 2241-2599: P35S2c (fragment): The P35S2c promoter fragment.

Nt 2602-3083: P35S2c: P35S promoter sequence.
Nt 3091-4169: COT-5/6-SC: COT-5/6 single chain meganuclease encoding DNA region.
Nt 4173-4433: 3'nos: sequence including the 3' untranslated region of the nopaline synthase gene from the T-DNA of pTiT37 (Depicker et al., 1982).

Example 2: Media and Buffers

Media and buffers used during the embryonic callus generation and transformation as described below in examples 3 and 4:
Co-cultivation substrate: M100 with 1/2 concentration MS salts, +100 µM AS+100 mg/L L-cysteIne (L-cysteïne has always to be freshly prepared and added after autoclavation), pH 5.2
M100 substrate: MS salts, B5 vitamins, MES 0.5 g/L, $MgCl_2.6H_2O$ 0.94 g/L, gelrite 2 g/L, glucose 30 g/L, pH 5.8
100Q substrate: M100 substrate+0.2 M mannitol+0.2 M sorbitol, pH5.8
M104 substrate: =M100 substrate+1 g/L $KNO_3$, pH 5.8
M700 substrate: Stewarts salts+vitamins, $MgCl_2.6H_2O$ 0.47 g/L, gelrite 1 g/L, plant agar 2.25 g/L, sucrose 20 g/L, pH 6.8
M702 substrate: Stewarts salts+vitamins, $MgCl_2.6H_2O$ 0.71 g/L, gelrite 1.5 g/L, plant agar 5 g/L, sucrose 5 g/L, pH 6.8
AC: active carbon 2 g/L
AS: acetosyringone Example 3: Generation of Friable Embryogenic Callus Cotton seeds from Coker 312 were germinated on solid germination medium M100 without hormones for 7-10 days in the dark at 26-28° C. Next, induction of embryogenic callus was performed by incubating hypocotyl explants from the seedlings on solid M100 medium (without hormones). After about 2 months when the wound callus at the cut surface of the hypocotyls starts to show fast proliferation, the further subculture for enrichment and maintenance of embryogenic callus is done on solid M100 medium with active carbon (2 g/L). Induction and maintenance of embryogenic callus occurs under dim light conditions (intensity: 1 to 7 µmol $m^{-2}$ $sec^{-1}$; photoperiod: 16H light/8H dark) at 26-28° C. (Essentially as described in U.S. provisional application 61/493,579 and EP11004570.5, herein incorporated by reference, in particular pages pages 31-35, examples 2-5).

Example 4: Transformation of Cotton Embryogenic Callus by Particle Bombardment

The following procedure was followed to transform cotton embryogenic callus using particle bombardment
Friable cotton embryogenic callus (EC) of example 3 of a target line in which to introduce a DSB induced targeted modification, is collected 2 to 3 weeks after subculture and plated in a thin layer by means of a Büchnerfilter on top of a filter paper on 100Q substrate with 0.2M mannitol and 0.2M sorbitol for ~4 to ~6 hours prior to bombardment.
After preplasmolysis on 100Q substrate for ~4 to ~6 hours, the EC is bombarded with 0.5 pmol pCV211+ 0.5pmol pCV193 or 0.75pmol pCV211+0.5pmol pCV193 or 0.75pmol pCV211+0.75 pmol pCV193.
Bombardment conditions:
diameter gold particles: 0.3-3 µm
rupture disc: 1350 psi
distance to target tissue: 9 cm
chamber vacuum ~27 (in Hg)
BioRAD PPS_1000/He Biolistic Particle delivering system
After bombardment, the filters are transferred onto M100 substrate with 0.2 M mannitol or M100 substrate without selective agent.
After 1 to 4 days on non-selective substrate under dimlight conditions at 26-28° C., the filters are transferred onto selective M100 substrate with 1 mM glyphosate.
After about 2 to 3 weeks, proliferating calli are selected from the filters and further subcultured as small piles onto selective M100 substrate with 1 mM glyphosate. After a subculture period of ~6 weeks with ~3 weekly subculture intervals, on selective M100 substrate under dimlight conditions at 26-28° C., transformed EC/somatic embryos can be selected.
A molecular screen based on PCR analysis for the identification of targeted modification events is performed at the level of transformed EC/somatic embryos.
Plant regeneration is initiated from the targeted modification events by plating EC/somatic embryos on M104 with active carbon (AC) and the corresponding selective agent under light conditions (intensity: 40 to 70 µmol $m^{-2}$ $sec^{-1}$; photoperiod: 16H light/8H dark) at 26-28° C.
After about one month individual embryos of about 0.5-1 cm are transferred on top of a filter paper on M104 with AC and 1 mM glyphosate.
Further well germinating embryos are transferred onto non-selective germination substrate M702 under light conditions (intensity: 40 to 70 µmol $m^{-2}$ $sec^{-1}$; photoperiod: 16H light/8H dark) at 26-28° C.
After one to two months the further developing embryos are transferred onto M700 substrate under light conditions (intensity: 40 to 70 µmol $m^{-2}$ $sec^{-1}$; photoperiod: 16H light/8H dark) at 26-28° C. for development into small plantlets.
(Essentially as described in U.S. provisional application 61/493,579 and EP11004570.5, herein incorporated by reference, in particular pages pages 31-35, examples 2-5)

Figure 3:
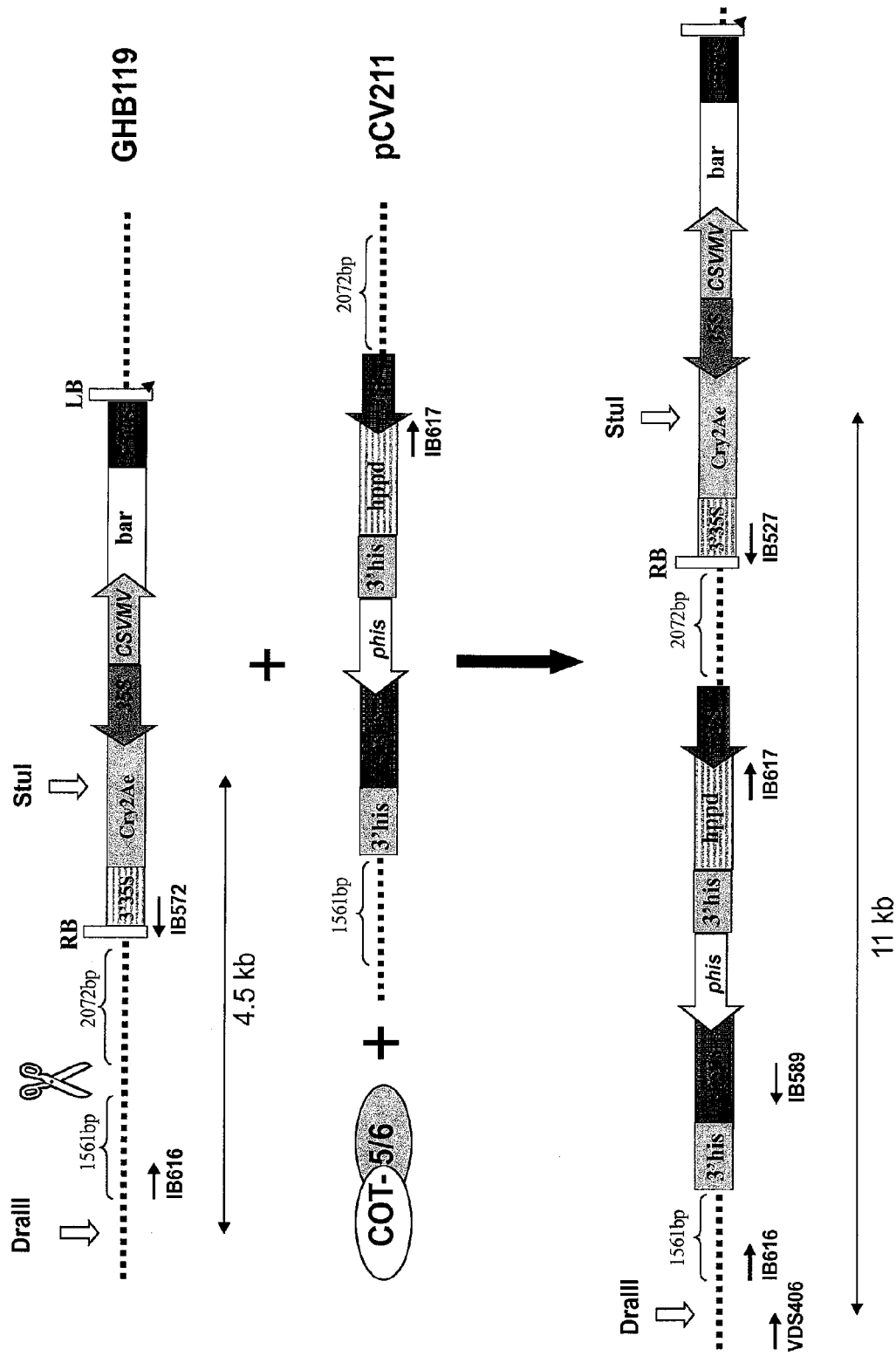
FIG. 3: Schematic overview of targeted insertion through at least one-sided homologous recombination. Scissors indicate recognition sites for DSBI enzymes (COT-5/6), block arrows represent promoters, small rectangles represent terminators, while large rectangles represent genes, small arrows represent PCR primers, double-headed arrows represent southern blotting fragments, vertical block arrows represent restriction sites, dotted lines represent flanking DNA sequences in which homologous regions are indicated by the accolades. Repair DNA vector pCV211 comprises a 2mEPSPS gene and an HPPD-336W flanked by flanking regions with homology to the regions surrounding the COT-5/6 recognition site in the 3' flanking sequence of the GHB119 elite event. After double stranded DNA break induction by COT-5/6, homologous recombination between the 1561 bp and 2072 bp flanking regions of the pCV211 vector with the corresponding regions in the 3' flanking sequence of GHB119, the 2mEPSPS gene and HPPD-336W genes of pCV211 are inserted at the target site. A correctly stacked event can be identified by PCR using primer pair IB617×IB572 and IB616×IB572 and by the identification of an 11 kb genomic band by southern blotting on DraIII/StuI digested genomic DNA with probes directed to EPSPS, HPPD or Cry2Ae.

Example 5: Targeted Modification of the Genomic Region in Close Proximity to the GHB119 Transgenic Event Via Homologous Recombination The pCV211 repair DNA vector and the pCV193 COT-5/6 meganuclease encoding vector were introduced into embryogenic calli of hemizygous GHB119 plants (described in WO2008/151780) using particle bombardment as described in example 4.
First, transformants were screened for glyphosate resistance, as this indicates insertion of the repair DNA pCV211. These were subsequently subjected to high throughput molecular analysis to identify potentially correct gene targeting events by PCR with primer pair IB527×IB616 (SEQ ID NO. 13 and 14 respectively, schematically represented in FIG. 3) using the Elongase enzyme mix from Invitrogen in a final MgCl2 concentration of 2 mM and the following cycling parameters: 2 min denaturation at 94° C., followed by 35 cycles of 94°—30 sec, 58°—30 sec, 68°—9 min, and a final elongation step of 7 min at 68° C. The presence of a PCR product of 9640 bp is indicative of a correctly stacked gene targeting event by at least one-sided homologous recombination (via the 2072 bp homology region indicated by the accolade in FIG. 3). Potentially correct stacks can also be identified by PCR with primer pair IB527×IB617 (SEQ ID NO 13 and 17 respectively,) which should then result in a PCR product of 3893 bp (FIG. 3). Subsequent sequence analysis of the PCR products allows confirming at least one-sided correct homologous recombination.

Since the absence of a PCR product could also result from poor DNA quality or large insertions or deletions at the target site, a number of glyphosate resistant calli that were positive or negative on PCR were also analyzed by southern blotting on DraIII/StuI digested genomic DNA using probes recognizing the EPSPS gene (SEQ ID NO 9), the Cry2Ae gene (SEQ ID NO 10) and the HPPD gene (SEQ ID NO 11), respectively, under stringent conditions. In case of a correct stacked event, this should result in the identification of an 11 kb band using all three probes (see also FIG. 3).

In total, at least 27 putative correct stacked events have been identified using PCR (~1.8% of the total of the 1479 identified glyR events), of which at least 13 have been confirmed to be correct gene targeting events by southern blotting as described above.

Some of the confirmed stacked events were evaluated for the functionality of the bar and Cry2Ae gene of the original GHB119 event. Via a Leaf Strip test, expression of the PAT and Cry2Ae protein could be confirmed in those events.

Further, sequence analysis of PCR fragment IB527× IB617 and IB589×VDS406 (SEQ ID NO. 17 and SEQ ID NO. 18 respectively), which span the two recombination sites (see FIG. 3), showed a perfect insertion of epsps and hppd at the target loci.

Example 6: Transmission of the Stack to Next Generations

In order to test whether all four transgenes are indeed transmitted to the next generation as a stack and do not segregate independently, offspring of crosses of a plant comprising the stack with a wild-type plants were evaluated for the presence of the transgenes.

TABLE 2

Segregation data from a cross of a targeted insertion event (i.e. heterozygous for the stacked event) with a wild type plant results in ca 50% WT and ca 50% 4 genes.

| epsps | hppd | cry2Ae | bar |
|---|---|---|---|
| WT | WT | WT | WT |
| 1 copy | 1 copy | 1 copy | 1 copy |
| 1 copy | 1 copy | 1 copy | 1 copy |
| 1 copy | 1 copy | 1 copy | 1 copy |
| 1 copy | 1 copy | 1 copy | 1 copy |
| WT | WT | WT | WT |
| WT | WT | WT | WT |
| WT | WT | WT | WT |
| WT | WT | WT | WT |
| WT | WT | WT | WT |
| 1 copy | 1 copy | 1 copy | 1 copy |
| WT | WT | WT | WT |
| WT | WT | WT | WT |
| WT | WT | WT | WT |
| WT | WT | WT | WT |
| 1 copy | 1 copy | 1 copy | 1 copy |
| 1 copy | 1 copy | 1 copy | 1 copy |
| 1 copy | 1 copy | 1 copy | 1 copy |
| WT | WT | WT | WT |
| 1 copy | 1 copy | 1 copy | 1 copy |
| 1 copy | 1 copy | 1 copy | 1 copy |
| 1 copy | 1 copy | 1 copy | 1 copy |
| WT | WT | WT | WT |
| WT | WT | WT | WT |

TABLE 3

Segregation data from a selfed progeny (i.e. homozygous for the stacked event) with a wild type plant results in ca 25% WT and ca 75% 4 genes.

| epsp | hppd | cry2Ae | bar |
|---|---|---|---|
| WT | WT | WT | WT |
| 1 copy | 1 copy | 1 copy | 1 copy |
| 2 copies | 2 copies | 2 copies | 2-3 copies |
| 1 copy | 1 copy | 1 copy | 1 copy |
| 1 copy | 1 copy | 1 copy | 1 copy |
| 2 copies | 2 copies | 2 copies | 2 copies |
| WT | WT | WT | WT |
| WT | WT | WT | WT |
| 1 copy | 1 copy | 1 copy | 1 copy |
| 1 copy | 1 copy | 1 copy | 1 copy |
| 1 copy | 1 copy | 1 copy | 1 copy |
| WT | WT | WT | WT |
| 1 copy | 1 copy | 1 copy | 1 copy |
| 1 copy | 1 copy | Failed | 1 copy |

Thus, table 2 and 3 show that the stacked event indeed inherits as a single genetic unit.

Example 7: Expression and Functionality of the Transgenes in the Stack

A number of stacked events were evaluated for expression of the transgenes using Q-PCR analysis and western blotting. Expression of all four transgenes was observed, albeit sometimes with varying expression levels (which correlated between the two detection methods). Also, tolerance to HPPD-inhibitor herbicides was evaluated in the greenhouse in progenies from the stacked events. The plants displayed some mild bleaching after a 2×TBT treatment but recovered afterwards.

Example 8: Generation of Cotton Plants Comprising Chimeric HPPD Genes

Using conventional recombinant DNA techniques the pTIF16 and pTSIH09 T-DNA expression vector were constructed, both comprising an HPPD encoding chimeric gene, under the control of the 35S and CsVMV promoter respectively, and an EPSPS encoding chimeric gene, with the following operably linked DNA fragments:

pTIF16 (SEQ ID NO. 20)
HPPD chimeric gene:
a) P35S2: sequence including the promoter region of the Cauliflower Mosaic Virus 35S transcript (Odell et al., 1985): nt position 88 to 506 of SEQ ID NO: 20
b) 5'cab22L: sequence including the leader sequence of the chlorophyl a/b binding protein gene of *Petunia hybrida* (Harpster et al., 1988): nt position 507-576 of SEQ ID NO: 20
c) TPotpY-1 Pa: coding sequence of an optimized transit peptide derivative (pos 55 changed into Tyr), containing sequence of the RuBisCO small subunit genes of *Z. mays* (corn) and *H. annuus* (sunflower) (Lebrun et at., 1996), adapted for cotton codon usage: nt position 577-948 of SEQ ID NO: 20
d) hppdPfW336-1 Pa: coding sequence of the 4-hydroxyphenylpyruvate dioxygenase gene of *Pseudomonas fluorescens* strain A32 modified by the replacement of the amino acid Glycine 336 with a Tryptophane (Boudec et al., 2001), adapted to cotton codon usage: nt position 949-2025 of SEQ ID NO: 20 (codon encoding tryptophan at position 336 found at nt 1954-1956)

e) 3'histonAt: sequence including the 3' untranslated region of the histone H4 gene of *Arabidopsis thaliana* (Chabouté et all., 1987): nt position 2026-2714 of SEQ ID NO: 20

EPSPS Chimeric Gene:
a) Ph4a748 ABC: sequence including the promoter region of the histone H4 gene of *Arabidopsis thaliana* (Chabouté et aI., 1987): nt position 2791-3750 of SEQ ID NO: 20
b) intron1 h3At: first intron of gene II of the histone H3.III variant of *Arabidopsis thaliana* (Chaubet et al., 1992): nt position 3751-4229 of SEQ ID NO: 20
c) TPotp C: coding sequence of the optimized transit peptide containing sequence of the RuBisCO small subunit genes of *Zea mays* (corn) and *Helianthus annuus* (sunflower) (Lebrun et al., 1996): nt position 4230-4601 of SEQ ID NO: 20
d) 2mepsps: the coding sequence of the double-mutant 5-enol-pyruvylshikimate-3-phosphate synthase gene of *Zea mays* (corn) (Lebrun et aI, 1997): nt position 4602-5939 of SEQ ID NO: 20
e) 3'histonAt: sequence including the 3' untranslated region of the histone H4 gene of *Arabidopsis thaliana* (Chaboute et al., 1987): nt position 5940-6630 of SEQ ID NO: 20 pTSIH09 (SEQ ID NO. 23)

HPPD Chimeric Gene:
a) Pcsvmv XYZ: sequence including the promoter region of the Casava Vein Mosaic Virus (Verdaguer et al., 1996): nt position 2735-2223 of SEQ ID NO: 23
b) TPotpY-1 Pa: coding sequence of an optimized transit peptide derivative (pos 55 changed into Tyr), containing sequence of the RuBisCO small subunit genes of *Z. mays* (corn) and *H. annuus* (sunflower) (Lebrun et al., 1996), adapted for cotton codon usage: nt position 2214-1845 of SEQ ID NO: 23
c) hppdPfW336-1 Pa: coding sequence of the 4-hydroxy-phenylpyruvate dioxygenase gene of *Pseudomonas fluorescens* strain A32 modified by the replacement of the amino acid Glycine 336 with a Tryptophane (Boudec et al., 2001), adapted to cotton codon usage: nt position 1842-766 of SEQ ID NO: 23
d) 3'histonAt: sequence including the 3' untranslated region of the histone H4 gene of *Arabidopsis thaliana* (Chabouté et all., 1987): nt position 749-83 of SEQ ID NO: 23

EPSPS Chimeric Gene:
a) Ph4a748 ABC: sequence including the promoter region of the histone H4 gene of *Arabidopsis thaliana* (Chabouté et aI., 1987): nt position 2834-3750 of SEQ ID NO: 23
b) intron1 h3At: first intron of gene II of the histone H3.III variant of *Arabidopsis thaliana* (Chaubet et al., 1992): nt position 3790-4255 of SEQ ID NO: 23
c) TPotp C: coding sequence of the optimized transit peptide containing sequence of the RuBisCO small subunit genes of *Zea mays* (corn) and *Helianthus annuus* (sunflower) (Lebrun et al., 1996): nt position 4269-4640 of SEQ ID NO: 23
d) 2mepsps: the coding sequence of the double-mutant 5-enol-pyruvylshikimate-3-phosphate synthase gene of *Zea mays* (corn) (Lebrun et aI, 1997): nt position 4641-5978 of SEQ ID NO: 23
e) 3'histonAt: sequence including the 3' untranslated region of the histone H4 gene of *Arabidopsis thaliana* (Chaboute et al., 1987): nt position 5999-6665 of SEQ ID NO: 23

The T-DNA vectors pTIF16 and pTSIH09 were introduced into *Agrobacterium tumefaciens* C58C1Rif (pEHA101) and transformants were selected using spectinomycin and streptomycin according to methods known in the art.

The *Agrobacterium* strains were used to transform the cotton var. "Coker 312" according to methods known in the art and transgenic plants were selected in vitro for tolerance to glyphosate (1.0-1.5 mM) and analyzed for copy number using RT-PCR. T0 plants containing the transgenes were selfed and the resulting T1 generation was used for herbicide tolerance tests in the greenhouse.

Example 9: Assessment of Herbicide Tolerance in the Greenhouse

To analyze for herbicide tolerance, a segregating T1 population of 100 seeds of a pTIF16 and a pTSIH09 event was sown in a greenhouse. Emerging plants were treated at growth stage with different HPPD inhibitors in different field doses. 13 and 24 DPA (days post application), plants were scored for phenotype ("damage scores") on a scale of 0-100, whereby 0 represents no damage (i.e. corresponding to untreated wild-type plants) and 100 represents maximum damage (i.e. displaying damage on all aerial parts) (Table 4).

TABLE 4

Damage scoring of cotton plants of the pTIF16 and the pTSIH09 events comprising the chimeric *Pseudomonas fluorescens* (Pf)-HDDP-336W gene, as well as wt controls (Coker312) after herbicide treatment or treatment with the formulation without the herbicide (blind).

| | | | | Damage scores (% damage) | | | | | |
|---|---|---|---|---|---|---|---|---|---|
| Treatments (post-emergent) | | | | Coker | | pTIF16 | | pTSIH09 | |
| | | Dosage of test | | WT average of 3 plants per treatment | | homozygote average of 6 plants per treatment | | heterozygote average of 10-11 plants per treatment | |
| Test compound | sprayed as | compound (g/ha) | Field rate equivalent | 13 dpa | 24 dpa | 13 dpa | 24 dpa | 13 dpa | 24 dpa |
| Blank | | — | — | 4 | 4 | 0 | 0 | 0 | 0 |
| Tembotrione | | 200 | 2x | 65 | 94 | 6 | 4 | 18 | 15 |
| | | 400 | 4x | 65 | 96 | 12 | 14 | 25 | 27 |
| Mesotrione | Callisto (SC10) | 200 | 2x | 68 | 95 | 11 | 10 | 23 | 19 |
| | | 400 | 4x | 68 | 96 | 21 | 24 | 29 | 39 |
| Topramezone | Clio/ Impact (SC30) | 36 | 2x | 67 | 97 | 0 | 1 | 7 | 9 |
| | | 72 | 4x | 68 | 96 | 0 | 3 | 9 | 11 |

TABLE 4-continued

Damage scoring of cotton plants of the pTIF16 and the pTSIH09 events comprising the chimeric *Pseudomonas fluorescens* (Pf)-HDDP-336W gene, as well as wt controls (Coker312) after herbicide treatment or treatment with the formulation without the herbicide (blind).

| | | | | Damage scores (% damage) | | | | | |
|---|---|---|---|---|---|---|---|---|---|
| Treatments (post-emergent) | | | | Coker | | pTIF16 | | pTSIH09 | |
| | | Dosage of test | | WT average of 3 plants per treatment | | homozygote average of 6 plants per treatment | | heterozygote average of 10-11 plants per treatment | |
| Test compound | sprayed as | compound (g/ha) | Field rate equivalent | 13 dpa | 24 dpa | 13 dpa | 24 dpa | 13 dpa | 24 dpa |
| Isoxaflutole | Balance (WG75) | 200 | 2x | 50 | 67 | 2 | 1 | 6 | 8 |
| | | 400 | 4x | 65 | 70 | 6 | 5 | 8 | 9 |

Example 10: Assessment of Herbicide Tolerance in the Field

Field trials for herbicide tolerance were conducted at two locations in the US, i.e. California (CA) and Tennessee (TN), with two replicates per location. Plants homozygous for the pTIF16 event in Coker 312 background, along with control plants (wt segregants derived from the same line or Coker 312 plants) were sown in plots of ca. 40 plants and treated with a broad spectrum of HPPD inhibitor herbicides at commercial concentrations (at least 1×) in a post-emergent treatment at the 2-4 leaf stage (except for Balance Flex which was applied pre-emergence in CA and post-emergent in TN). Tolerance was evaluated by scoring for plant response (taking into account the extent of chlorosis, bleaching and necrosis) 7, 21 and 28 days after treatment (DAT) on a scale of 0-100 (wherein 0 corresponds to no chlorosis/bleaching/necrosis and 100 indicates death of the plant). Results were averaged for the two locations (table 5). While wt plants displayed significant chlorosis, bleaching and necrosis in response to the herbicide treatment, plants homozygous for the pTIF16 event were tolerant to all HPPDi herbicides tested.

TABLE 5

Plant response (chlorosis, bleaching and necrosis) of cotton plants homozygous (hom) and azygous (wt) for the pTIF16 event comprising the chimeric *Pseudomonas fluorescens* (Pf)-HDDP-336W gene.

| | | 7 DAT | | 21 DAT | | 28 DAT | |
|---|---|---|---|---|---|---|---|
| treatment | 1X a.i. | wt | hom | wt | hom | wt | hom |
| Untreated | — | 0.0 | 0.0 | 0.0 | 0.0 | 0.0 | 0.0 |
| Tembo-trione* | 100 g a.i./ha | 87.8 | 26.3 | 83.8 | 2.8 | 72 | 1.8 |
| Laudis SC | a.i. Tembotrione, 138 g a.i./ha | 81.3 | 9.5 | 56.8 | 5.5 | 50 | 0.3 |
| Callisto | a.i. Mesotrione, 105 g a.i./ha | 86.3 | 0.5 | 53.3 | 0.0 | 67.5 | 0.0 |
| Balance Flex** | a.i. Isoxaflutole, 105 g a.i./ha | 42.5 | 10 | 99 | 4 | n/a | n/a |
| Impact | Topramezone, 18.41 g a.i./ha | 92.5 | 7.8 | 62.5 | 1.3 | 83.6 | 0.0 |
| Pyra-sulfutole | 37.5 g a.i./ha | 83.8 | 0.0 | 58.3 | 3.5 | 62.5 | 0.0 |

*TBT treatment CA applied 1 week earlier than other treatments,
**Balance Flex treatment CA only pTIF16 homozygous plants were also fully tolerant to a pre-emergence treatment with Balance Flexx (Isoxaflutole, 105 g a.i./ha).

Example 11: Pre-Emergence and Post-Emergence Herbicide Tolerance in the Field Similar as above, field trials were conducted in Argentina with one pTIF16 event and two pTSHI09 events (homozygotes) in comparison with the wild type Coker 312 line. Pre-emergence tolerance was evaluated for 2× and 4× Balance Pro (IFT) and 4× Callisto (MST) at 7, 14 and 21 days after treatment (DAT). Post emergence tolerance was tested for 2×IFT, 4×IFT, 2×MST, 2×TBT, 4×TBT 2× Topramezone (Top) and 4× glyphosate. Results (plant response) are depicted in table 6 and 7 below.

TABLE 6

Pre-emergence herbicide tolerance in the field reflected as plant response (chlorosis, bleaching and necrosis).

| | Pre | | | | | | | | |
|---|---|---|---|---|---|---|---|---|---|
| | Balance Pro 2X IFT 2x | | | Balance Pro 4x IFT 4x | | | Callisto MST 4x | | |
| DAT | 7 | 14 | 21 | 7 | 14 | 21 | 7 | 14 | 21 |
| Coker | 24.3 | 81.7 | 85.3 | 40.0 | 91.3 | 95.2 | 38.3 | 83.3 | 82.8 |
| pTIF16-01 | 3.7 | 7.7 | 4.7 | 2.3 | 7.0 | 1.8 | 4.7 | 7.3 | 2.7 |
| PTSIH09-01 | 1.0 | 4.3 | 0.8 | 2.3 | 0.0 | 0.3 | 3.3 | 3.0 | 0.8 |
| PTSIH09-02 | 2.7 | 2.3 | 1.5 | 2.0 | 3.0 | 1.0 | 4.3 | 5.3 | 4.0 |

TABLE 7

Post-emergence herbicide tolerance in the field reflected as plant response (chlorosis, bleaching and necrosis).

| | Post | | | | | | | | | |
|---|---|---|---|---|---|---|---|---|---|---|
| | IFT 2x | | | | | IFT 4x | | | | |
| DAT | 4 | 7 | 14 | 24 | 36 | 4 | 7 | 14 | 24 | 36 |
| Coker | 14.7 | 32.8 | 75.8 | 84.5 | 85.3 | 18.3 | 36.7 | 68.3 | 81.5 | 80.8 |
| PTIF16-01 | 2.3 | 2.8 | 1.5 | 4.2 | 5.8 | 1.7 | 1.7 | 1.2 | 1.0 | 0.8 |
| pTSIH09-01 | 0.7 | 3.5 | 1.0 | 0.5 | 2.5 | 2.3 | 0.7 | 0.7 | 0.2 | 0.0 |
| pTSIH09-02 | 0.7 | 2.3 | 1.7 | 4.2 | 7.5 | 0.7 | 0.8 | 1.0 | 0.0 | 0.0 |

| | Meso 2x | | | | | TBT 2x | | | | |
|---|---|---|---|---|---|---|---|---|---|---|
| DAT | 4 | 7 | 14 | 24 | 36 | 4 | 7 | 14 | 24 | 36 |
| Coker | 18.0 | 43.0 | 95.3 | 100.0 | 100.0 | 18.0 | 43.7 | 93.3 | 100.0 | 100.0 |
| PTIF16-01 | 7.3 | 30.2 | 25.5 | 28.5 | 24.2 | 11.3 | 21.5 | 21.7 | 17.0 | 13.7 |
| PTSIH09-01 | 7.3 | 36.0 | 28.3 | 31.2 | 26.7 | 8.7 | 23.5 | 22.5 | 19.2 | 16.0 |
| PTSIH09-02 | 6.0 | 35.0 | 32.7 | 34.5 | 32.5 | 9.7 | 22.3 | 23.8 | 20.8 | 16.8 |

| | TBT 4x | | | | | Top 4x | | | | |
|---|---|---|---|---|---|---|---|---|---|---|
| DAT | 4 | 7 | 14 | 24 | 36 | 4 | 7 | 14 | 24 | 36 |
| Coker | 15.0 | 44.7 | 95.0 | 99.2 | 100.0 | 15.3 | 43.0 | 92.5 | 100.0 | 99.8 |
| PTIF16-01 | 5.3 | 19.2 | 20.7 | 13.0 | 11.7 | 7.3 | 17.7 | 22.7 | 16.5 | 12.5 |
| PTSIH09-01 | 8.3 | 22.8 | 20.7 | 15.2 | 15.3 | 5.3 | 19.5 | 21.2 | 15.7 | 12.8 |
| PTSIH09-02 | 5.3 | 23.0 | 21.7 | 17.0 | 16.7 | 6.3 | 16.8 | 18.5 | 17.5 | 16.3 |

| | Gly 4x | | | | |
|---|---|---|---|---|---|
| DAT | 4 | 7 | 14 | 24 | 36 |
| Coker | 46.7 | 93.3 | 99.5 | 99.3 | 100.0 |
| PTIF16-01 | 0.0 | 0.0 | 0.0 | 0.0 | 0.0 |
| pTSIH09-01 | 0.0 | 0.0 | 0.5 | 0.8 | 2.5 |
| pTSIH09-02 | 0.0 | 0.0 | 0.0 | 0.5 | 2.8 |

---

The invention claimed is:

1. A cotton plant cell, plant part, plant, or seed comprising a chimeric gene comprising
   (a) a nucleic acid sequence encoding a protein having HPPD activity, wherein said protein has at least 95% sequence identity to the amino acid sequence of SEQ ID NO: 21 and has a tryptophan at a position corresponding to position 336 of SEQ ID NO: 19, and wherein said protein provides to said plant tolerance to a field dose of at least 1× of at least one HPPD inhibitor, said sequence operably linked to
   (b) a plant expressible promoter, which is a 35S or CsVMV promoter.

2. The cotton plant cell, plant part, plant, or seed of claim 1, wherein said nucleic acid sequence is optimized for expression in cotton.

3. The cotton plant cell, plant part, plant, or seed of claim 1, wherein said protein comprises the amino acid sequence of SEQ ID NO: 21 or is encoded by a nucleic acid comprising the nucleotide sequence of SEQ ID NO: 20 from position 949 to position 2025.

4. The cotton plant cell, plant part, plant, or seed of claim 1, wherein the protein provides the plant tolerance to a field dose of at least 1.5× of said at least one HPPD inhibitor.

5. The cotton plant cell, plant part, plant, or seed of claim 1, wherein the protein provides the plant tolerance to a field dose of at least 2× of said at least one HPPD inhibitor.

6. The cotton plant cell, plant part, plant, or seed of claim 1, wherein said at least one HPPD inhibitor is selected from mesotrione, isoxaflutole, topramezone, pyrasulfutole or tembotrione, or combinations thereof.

7. The cotton plant cell, plant part, plant, or seed of claim 6, which is tolerant to at least two HPPD inhibitors.

8. The cotton plant cell, plant part, plant, or seed of claim 1, wherein said chimeric gene comprises the nucleic acid sequence of SEQ ID NO: 20 from position 88 to position 2714 or where said chimeric gene comprises the nucleic acid sequence of SEQ ID NO: 23 from position 2735 to 83.

9. A method for obtaining a cotton plant or plant cell tolerant to field dose of at least 1× of at least one HPPD inhibitor, comprising introducing the chimeric gene of claim 1 into a cotton plant or plant cell.

10. A method for controlling weeds in the vicinity of a cotton plant or on a plant field comprising the cotton plant cell, plant part, plant, or seed of claim 1 comprising applying at least one HPPD inhibitor to the vicinity of the cotton plant or to the cotton plant field in a field dose of at least 1×.

11. The method of claim 9, wherein said at least one HPPD inhibitor is mesotrione, isoxaflutole, topramezone, pyrasulfutole or tembotrione, or combinations thereof.

12. The method of claim 9, wherein said at least one HPPD inhibitor is applied in a field dose of at least 1.5×.

13. The method of claim 9, wherein said at least one HPPD inhibitor is isoxaflutole and mesotrione, wherein said isofluxatole is applied pre-emergence and said mesotrione is applied post-emergence.

14. A method of producing a cotton plant, or plant cell, plant part, or seed thereof that is tolerant to a field dose of at least 1× of at least one HPPD inhibitor, comprising introducing into the cotton plant, or plant cell, plant part, or seed thereof a nucleic acid sequence encoding a protein having HPPD activity, wherein said protein has a tryptophan at a position corresponding to position 336 of SEQ ID NO: 19.

15. The cotton plant cell, plant part, plant, or seed of claim 7, which is tolerant to at least three, four, five, or six HPPD inhibitors.

16. The cotton plant cell, plant part, plant, or seed of claim 1, wherein the chimeric gene further comprises
   (c) a translational termination and polyadenylation region.

17. The method of claim 9, wherein the chimeric gene further comprises (c) a translational termination and polyadenylation region.

18. The method of claim 10, wherein said at least one HPPD inhibitor is mesotrione, isoxaflutole, topramezone, pyrasulfutole or tembotrione, or combinations thereof.

19. The method of claim 10, wherein said at least one HPPD inhibitor is applied in a field dose of at least 1.5×.

20. The method of claim 10, wherein said at least one HPPD inhibitor is isoxaflutole and mesotrione, wherein said isofluxatole is applied pre-emergence and said mesotrione is applied post-emergence.

21. The cotton plant cell, plant part, plant, or seed of claim 1, wherein said promoter is the CsVMV promoter.

22. The cotton plant cell, plant part, plant, or seed of claim 1, wherein said promoter is the 35S promoter.

23. The cotton plant cell, plant part, plant, or seed of claim 1, wherein said 35S promoter comprises the nucleotide sequence of SEQ ID NO: 20 from position 88 to position 506 or wherein said CsVMV promoter comprises the nucleic acid sequence of SEQ ID NO: 23 from position 2735 to 2223.

24. The method of claim 9, wherein said protein comprises the amino acid sequence of SEQ ID NO: 21 or is encoded by a nucleic acid comprising the nucleotide sequence of SEQ ID NO: 20 from position 949 to position 2025.

25. The method of claim 9, wherein said promoter is the CsVMV promoter.

26. The method of claim 9, wherein said promoter is the 35S promoter.

27. The method of claim 9, wherein said 35S promoter comprises the nucleotide sequence of SEQ ID NO: 20 from position 88 to position 506 or wherein said CsVMV promoter comprises the nucleic acid sequence of SEQ ID NO: 23 from position 2735 to 2223.

28. The method of claim 9, wherein said chimeric gene comprises the nucleic acid sequence of SEQ ID NO: 20 from position 88 to position 2714 or wherein said chimeric gene comprises the nucleic acid sequence of SEQ ID NO: 23 from position 2735 to 83.

* * * * *